United States Patent
Wolfe et al.

(10) Patent No.: US 9,447,146 B2
(45) Date of Patent: Sep. 20, 2016

(54) GUANYLYLCYCLASE C LIGANDS

(71) Applicant: Thomas Jefferson University, Philadelphia, PA (US)

(72) Inventors: Hank Wolfe, Glenmoore, PA (US); Scott A. Waldman, Ardmore, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 14/057,596

(22) Filed: Oct. 18, 2013

(65) Prior Publication Data

US 2014/0147380 A1    May 29, 2014

Related U.S. Application Data

(62) Division of application No. 11/166,592, filed on Jun. 24, 2005, now Pat. No. 8,563,682.

(60) Provisional application No. 60/583,039, filed on Jun. 25, 2004.

(51) Int. Cl.

| | |
|---|---|
| *C07K 7/04* | (2006.01) |
| *A61K 38/04* | (2006.01) |
| *A61K 38/08* | (2006.01) |
| *C07K 7/08* | (2006.01) |
| *A61K 47/48* | (2006.01) |
| *C12Q 1/18* | (2006.01) |
| *C12Q 1/25* | (2006.01) |
| *G01N 33/573* | (2006.01) |
| *G01N 33/574* | (2006.01) |
| *A61K 41/00* | (2006.01) |
| *A61K 49/00* | (2006.01) |

(52) U.S. Cl.
CPC ............... *C07K 7/08* (2013.01); *A61K 38/08* (2013.01); *A61K 41/0057* (2013.01); *A61K 41/0071* (2013.01); *A61K 47/48246* (2013.01); *A61K 49/0056* (2013.01); *C12Q 1/18* (2013.01); *C12Q 1/25* (2013.01); *G01N 33/573* (2013.01); *G01N 33/574* (2013.01); *G01N 33/57492* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 5,443,816 A | 8/1995 | Zamora et al. | |
| 5,518,888 A | 5/1996 | Waldman | |
| 5,601,990 A | 2/1997 | Waldman | |
| 5,879,656 A | 3/1999 | Waldman | |
| 5,962,220 A * | 10/1999 | Waldman | 435/6.14 |
| 6,060,037 A | 5/2000 | Waldman | |
| 6,087,109 A * | 7/2000 | Waldman | 435/6.14 |
| 6,268,159 B1 | 7/2001 | Waldman | |
| 7,097,839 B1 * | 8/2006 | Waldman | 424/178.1 |
| 7,214,786 B2 * | 5/2007 | Kovalic et al. | 536/23.6 |
| 8,206,704 B2 | 6/2012 | Waldman et al. | |
| 2001/0029019 A1 | 10/2001 | Waldman | |
| 2005/0020811 A1 | 1/2005 | Currie et al. | |
| 2005/0287067 A1 * | 12/2005 | Wolfe et al. | 424/1.69 |

FOREIGN PATENT DOCUMENTS

| | | |
|---|---|---|
| WO | WO 95/11694 | 5/1995 |
| WO | WO 97/42506 | 11/1997 |
| WO | 0105757 | 1/2001 |
| WO | 02078683 | 10/2002 |

OTHER PUBLICATIONS

Sequence 194785 from patent U.S. Pat. No. 7,214,786 (Kovalic et al. GenBak: ABU07316.1 Aug. 10, 2007).*
Peptidase M16 [Oceanimonas smirnovii] (NCBI Reference Sequence: WP_026344946.1, Jun. 9, 2014).*
Wolfe and Waldman (J. Med. Chem. 2002 45: 1731-1734).*
Penicillamine-MeSH-NCBI (1964).*
Gariepy et al., "Importance of disulfide bridges in the structure and activity of *Escherchia coli* enteotoxin ST1b," Proceedings of the National Academy of Sciences of the United States of America (1987) 84(24):8907-8911.
Hidaka et al., "Synthesis and biological properties of carba-analogs of heat-stable enterotoxin (ST)produced by enterotoxigenic," Biochemical and Biophysical Research Communications (1994) 958-965.
Shailubhai "Therapeutic applications of guanylate cyclase-C receptor agonists," Current Opinion in Drug Discovery and Development (2002) 5(2):261-268.
Gali et al., "In vivo evaluation of an 111In-labeled ST-peptide analog for specific-targeting of human colon cancers," Nuclear Medicine and Biology (2001) 28(8):903-909.
Yamasaki et al., "Structural requirements for the spatial structure and toxicity of heat-stable enterotoxin (STh) of enterotoxigenic *Escherichia coli*," Bulletin of the Chemical Society of Japan (1988) 61:1701-1706.
Carpick et al., "Structural characterization of functionally important regions of the *Escherichia coli* heat-stable enterotoxin STIb," Biochemistry (1991) 30(19):4803-4809.
Conzelmann, M., et al., "Cytokeratin 20 and guanylyl cyclase C mRNA is largely present in lymph node and liver specimens of colorectal cancer patients," Int J. Cancer (2003) 107(4): 617-28.
Cagir, B., et al., "Guanylyl cyclase C messenger RNA is a biomarker for recurrent stage II colorectal cancer," Ann. Intern Med (1999) 131(11): 805-12.
Bustin, S.A., et al., "Quantification of cytokeratin 20, carcinoembryonic antigen and guanylyl cylclase C mRNA levels in lymph nodes may not predict treatment failure in colorectal cancer patients," Int J. Cancer (2004) 108(3):412-7.

(Continued)

Primary Examiner — Peter J Reddig
(74) Attorney, Agent, or Firm — Pepper Hamilton LLP

(57) ABSTRACT

Guanylin cyclase C compound of the inventions are disclosed. Conjugated compounds comprising guanylin cyclase C compound of the inventions conjugated to detectable or therapeutic moieties are disclosed. Methods of detecting, imaging and treating cancer and treating diarrhea are disclosed.

16 Claims, 6 Drawing Sheets

(56) References Cited

OTHER PUBLICATIONS

Pearlman, J.M., et al., "A splice variant of the transcript for guanylyl cyclase C is expressed in human colon and colorectal cancer cells," *Dig Dis Sci* (2000) 45(2):298-305.
Waldman, S.A., et al., "Use of guanylyl cyclase C for detecting micrometastases in lymph nodes of patients with colon cancer," *Dis Colon Rectum* (1998) 41(3): 310-5.
Salto-Tellez, M., et al., "Intrinsic variability in the detection of micromatastases in lymph nodes for re-staging of colorectal cancer. Effect of individual markers and tissue samples," *Eur J. Cancer* (2003) 39(9): 1234-41.
Chen, G., et al., "Detection of occult metastasis in lymph nodes from colorectal cancer patients: a multiple-marker reverse transcriptase-polymerase chain reaction study," *Dis Colon Rectum* (2004) 47(5): 679-86.
Notarnicola, M., et al., "K-ras and p53 mutation in DNA extracted from colonic epithelial cells exfoliated in faeces of patients with colorectal cancer," *Dig Liver Dis* (2000) 32(2): 131-6.
Hugues, M., et al., "Identification and characterization of a new family of high-affinity receptors for *Escherichia coli* heat-stable enterotoxin in rat intestinal membranes," *Biochemisry* (1991) 30(44): 10738-45.
Carrithers, S.L., et al., "*Escherichia coli* heat-stable enterotoxin receptors. A novel marker for colorectal tumors," *Dis Colon Rectum* (1996) 39(2): 171-81.
Carrithers, S.L., et al., "Guanylyl cyclase C is a selective marker for metastatic colorectal tumors in human extraintestinal tissues," *Proc Natl Acad Sci U S A* (1996) 93(25):14827-32.
Carrithers, S.L., et al., "*Escherichia coli* heat-stable toxin receptors in human colonic tumors," *Gastroenterology* (1994) 107(6): 1653-61.
Bustin, S.A., et al., "Detection of cytokeratins 19/20 and guanylyl cyclase C in peripheral blood of colorectal cancer patients. Br J Cancer," (1999) 79(11-12): 1813-20.
Pitari, G.M., et al., "Guanylyl cyclase C agonists regulate progression through the cell cycle of human colon carcinoma cells," *Proc Natl Acad Sci U S A*, (2001) 98(14): 7846-51.
Tien, Y.W., et al., "Simultaneous detection of colonic epithelial cells in portal venous and peripheral blood during colorectal cancer surgery," *Dig Colon Rectum* (2002) 45(1): 23-9.
Park, J., et al., "Ectopic expression of guanylyl cyclase C in adenocarcinomas of the esophagus and stomach," *Cancer Epidemiol Biomarkers Prev*, (2002) 11(8): 739-44.
Pitari, G.M., et al., "Bacterial enterotoxins are associated with resistance to colon cancer," *Proc Natl Acad Sci U S A*, (2003) 100(5): 2695-9.
Vlems, F.A., et al., "Investigations for a multi-marker RT-PCR to improve sensitivity of disseminated tumor cell detection," *Anticancer Res*, (2003) 23(1A): 179-86.
Tien, Y.W., et al., "The role of gelatinase in hepatic metastasis of colorectal cancer," *Clin Cancer Res*, (2003) 9(13): 4891-6.
Chen, W.S., et al., "Impact of Circulating Free Tumor Cells in the Peripheral Blood of Colorectal Cancer Patients during Laparascopic Surgery," *World J Surg* (2004) 28:552-557.
Tien, Y.W., et al., "Intravastion-Related Metastatic Factors in Colorectal Cancer," *Tumour Biol*, (2004) 25(1-2): 48-55.
Sindice, A., et al., "Guanylin, uroguanylin, and heat-stable enterotoxin active guanylate cyclase C and/or a pertussis toxin-sensitive G protein in human proximal lubule cells," *J Biol Chem* (2002) 277(20): 17758-64.
Kulaksiz, H., et al., "Guanylin in the human pancreas: a novel luminocrine regulatory pathway of electrolyte secretion via cGMP and CFTR in the ductal system," *Histochem Cell Bio* (2001) 115(2): 131-45.
Kulaksiz, H., et al., "Guanylin and functional coupling proteins in the human salivary glands and gland tumors: expression, cellular localization, and target membrane domains," *Am J Patho* (2002) 161(2): 655-64.
Kulaksiz, H., et al., "Guanylin regulates chloride secretion in the human gallbladder via the bile fluid," *Gastroenterology* (2004) 126(3): 732-40.
Fava, T.A., et al., "Ectopic expression of guanylyl cyclase C in CD 34+ progenitor cells in peripheral blood," *J Clin Oncol* (2001) 19(19): 3951-9.
Sweet, R.M., et al., "Hemoglobin tertiary structural change on ligand binding its role in the co-operative mechanism," *J. Mol. Biol.* (1983) 171(4):479-488.
Merrifield "Solid Phase Peptide Synthesis. I. The Synthesis of a Tetrapeptide," *J. Am. Chem. Soc.* (1963) 15:2149-2154.
The Proteins, vol. II, 3d Ed., p. 105-237, Neurath, H. et al., Eds., Academic Press, New York, N.Y. (1976).
Magerstadt, M. Antibody Conjugates and Malignant Disease. (1991) CRC Press, Boca Raton, USA, pp. 110-152.
Wessels, B. W., et al. "Radionuclide selection and model absorbed dose calculations for radiolabeled tumor associated antibodies ," (1984) *Med. Phys.* 11(5):638-645.
Kwok, C. S., et al. "Calculation of radiation doses for nonuniformity distributed beta and gamma radionuclides in soft tissue," (1985) *Med. Phys.* 12(4):405-412.
Maier A., et al., "Effect of photodynamic therapy in a multimodal approach for advanced carcinoma of the gastro-esophageal junction," *Lasers in Surgery and Medicine* 26(5):461-466 (2000).
Alexander, R J. et al. Oncogene alterations in rat colon tumors induced by N-methyl-N-nitrosourea, American Journal of the Medical Sciences. 303(1):16-24, 1992.
Takekawa, M. et al., "Chromosomal localization of the protein tyrosine phosphatase G1 gene and characterization of the aberrant transcripts in human colon cancer cells," *FEBS Letters* (Feb. 21, 1994) 339(3):222-8.
Bold, R J. et al., "Experimental gene therapy of human colon cancer," *Surgery* (Aug. 1994) 116(2):189-95; discussion 195-6, (1994).
Yokozaki, H., et al., "An antisense oligodeoxynucleotide that depletes RI alpha subunit of cyclic AMP-dependent protein kinase induces growth inhibition in human cancer cells," *Cancer Research* (Feb. 15, 1993) 53(4):868-72.
Ciardiello, F. et al., "Inhibition of CRIPTO expression and tumorigenicity in human colon cancer cells by antisense RNA and oligodeoxynucleotides," *Oncogene* (Jan 1994) 9(1):291-8.
Sizeland, A M., et al., "Antisense transforming growth factor alpha oligonucleotides inhibit autocrine stimulated proliferation of a colon carcinoma cell line," *Molecular Biology of the Cell* (Nov. 1992) 3(11):1235-43.
Ullrich, et al., "Insulin-like growth factor I receptor primary structure: comparison with insulin receptor suggests structural determinants that define functional specificity," *EMBO J.*, (1986) 5(10):2503-2512.
Helene, C., "Specific regulation of gene expression by antisense, sense, and antigene nucleic acids," *Biochem. Biophys Acta* (1990) 1049:99-125.
Cooney, M., et al., "Site-specific oligonucleotide binding represses transcription of the human c-myc gene in vitro," *Science* 241(4864):456-459.
Haralambidis, J. et al. "The solid phase synthesis of oligonucleotides containing a 3'-peptide moiety," (1987) *Tetrahedron Lett.* 28(43):5199-5202.
Collins, J.F., "c-myc antisense oligonucleotides inhibit the colony-forming capacity of Colo 320 colonic carcinoma cells," *Journal of Clinical Investigation* (May 1992) 89(5):1523-7.
Wu, G Y. et al. Evidence for ed gene delivery to Hep G2 hepatoma cells in vitro. (1988) *Biochem.* 27:887-892.
Gali et al., "Chemical synthesis of *Escherichia coli* ST(h) analogues by regioselective disulfide bond formation: biological evaluation of an (111)In-DOTA-Phe(19)-ST(h) analogue for specific targeting of human colon cancers," Bioconjugate Chemistry (2002) 13:224-231.

* cited by examiner

FIGURE 5

| Compound | 1 μM ST Effect | 25 μM ST Effect |
|---|---|---|
| ST (4-14) Thr$^9$, Alb$^{13}$ | 110% | 101% |
| ST (4-14) Thr$^9$, Alb$^{12}$ | 90% | 89% |
| ST (4-14) Leu$^9$ amide | 65% | 65% |
| ST (4-14) Phe$^9$, Cys (Mob)$^{5,10}$ Mono | 91% | 39% |
| ST (4-14) Val$^9$ amide | 78% | 70% |
| ST (4-14) Phe$^9$ | 45% | 41% |
| ST (5-14) Ala$^9$, Tyr$^{15}$ | 78% | 79% |
| ST (5-14) Thr$^9$, Tyr$^{15}$ | 105% | 73% |
| ST (5-14) Leu$^9$, Tyr$^{15}$ | 109% | 80% |
| ST (4-14) N$^{ME}$Leu8 | 82% | 18% |
| ST (4-14) Ala$^9$ N$^{ME}$Ala$^{13}$ | 51% | 54% |
| ST (4-14) N$^{ME}$Ala9 | 105% | 33% |
| ST (4-14) Ala$^{9,17}$ | 85% | 80% |
| ST (5-14) Ala$^9$ | 106% | 62% |
| ST (6-14) Mpr$^5$ Ala$^9$ Carba$^{5,10}$ | 69% | 69% |
| ST (5-14) Ala$^{9,17}$ | 87% | 61% |

```
SEQUENCE LISTING

<160> NUMBER OF SEQ ID NOS: 31

<210> SEQ ID NO 1
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: SITE
<222> LOCATION: (2)..(2)
<223> OTHER INFORMATION: X = homocysteine
<220> FEATURE:
<221> NAME/KEY: SITE
<222> LOCATION: (10)..(10)
<223> OTHER INFORMATION: X = Alanine covalently bound to homocysteine
      via CH2-S bond between side chains

<400> SEQUENCE: 1

Cys Xaa Glu Leu Ala Cys Asn Pro Ala Xaa
1               5                   10

<210> SEQ ID NO 2
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: SITE
<222> LOCATION: (5)..(5)
<223> OTHER INFORMATION: X = Alanine covalently bound to homocysteine
      via CH2-S bond between side chains

<400> SEQUENCE: 2
```

```
Cys Glu Leu Ala Xaa Asn Pro Ala Cys
1               5
```

<210> SEQ ID NO 3
<211> LENGTH: 10
<212> TYPE: PRT
<213> ORGANISM: Artificial Sequence
<220> FEATURE:
<223> OTHER INFORMATION: synthetic sequence

<400> SEQUENCE: 3

```
Cys Cys Glu Leu Ala Cys Asn Pro Ala Cys
1               5                   10
```

<210> SEQ ID NO 4
<211> LENGTH: 13
<212> TYPE: PRT
<213> ORGANISM: Artificial Sequence
<220> FEATURE:
<223> OTHER INFORMATION: synthetic sequence

<400> SEQUENCE: 4

```
Cys Cys Glu Leu Ala Cys Asn Pro Ala Cys Thr Gly Ala
1               5                   10
```

<210> SEQ ID NO 5
<211> LENGTH: 11
<212> TYPE: PRT
<213> ORGANISM: Artificial Sequence
<220> FEATURE:
<223> OTHER INFORMATION: synthetic sequence
<220> FEATURE:
<221> NAME/KEY: SITE
<222> LOCATION: (2)..(2)
<223> OTHER INFORMATION: X = Cysteine(S-acetamidomethyl)
<220> FEATURE:
<221> NAME/KEY: SITE
<222> LOCATION: (7)..(7)
<223> OTHER INFORMATION: X = Cysteine(S-acetamidomethyl)

<400> SEQUENCE: 5

```
Tyr Xaa Cys Glu Leu Phe Xaa Asn Pro Ala Cys
1               5                   10
```

<210> SEQ ID NO 6
<211> LENGTH: 11
<212> TYPE: PRT
<213> ORGANISM: Artificial Sequence
<220> FEATURE:
<223> OTHER INFORMATION: synthetic sequence

<400> SEQUENCE: 6

```
Tyr Cys Cys Glu Leu Ala Cys Asn Pro Ala Cys
1               5                   10
```

<210> SEQ ID NO 7
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: SITE
<222> LOCATION: (5)..(5)
<223> OTHER INFORMATION: X = Cysteine(S-methoxybenzyl) or Cysteine(S-acetamidomethyl)
<220> FEATURE:
<221> NAME/KEY: SITE
<222> LOCATION: (13)..(13)
<223> OTHER INFORMATION: X = Cysteine(S-methoxybenzyl) or Cysteine(S- acetamidomethyl)

<400> SEQUENCE: 7

Cys Cys Glu Leu Xaa Cys Asn Pro Ala Cys Ala Gly Xaa
1               5                   10

<210> SEQ ID NO 8
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: SITE
<222> LOCATION: (1)..(1)
<223> OTHER INFORMATION: X = Alanine covalently bound to homocysteine
      via CH2-S bond between side chains
<220> FEATURE:
<221> NAME/KEY: SITE
<222> LOCATION: (2)..(2)
<223> OTHER INFORMATION: X = Cysteine(S-acetamidomethyl)
<220> FEATURE:
<221> NAME/KEY: SITE
<222> LOCATION: (6)..(6)
<223> OTHER INFORMATION: X = homocysteine
<220> FEATURE:
<221> NAME/KEY: SITE
<222> LOCATION: (10)..(10)
<223> OTHER INFORMATION: X = Cysteine(S-acetamidomethyl)

<400> SEQUENCE: 8

Xaa Xaa Glu Leu Ala Xaa Asn Pro Ala Xaa
1               5                   10

<210> SEQ ID NO 9
<211> LENGTH: 5
<212> TYPE: PRT
<213> ORGANISM: Artificial Sequence
<220> FEATURE:
<223> OTHER INFORMATION: synthetic sequence

<400> SEQUENCE: 9

Ser Ser Ser Asn Tyr
1               5

<210> SEQ ID NO 10
<211> LENGTH: 6
<212> TYPE: PRT
<213> ORGANISM: Artificial Sequence
<220> FEATURE:
<223> OTHER INFORMATION: synthetic sequence

<400> SEQUENCE: 10

Ser Ser Asp Trp Asp Tyr
1               5

<210> SEQ ID NO 11
<211> LENGTH: 8
<212> TYPE: PRT
<213> ORGANISM: Artificial Sequence
<220> FEATURE:
<223> OTHER INFORMATION: synthetic sequence

<400> SEQUENCE: 11

Asn Pro Ala Ala Ala Gly Cys Tyr
1               5

<210> SEQ ID NO 12
<211> LENGTH: 4

<212> TYPE: PRT
<213> ORGANISM: Artificial Sequence
<220> FEATURE:
<223> OTHER INFORMATION: synthetic amino acid modification

<400> SEQUENCE: 12

Asn Thr Phe Tyr
1

<210> SEQ ID NO 13
<211> LENGTH: 18
<212> TYPE: PRT
<213> ORGANISM: Escherichia coli

<400> SEQUENCE: 13

Asn Thr Phe Tyr Cys Cys Glu Leu Cys Cys Asn Pro Ala Cys Ala Gly
1 5 10 15

Cys Tyr

<210> SEQ ID NO 14
<211> LENGTH: 19
<212> TYPE: PRT
<213> ORGANISM: Escherichia coli

<400> SEQUENCE: 14

Ser Ser Ser Asn Tyr Cys Cys Glu Leu Cys Cys Asn Pro Ala Cys Thr
1 5 10 15

Gly Cys Tyr

<210> SEQ ID NO 15
<211> LENGTH: 20
<212> TYPE: PRT
<213> ORGANISM: Yersinia pestis

<400> SEQUENCE: 15

Ser Ser Asp Trp Asp Tyr Cys Cys Asp Leu Cys Cys Asn Pro Ala Cys
1 5 10 15

Ala Gly Cys Tyr
20

<210> SEQ ID NO 16
<211> LENGTH: 17
<212> TYPE: PRT
<213> ORGANISM: Vibrio cholerae

<400> SEQUENCE: 16

Ile Asp Cys Cys Glu Ile Cys Cys Asn Pro Ala Cys Phe Gly Cys Leu
1 5 10 15

Asn

<210> SEQ ID NO 17
<211> LENGTH: 15
<212> TYPE: PRT
<213> ORGANISM: Homo sapiens

<400> SEQUENCE: 17

Pro Asn Thr Cys Glu Ile Cys Ala Tyr Ala Ala Cys Thr Gly Cys
1 5 10 15

<210> SEQ ID NO 18
<211> LENGTH: 15
<212> TYPE: PRT
<213> ORGANISM: Homo sapiens

```
<400> SEQUENCE: 18

Gln Glu Asp Cys Glu Ile Cys Ile Asn Val Ala Cys Thr Gly Cys
1               5                   10                  15

<210> SEQ ID NO 19
<211> LENGTH: 13
<212> TYPE: PRT
<213> ORGANISM: Artificial Sequence
<220> FEATURE:
<223> OTHER INFORMATION: GCC agonist 1

<400> SEQUENCE: 19

Cys Cys Glu Leu Ala Cys Asn Pro Ala Cys Ala Gly Ala
1               5                   10

<210> SEQ ID NO 20
<211> LENGTH: 11
<212> TYPE: PRT
<213> ORGANISM: Artificial Sequence
<220> FEATURE:
<223> OTHER INFORMATION: GCC agonist 2
<220> FEATURE:
<221> NAME/KEY: MOD_RES
<222> LOCATION: (6)..(6)
<223> OTHER INFORMATION: N-METHYLATION

<400> SEQUENCE: 20

Tyr Cys Cys Glu Leu Leu Cys Asn Pro Ala Cys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: GCC agonist 3
<220> FEATURE:
<221> NAME/KEY: MOD_RES
<222> LOCATION: (6)..(6)
<223> OTHER INFORMATION: N-METHYLATION

<400> SEQUENCE: 21

Tyr Cys Cys Glu Leu Ala Cys Asn Pro Ala Cys Ala Gly Ala
1               5                   10

<210> SEQ ID NO 22
<211> LENGTH: 14
<212> TYPE: PRT
<213> ORGANISM: Artificial Sequence
<220> FEATURE:
<223> OTHER INFORMATION: GCC agonist 4
<220> FEATURE:
<221> NAME/KEY: MOD_RES
<222> LOCATION: (2)..(2)
<223> OTHER INFORMATION: BLOCKED
<220> FEATURE:
<221> NAME/KEY: MOD_RES
<222> LOCATION: (7)..(7)
<223> OTHER INFORMATION: BLOCKED

<400> SEQUENCE: 22

Tyr Cys Cys Glu Leu Phe Cys Asn Pro Ala Cys Ala Gly Ala
1               5                   10

<210> SEQ ID NO 23
<211> LENGTH: 11
<212> TYPE: PRT
<213> ORGANISM: Artificial Sequence
```

```
<220> FEATURE:
<223> OTHER INFORMATION: GCC agonist 5

<400> SEQUENCE: 23

Tyr Cys Cys Glu Leu Phe Cys Asn Pro Ala Cys
1               5                   10

<210> SEQ ID NO 24
<211> LENGTH: 11
<212> TYPE: PRT
<213> ORGANISM: Artificial Sequence
<220> FEATURE:
<223> OTHER INFORMATION: GCC agonist 6
<220> FEATURE:
<221> NAME/KEY: MOD_RES
<222> LOCATION: (6)..(6)
<223> OTHER INFORMATION: METHYLATION, MeVal

<400> SEQUENCE: 24

Tyr Cys Cys Glu Leu Val Cys Asn Pro Ala Cys
1               5                   10

<210> SEQ ID NO 25
<211> LENGTH: 11
<212> TYPE: PRT
<213> ORGANISM: Artificial Sequence
<220> FEATURE:
<223> OTHER INFORMATION: GCC agonist 7

<400> SEQUENCE: 25

Cys Cys Glu Leu Ala Cys Asn Pro Ala Cys Tyr
1               5                   10

<210> SEQ ID NO 26
<211> LENGTH: 11
<212> TYPE: PRT
<213> ORGANISM: Artificial Sequence
<220> FEATURE:
<223> OTHER INFORMATION: GCC agonist 8

<400> SEQUENCE: 26

Cys Cys Glu Leu Thr Cys Asn Pro Ala Cys Tyr
1               5                   10

<210> SEQ ID NO 27
<211> LENGTH: 11
<212> TYPE: PRT
<213> ORGANISM: Artificial Sequence
<220> FEATURE:
<223> OTHER INFORMATION: GCC agonist 9
<220> FEATURE:
<221> NAME/KEY: MOD_RES
<222> LOCATION: (10)..(10)
<223> OTHER INFORMATION: X= Aib

<400> SEQUENCE: 27

Tyr Cys Cys Glu Leu Thr Cys Asn Pro Xaa Cys
1               5                   10

<210> SEQ ID NO 28
<211> LENGTH: 11
<212> TYPE: PRT
<213> ORGANISM: Artificial Sequence
<220> FEATURE:
<223> OTHER INFORMATION: GCC agonist 10
<220> FEATURE:
<221> NAME/KEY: MOD_RES
<222> LOCATION: (9)..(9)
<223> OTHER INFORMATION: Aib
```

```
<400> SEQUENCE: 28

Tyr Cys Cys Glu Leu Thr Cys Asn Xaa Ala Cys
1               5                   10

<210> SEQ ID NO 29
<211> LENGTH: 13
<212> TYPE: PRT
<213> ORGANISM: Artificial Sequence
<220> FEATURE:
<223> OTHER INFORMATION: GCC agonist 11

<400> SEQUENCE: 29

Tyr Cys Cys Cys Glu Leu Leu Cys Asn Pro Ala Cys Tyr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: GCC agonist 12
<220> FEATURE:
<221> NAME/KEY: MOD_RES
<222> LOCATION: (10)..(10)
<223> OTHER INFORMATION: X= Alanine with N-METHYLATION

<400> SEQUENCE: 30

Tyr Cys Cys Glu Leu Ala Cys Asn Pro Xaa Cys
1               5                   10

<210> SEQ ID NO 31
<211> LENGTH: 8
<212> TYPE: PRT
<213> ORGANISM: Artificial Sequence
<220> FEATURE:
<223> OTHER INFORMATION: GCC agonist 13
<220> FEATURE:
<221> NAME/KEY: MOD_RES
<222> LOCATION: (1)..(1)
<223> OTHER INFORMATION: X= Cysteine modified with mercaptopropionic
      acid linked to residue 4.
<220> FEATURE:
<221> NAME/KEY: MOD_RES
<222> LOCATION: (4)..(4)
<223> OTHER INFORMATION: X= Alanine with linkage to residue 1.

<400> SEQUENCE: 31

Xaa Glu Leu Xaa Asn Pro Ala Cys
1               5
```

GUANYLYLCYCLASE C LIGANDS

CROSS-REFERENCE TO RELATED APPLICATION

This application is a U.S. Divisional Application filing of U.S. patent application Ser. No. 11/166,592, filed Jun. 24, 2005, issued Oct. 22, 2013 as U.S. Pat. No. 8,563,682, which claims priority to U.S. Provisional Application No. 60/583,039, filed Jun. 25, 2004, and which is incorporated herein by reference in its entirety.

FIELD OF THE INVENTION

The present invention relates to peptides and peptide analogues bind to the cellular receptor protein guanylyl cyclase C (GCC). In some embodiments, the peptides and peptide analogues are agonists and activate the signaling pathway that is activated by the binding of the natural GCC ligands to GCC. In some embodiments, the peptides and peptide analogues block binding of natural ligands of GCC but do not activate the signaling pathway activated by the binding of the natural GCC ligands to GCC.

BACKGROUND OF THE INVENTION

Gastrointestinal malignancies, including adenocarcinoma of the esophagus, stomach, colon, and rectum, are a leading cause of cancer and cancer-related mortality worldwide. GC-C is a transmembrane receptor expressed only on the apical membranes of intestinal enterocytes in normal, healthy adults and by primary and metastatic tumor cells of gastric, esophageal and colorectal adenocarcinoma. Conzelmann, M., et al., Cytokeratin 20 and guanylyl cyclase C mRNA is largely present in lymph node and liver specimens of colorectal cancer patients. Int J Cancer, 2003. 107(4): p. 617-28; Cagir, B., et al., Guanylyl cyclase C messenger RNA is a biomarker for recurrent stage II colorectal cancer. Ann Intern Med, 1999. 131(11): p. 805-12; Bustin, S. A., et al., Quantification of cytokeratin 20, carcinoembryonic antigen and guanylyl cyclase C mRNA levels in lymph nodes may not predict treatment failure in colorectal cancer patients. Int J Cancer, 2004. 108(3): p. 412-7; Pearlman, J. M., et al., A splice variant of the transcript for guanylyl cyclase C is expressed in human colon and colorectal cancer cells. Dig Dis Sci, 2000. 45(2): p. 298-305; Waldman, S. A., et al., Use of guanylyl cyclase C for detecting micrometastases in lymph nodes of patients with colon cancer. Dis Colon Rectum, 1998. 41(3): p. 310-5; Salto-Tellez, M., et al., Intrinsic variability in the detection of micrometastases in lymph nodes for re-staging of colorectal cancer. effect of individual markers and tissue samples. Eur J Cancer, 2003. 39(9): p. 1234-41; Chen, G., et al., Detection of occult metastasis in lymph nodes from colorectal cancer patients: a multiple-marker reverse transcriptase-polymerase chain reaction study. Dis Colon Rectum, 2004. 47(5): p. 679-86; Notarnicola, M., et al., K-ras and p53 mutations in DNA extracted from colonic epithelial cells exfoliated in faeces of patients with colorectal cancer. Dig Liver Dis, 2000. 32(2): p. 131-6; Hugues, M., et al., Identification and characterization of a new family of high-affinity receptors for Escherichia coli heat-stable enterotoxin in rat intestinal membranes. Biochemistry, 1991. 30(44): p. 10738-45; Carrithers, S. L., et al., Escherichia coli heat-stable enterotoxin receptors. A novel marker for colorectal tumors. Dis Colon Rectum, 1996. 39(2): p. 171-81; Carrithers, S. L., et al., Guanylyl cyclase C is a selective marker for metastatic colorectal tumors in human extraintestinal tissues. Proc Natl Acad Sci USA, 1996. 93(25): p. 14827-32; Carrithers, S. L., et al., Escherichia coli heat-stable toxin receptors in human colonic tumors. Gastroenterology, 1994. 107(6): p. 1653-61; Bustin, S. A., et al., Detection of cytokeratins 19/20 and guanylyl cyclase C in peripheral blood of colorectal cancer patients. Br J Cancer, 1999. 79(11-12): p. 1813-20; Pitari, G. M., et al., Guanylyl cyclase C agonists regulate progression through the cell cycle of human colon carcinoma cells. Proc Natl Acad Sci USA, 2001. 98(14): p. 7846-51; Tien, Y. W., et al., Simultaneous detection of colonic epithelial cells in portal venous and peripheral blood during colorectal cancer surgery. Dis Colon Rectum, 2002. 45(1): p. 23-9; Park, J., et al., Ectopic expression of guanylyl cyclase C in adenocarcinomas of the esophagus and stomach. Cancer Epidemiol Biomarkers Prev, 2002. 11(8): p. 739-44; Pitari, G. M., et al., Bacterial enterotoxins are associated with resistance to colon cancer. Proc Natl Acad Sci USA, 2003. 100(5): p. 2695-9; Vlems, F. A., et al., Investigations for a multi-marker RT-PCR to improve sensitivity of disseminated tumor cell detection. Anticancer Res, 2003. 23(1A): p. 179-86; Tien, Y. W., et al., The role of gelatinase in hepatic metastasis of colorectal cancer. Clin Cancer Res, 2003. 9(13): p. 4891-6; Chen, W. S., et al., Impact of Circulating Free Tumor Cells in the Peripheral Blood of Colorectal Cancer Patients during Laparoscopic Surgery. World J Surg, 2004; and Tien, Y. W., et al., Intravasation-Related Metastatic Factors in Colorectal Cancer. Tumour Biol, 2004. 25(1-2): p. 48-55, which are each incorporated herein by reference.

GCC has been identified previously as a specific marker and target for GI malignancies. Identification of the presence of GCC in ectopic sites, for example lymph nodes or blood, can be used as a marker to identify the presence of occult micrometastases of esophageal, gastric, colonic, or rectal cancers. One method to detect the presence of GCC is to quantify the amount of binding of a natural ligand of GCC, such as ST, in tissues. Also, GCC appears to be a highly-specific target to which can be directed novel imaging and therapeutic agents to treat metastatic esophageal, gastric, colonic, and rectal cancers. Indeed, diagnostic or therapeutic agents can be targeted to GCC-expressing tumors by their conjugation to GCC ligands such as ST.

U.S. Pat. No. 5,518,888 issued May 21, 1996 to Waldman, PCT application PCT/US94/12232 filed Oct. 26, 1994, U.S. application Ser. No. 08/467,920 filed Jun. 6, 1995, and U.S. application Ser. No. 08/583,447 filed Jan. 5, 1996, which are each incorporated herein by reference, disclose that metastasized colorectal tumors can be targeted for delivery of active compounds by targeting ST receptors (also referred to as guanylin cyclase C or GCC). The presence of ST receptors on cells outside of the intestinal tract as a marker for colorectal cancer allows for the screening, identification and treatment of individuals with metastasized colorectal tumors. ST receptors may also be used to target delivery of gene therapeutics and antisense compounds to colorectal cells.

U.S. Pat. No. 5,601,990 issued Feb. 11, 1997 to Waldman, PCT application PCT/US94/12232 filed Oct. 26, 1994, and PCT application PCT/US97/07467 filed May 2, 1997, which are each incorporated herein by reference, disclose that detection of evidence of expression of ST receptors in samples of tissue and body fluid from outside the intestinal track indicate metastasized colorectal cancer.

United States Patent Application Publication No. 20010029019 published Oct. 11, 2001, which is each incorporated herein by reference, discloses that primary and metastasized stomach and esophageal cancer tumors can be targeted for delivery of active compounds by targeting GCC. GCC serves as a marker for primary and metastasized stomach and esophageal cancer and allows for the screening, identification and treatment of individuals with primary and metastasized stomach and esophageal cancer. GCC is also be used to target delivery of gene therapeutics and antisense compounds to primary and metastasized stomach and esophageal cancer.

GCC regulates the balance of proliferation and differentiation of the epithelium in intestine. The intestinal epithelium is dynamic, with a well-defined vertical axis extending from the crypt depths, in the wall of the intestine, to the tips of villi which project out into the lumen of the intestine. Epithelial cells are "born" at the bottom of crypts as daughter cells produced by intestinal stem cells. These daughter cells continue to divide (proliferate) and their progeny migrate up the wall of the crypt toward the tip of the villus. Along this migration, the cells shift from proliferation to differentiation to become fully-functional mature enterocytes with the capacity to perform the normal functions of the gut including digestion, absorption and secretion. Once at the tip, these cells slough off into the lumen of the intestine and die. Thus, the intestinal epithelium turns over ~every three days. GCC and its endogenous ligands appear to be one of the factors that shifts epithelial cells from proliferation to differentiation along the crypt-villus axis. Indeed, GCC ligands inhibit the proliferation of these cells and change their gene expression pattern to a more terminally-differentiated state.

The GC-C protein has not been detected in any non-cancerous tissue outside of the intestine and is only found on tumors of gastrointestinal origin. Of particular importance to this proposal, the detection of GC-C mRNA has not been reported in any colorectal cancer metastatic tissues, i.e. non-colorectal tissue where metastatic colorectal cancer is often detected. For normal individuals, the presence of GC-C mRNA has not been described in the published literature for the metastatic sites of colorectal, gastric or esophageal cancer (i.e., liver, lung, bone, brain), but it has been described in the proximal tubule cells of the kidney (Sindice, A., et al., Guanylin, uroguanylin, and heat-stable enterotoxin activate guanylate cyclase C and/or a pertussis toxin-sensitive G protein in human proximal tubule cells. J Biol Chem, 2002. 277(20): p. 17758-64, which is incorporated herein by reference), exocrine duct cells of the pancreas (Kulaksiz, H., et al., Guanylin in the human pancreas: a novel luminocrine regulatory pathway of electrolyte secretion via cGMP and CFTR in the ductal system. Histochem Cell Biol, 2001. 115(2): p. 131-45, which is incorporated herein by reference), submandibular glands (Kulaksiz, H., et al., Guanylin and functional coupling proteins in the human salivary glands and gland tumors: expression, cellular localization, and target membrane domains. Am J Pathol, 2002. 161(2): p. 655-64, which is incorporated herein by reference), the bile duct (Kulaksiz, H., et al., Guanylin regulates chloride secretion in the human gallbladder via the bile fluid. Gastroenterology, 2004. 126(3): p. 732-40. which is incorporated herein by reference) and at trace levels in CD34+ stem cells (Fava, T. A., et al., Ectopic expression of guanylyl cyclase C in CD34+ progenitor cells in peripheral blood. J Clin Oncol, 2001. 19(19): p. 3951-9). A common theme for each of these anatomical locations, except CD34+ cells, is that GC-C is separated from the blood and lymphatic systems by tight junctions analogous to that found in the intestine.

Diarrheal diseases are the fourth leading cause of mortality worldwide, responsible for about 20 million deaths each year. Such diseases are the leading cause of pediatric mortality worldwide, particularly affecting children under 5 years of age. Further, diarrheal diseases are responsible for ~25% of the growth retardation observed in children raised in under-developed, compared to developed, nations. One major cause of diarrheal disease are organisms producing heat-stable enterotoxins (STs), a family of structurally-related peptides produced by different organisms including, but not limited to, *E. coli, Yersinia, Enterobacter*, and *Vibrio*. This family of structurally-related ST peptides is homologous to the endogenous peptides guanylin and uroguanylin produced in mammalian intestine. ST-producing organisms are a major cause of endemic diarrhea in under-developed countries, the leading cause of travelers' diarrhea, and the leading cause of diarrheal disease in agriculturally-important animal populations (scours) in developed and under-developed countries. It is estimated that the annual incidence of ST-induced diarrheal disease numbers in the billions in animals and humans. ST induces diarrhea by binding to GCC, which is selectively expressed in brush border membranes of intestinal epithelial cells and the presumed receptor for the endogenous ligands guanylin and uroguanylin. Interaction of ST, or the endogenous ligands guanylin and uroguanylin, with GCC activates that receptor resulting in the production of intracellular cyclic GMP. Cyclic GMP, through a signaling cascade induces the secretion of salt and water into the lumen of the intestine, resulting in diarrhea. It has been suggested that one function for the endogenous ligands guanylin and uroguanylin in normal physiology is the regulation of fluid and electrolyte homeostasis in intestine, and the hydration of intestinal contents (e.g. stool).

Over the past 20 to 30 years, attempts have been made to design ligands that antagonize GCC. Such a compound of the invention would be useful in the detection of GCC on cells, as a targeted diagnostic and therapeutic agent in cases of GI malignancies, and in the treatment of diarrheal diseases of animals and humans. Moreover, such a compound of the invention might have application in cases requiring intestinal adaptation, wherein the epithelium requires rapid regeneration following an insult, for example chemical or ischemic damage. Previous structure-function studies of GCC ligands were unrevealing with respect to the discriminating the structural determinants required for receptor binding from those required for agonist activation (e.g. cyclic GMP production).

There is a need for compounds that bind to GCC and activate the GCC signal pathway and there is a need for compounds which bind to GCC but do not activate the GCC signal pathway.

SUMMARY OF THE INVENTION

The present invention provides compounds that bind to GCC. Endogenous ligands of GCC and enterotoxins known to bind to GCC are characterized as having two disulphide bonds (forming Loop B and Loop C) or three disulphide bonds (forming Loop A, Loop B and Loop C). The compounds of the invention have either Loop A or Loop B but not both. The compounds of the invention can be conjugated to active agents such as detectable labels, imaging agents or therapeutic compounds and used to bind to GCC which is a cancer marker for metastasized colorectal cancer and for primary and metastasized esophageal and stomach cancer.

Some compounds of the invention that have Loop A are GCC compound of the inventions. They bind to GCC but do not activate the GCC pathway. Those are useful to treat undesirable activation of the GCC pathway such as that associated with diarrhea such as travelers diarrhea brought on by exposure to bacterial enterotoxin. Some aspects of the present invention relate to these compounds and to methods of using them.

Some compounds of the invention that have Loop B are GCC compound of the inventions, some are GCC agonists and some are GCC prodrugs which are GCC compound of the inventions but when processed in vivo are converted to agonists. Some compounds that have Loop B are GCC compound of the inventions; they bind to GCC but do not activate the GCC pathway. They are useful to treat undesirable activation of the GCC pathway such as that associated with diarrhea such as travelers diarrhea brought on by exposure to bacterial enterotoxin. Some aspects of the present invention relate to these compounds and to methods of using them.

Some compounds that have Loop B are GCC agonists; they bind to GCC and activate the GCC pathway. They are useful to treat cancer, particularly metastasized colorectal cancer and primary and metastasized esophageal and stomach cancer, as well as prevent metastasis and activate the GCC pathway to induce defecation such when an individual is constipated or impacted. Some aspects of the present invention relate to these compounds and to methods of using them.

Some compounds that have Loop B are GCC prodrugs. These compounds bind to GCC but do not activate the GCC pathway when intact. When these compounds are processed, such as when processed in vivo by endogenous or administered enzymes that degrade its C terminal residues, they become GCC agonists. These compounds are useful to treat cancer, particularly metastasized colorectal cancer and primary and metastasized esophageal and stomach cancer, as well as prevent metastasis and activate the GCC pathway to induce defecation such when an individual is constipated or impacted. They have the advantage of having delayed activity and controllable conversion by using enzyme inhibitors to prevent the degradation. When used in conjunction with enzyme inhibitors that prevent degradation, their conversion can be controlled or prevented whereby they act as compound of the inventions which make them useful to inhibit GCC activation The present invention relates to compounds having a structure according to formula (I)

$$R1-R2-R3-R4-R5-R6-R7 \quad (I)$$

wherein:

R1 is combination of 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof;

R2 is a natural amino acid, blocked amino acid, synthetic amino acid, derivatized amino acid; an amino acid mimetic;

R3 is a natural amino acid, blocked amino acid, synthetic amino acid, derivatized amino acid or amino acid mimetic that crosslinks with R8;

R4 is one or two natural amino acids, one or two blocked amino acids, one or two synthetic amino acids, one or two derivatized amino acids, one or two amino acid mimetics, or a dipeptide mimetic or combinations thereof, wherein R4 forms a $3_{10}$-helix turn group linking R3 to R5;

R5 is a natural amino acid, blocked amino acid, synthetic amino acid, derivatized amino acid or amino acid mimetic that does not crosslink with R9

R6 is a natural amino acid, blocked amino acid, synthetic amino acid, derivatized amino acid, or amino acid mimetic;

R7 is one, two or three natural amino acids, one, two or three blocked amino acids, one, two or three amino acid mimetics, or a tripeptide mimetic or combinations thereof, wherein R7 forms a beta turn group linking R6 to R8

R8 is a natural amino acid, blocked amino acid, synthetic amino acid, derivatized amino acid or amino acid mimetic that crosslinks with R3;

R9 is a combination of 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof that does not crosslink to R5; provided the structure is not:

C-hC-E-L-A-C-N-P-A-X; hC;
C-E-L-A-X-N-P-A-C;
C-C-E-L-A-C-N-P-A-C;
C-C-E-L-A-C-N-P-A-C-T-G-A;
Y-Ca-C-E-L-F-Ca-N-P-A-C;
Y-C-C-E-L-mA-C-N-P-A-C;
Y-C-C-E-mL-A-C-N-P-A-C;
C-C-E-L-Cm-C-N-P-A-C-A-G-Cm;
C-C-E-L-Ca-C-N-P-A-C-A-G-Ca; or
X-Ca-E-L-A-hC-N-P-A-Ca;

wherein hC is Homocysteine;

X is Alanine linked to hC via a covalent CH2-S bond between an Ala side chain and an hC side chain;

Cm is Cysteine(S-methoxybenzyl); and

Ca is Cysteine(S-acetamidomethyl).

The present invention also relates to compounds that are Loop A compound of the inventions. The present invention relates to compounds having Formula (II):

$$R201-R202-R203-R204-R205-R206-R207 \quad (II)$$

wherein:

R201 is absent or 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof;

R202 is absent, or is a natural amino acid, blocked amino acid, synthetic amino acid, derivatized amino acid or an amino acid mimetic which does not crosslink to any other amino acid, or is a natural amino acid, blocked amino acid, synthetic amino acid, derivatized amino acid or amino acid mimetic that crosslinks with R205 or 8206, wherein if R202 is absent or a natural amino acid, blocked amino acid, synthetic amino acid, derivatized amino acid or an amino acid mimetic which does not crosslink to any other amino acid then R203 is a natural amino acid, blocked amino acid, synthetic amino acid, derivatized amino acid or amino acid mimetic that crosslinks with R205 or R206;

R203 is absent, or is a natural amino acid, blocked amino acid, synthetic amino acid, derivatized amino acid or an amino acid mimetic which does not crosslink to any other amino acid, or if R202 is absent or is a natural amino acid, blocked amino acid, synthetic amino acid, derivatized amino acid or an amino acid mimetic which does not crosslink to any other amino acid then R203 is a natural amino acid, blocked amino acid, synthetic amino acid, derivatized amino acid or amino acid mimetic that crosslinks with R205 or R206;

R204 is one or two natural amino acids, one or two blocked amino acids, one or two synthetic amino acids, one or two derivatized amino acids, one or two amino acid mimetics, or a dipeptide mimetic or combinations thereof, wherein R204 forms a $3_{10}$-helix turn group linking R203 to R205;

R205 is absent, or is a natural amino acid, blocked amino acid, synthetic amino acid, derivatized amino acid or an amino acid mimetic which does not crosslink to any other amino acid, or if R206 is absent or is a natural amino acid, blocked amino acid, synthetic amino acid, derivatized amino acid or an amino acid mimetic which does not crosslink to any other amino acid then R205 is a natural amino acid, blocked amino acid, synthetic amino acid, derivatized amino acid or amino acid mimetic that crosslinks with R202 or R203;

R206 is absent, or is a natural amino acid, blocked amino acid, synthetic amino acid, derivatized amino acid or an amino acid mimetic which does not crosslink to any other amino acid, or is a natural amino acid, blocked amino acid, synthetic amino acid, derivatized amino acid or amino acid mimetic that crosslinks with R202 or R203, wherein if R206 is absent or a natural amino acid, blocked amino acid, synthetic amino acid, derivatized amino acid or an amino acid mimetic which does not crosslink to any other amino acid then R205 is a natural amino acid, blocked amino acid, synthetic amino acid, derivatized amino acid or amino acid mimetic that crosslinks with R202 or R203; and R207 is absent or 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof.

The present invention also relates to compounds that are Loop B compounds. The present invention relates to compounds having Formula (III):

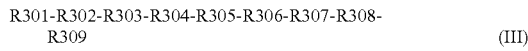
(III)

wherein:

R301 is combination of 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof;

R302 is a natural amino acid, blocked amino acid, synthetic amino acid, derivatized amino acid, or an amino acid mimetic wherein R302 may crosslink with R306;

R303 is a natural amino acid, blocked amino acid, synthetic amino acid, derivatized amino acid or amino acid mimetic that crosslinks with R308;

R304 is one or two natural amino acids, one or two blocked amino acids, one or two synthetic amino acids, one or two derivatized amino acids, one or two amino acid mimetics, or a dipeptide mimetic or combinations thereof, wherein R304 forms a $3_{10}$-helix turn group linking R303 to R305;

R305 is a natural amino acid, blocked amino acid, synthetic amino acid, derivatized amino acid or amino acid mimetic that does not crosslink with R309

R306 is a natural amino acid, blocked amino acid, synthetic amino acid, derivatized amino acid, or amino acid mimetic wherein R306 may crosslink with R302;

R307 is one, two or three natural amino acids, one, two or three blocked amino acids, one, two or three amino acid mimetics, or a tripeptide mimetic or combinations thereof, wherein R307 forms a beta turn group linking R306 to R308

R308 is a natural amino acid, blocked amino acid, synthetic amino acid, derivatized amino acid or amino acid mimetic that crosslinks with R303;

R309 is absent or 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof that does not crosslink to R305;

wherein the structure of the compounds is not:
SEQ. ID NO. 1: C-hC-E-L-A-C-N-P-A-X; hC;
SEQ. ID NO. 2: C-E-L-A-X-N-P-A-C;
SEQ. ID NO. 3: C-C-E-L-A-C-N-P-A-C;
SEQ. ID NO. 4: C-C-E-L-A-C-N-P-A-C-T-G-A;
SEQ. ID NO. 5: Y-Ca-C-E-L-F-Ca-N-P-A-C;
SEQ. ID NO. 6: Y-C-C-E-L-mA-C-N-P-A-C;
SEQ. ID NO. 6: Y-C-C-E-mL-A-C-N-P-A-C;
SEQ. ID NO. 7: C-C-E-L-Cm-C-N-P-A-C-A-G-Cm;
SEQ. ID NO. 7: C-C-E-L-Ca-C-N-P-A-C-A-G-Ca; or
SEQ. ID NO. 8: X-Ca-E-L-A-hC-N-P-A-Ca;
wherein
hC is Homocysteine;
X is Alanine linked to hC via a covalent CH2-S bond between an Ala side chain and an hC side chain;
Cm is Cysteine(S-methoxybenzyl); and
Ca is Cysteine(S-acetamidomethyl).

The present invention further relates to compounds having Formula (IV):

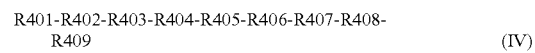
(IV)

wherein:

R401 is combination of 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof;

R402 is a natural amino acid, blocked amino acid, synthetic amino acid, derivatized amino acid, or an amino acid mimetic wherein R402 may crosslink with R406;

R403 is a natural amino acid, blocked amino acid, synthetic amino acid, derivatized amino acid or amino acid mimetic that crosslinks with R408;

R404 is one or two natural amino acids, one or two blocked amino acids, one or two synthetic amino acids, one or two derivatized amino acids, one or two amino acid mimetics, or a dipeptide mimetic or combinations thereof, wherein R404 forms a $3_{10}$-helix turn group linking R403 to R405;

R405 is a natural amino acid, blocked amino acid, synthetic amino acid, derivatized amino acid or amino acid mimetic that does not crosslink with R409

R406 is a natural amino acid, blocked amino acid, synthetic amino acid, derivatized amino acid, or amino acid mimetic wherein R406 may crosslink with R402;

R407 is one, two or three natural amino acids, one, two or three blocked amino acids, one, two or three amino acid mimetics, or a tripeptide mimetic or combinations thereof, wherein R407 forms a beta turn group linking R406 to R408

R408 is a natural amino acid, blocked amino acid, synthetic amino acid, derivatized amino acid or amino acid mimetic that crosslinks with R403;

R409 is absent;

wherein the structure of the compounds is not:
SEQ. ID NO. 3: C-hC-E-L-A-C-N-P-A-X; hC;
SEQ. ID NO. 2: C-E-L-A-X-N-P-A-C;
SEQ. ID NO. 3: C-C-E-L-A-C-N-P-A-C;
SEQ. ID NO. 5: Y-Ca-C-E-L-F-Ca-N-P-A-C;
SEQ. ID NO. 6: Y-C-C-E-L-mA-C-N-P-A-C;
SEQ. ID NO. 6: Y-C-C-E-mL-A-C-N-P-A-C;
SEQ. ID NO. 7: C-C-E-L-Cm-C-N-P-A-C-A-G-Cm;
SEQ. ID NO. 7: C-C-E-L-Ca-C-N-P-A-C-A-G-Ca;
SEQ. ID NO. 8: X-Ca-E-L-A-hC-N-P-A-Ca;

wherein hC is Homocysteine;

X is Alanine linked to hC via a covalent CH2-S bond between an Ala side chain and an hC side chain;

Cm is Cysteine(S-methoxybenzyl); and

Ca is Cysteine(S-acetamidomethyl).

The present invention also relates to compounds that are Loop B prodrugs. The present invention relates to compounds having Formula (V):

Formula (V):

R501-R502-R503-R504-R505-R506-R507-R508-R509 (V)

wherein:

R501 is combination of 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof;

R502 is a natural amino acid, blocked amino acid, synthetic amino acid, derivatized amino acid, or an amino acid mimetic wherein R502 may crosslink with R506;

R503 is a natural amino acid, blocked amino acid, synthetic amino acid, derivatized amino acid or amino acid mimetic that crosslinks with R508;

R504 is one or two natural amino acids, one or two blocked amino acids, one or two synthetic amino acids, one or two derivatized amino acids, one or two amino acid mimetics, or a dipeptide mimetic or combinations thereof, wherein R504 forms a $3_{10}$-helix turn group linking R503 to R505;

R505 is a natural amino acid, blocked amino acid, synthetic amino acid, derivatized amino acid or amino acid mimetic that does not crosslink with R509

R506 is a natural amino acid, blocked amino acid, synthetic amino acid, derivatized amino acid, or amino acid mimetic wherein R506 may crosslink with R502;

R507 is one, two or three natural amino acids, one, two or three blocked amino acids, one, two or three amino acid mimetics, or a tripeptide mimetic or combinations thereof, wherein R507 forms a beta turn group linking R506 to R508

R508 is a natural amino acid, blocked amino acid, synthetic amino acid, derivatized amino acid or amino acid mimetic that crosslinks with R503;

R509 is 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof that does not crosslink to R505;

wherein the compound is degradable in vivo and the structure of the compounds is not SEQ. ID NO. 4: C-C-E-L-A-C-N-P-A-C-T-G-A.

The present invention also relates to compounds that are Loop B compound of the inventions. The present invention relates to compounds having Formula (VI):

R601-R602-R603-R604-R605-R606-R607-R608-R609 (VI)

wherein:

R601 is combination of 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof;

R602 is a natural amino acid, blocked amino acid, synthetic amino acid, derivatized amino acid, or an amino acid mimetic wherein R602 may crosslink with R606;

R603 is a natural amino acid, blocked amino acid, synthetic amino acid, derivatized amino acid or amino acid mimetic that crosslinks with R608;

R604 is one or two natural amino acids, one or two blocked amino acids, one or two synthetic amino acids, one or two derivatized amino acids, one or two amino acid mimetics, or a dipeptide mimetic or combinations thereof, wherein R604 forms a $3_{10}$-helix turn group linking R603 to R605;

R605 is a natural amino acid, blocked amino acid, synthetic amino acid, derivatized amino acid or amino acid mimetic that does not crosslink with R609

R606 is a natural amino acid, blocked amino acid, synthetic amino acid, derivatized amino acid, or amino acid mimetic wherein R606 may crosslink with R602;

R607 is one, two or three natural amino acids, one, two or three blocked amino acids, one, two or three amino acid mimetics, or a tripeptide mimetic or combinations thereof, wherein R607 forms a beta turn group linking R606 to R608

R608 is a natural amino acid, blocked amino acid, synthetic amino acid, derivatized amino acid or amino acid mimetic that crosslinks with R603;

R609 is 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof that does not crosslink to R605 and is non-degradable in vivo.

The present invention further relates to conjugated compounds that comprise a compound of a formula selected from the group consisting of: Formula (I), Formula (II), Formula (III), Formula (IV), Formula (V), and Formula (VI), that is conjugated to an active moiety which may be a radionuclide, an enzyme, a fluorescent label, a metal chelating group, a chemiluminescent label, a bioluminescent label, a chemotherapeutic, a toxin, an inactive prodrug, a radiosensitizing agent, a photodynamic agent, a nucleic acid molecule or combinations thereof.

The present invention further relates to compositions comprising liposomes that comprise compounds of the invention, conjugated or unconjugated, in combination with an active agent selected from the group consisting of: a radionuclide, an enzyme, a fluorescent label, a metal chelating group, a chemiluminescent label, a bioluminescent label, a chemotherapeutic, a toxin, an inactive prodrug, a radiosensitizing agent, a photodynamic agent, a nucleic acid molecule or combinations thereof.

The present invention further relates to compositions that comprise compounds of the invention in combination with a chemotherapeutic, a toxin, or combinations thereof.

The present invention relates to methods of diagnosing cancer characterized by expression of GCC in an individual. The methods comprising the step of detecting GCC in an extraintestinal sample from an individual by contacting the sample or portions thereof with such compound and detecting the presence of the compound bound to the sample.

The present invention relates to methods of imaging cancer characterized by expression of GCC in an individual. The methods comprise the step of administering to the individual such a conjugated compound in which active moiety of the conjugated compound is a detectable label. The accumulation of the conjugated compound at a site on the individual's body is detected.

The present invention further relates to methods of treating cancer characterized by expression of GCC in an individual. The methods comprise the step of administering to the individual such a conjugated compound in which the active moiety kills or inhibits replication of cells to which it binds.

The present invention further relates to method of treating an individual who has enterotoxin mediated diarrhea or who is at risk of contracting enterotoxin mediated diarrhea. The methods comprise the step of administering to said individual a compound with a structure according to Formula (II) or Formula (VI).

The present invention further relates to method of treating an individual who has enterotoxin mediated diarrhea or who is at risk of contracting enterotoxin mediated diarrhea. The methods comprise the step of administering to said individual a compound with a structure according to Formula (I), Formula (III), Formula (IV) or Formula (V) under conditions such that the C terminal is not degradable such that the compound is converted to an agonist.

The present invention further relates to method of treating an individual who has cancer or who is at risk of developing cancer. The methods comprise the step of administering to said individual a compound with a structure according to Formula (I) Formula (III), Formula (IV) or Formula (V) under conditions such that the C terminal is degradable such that the compound is converted to an agonist. In some embodiments, the compounds are administered in combination with a chemotherapeutic agent or a toxin.

The present invention further relates to method of treating an individual who has cancer or who is at risk of developing cancer. The methods comprise the step of administering to said individual a compound with a structure according to Formula (II). In some embodiments, the compounds are administered in combination with a chemotherapeutic agent or a toxin.

BRIEF DESCRIPTION OF THE FIGURES

FIG. 5: A table containing raw data of the 16 different compound of the inventions at 1 microM and 25 microM

DETAILED DESCRIPTION OF PREFERRED EMBODIMENTS OF THE INVENTION

Definitions

Figure 1:
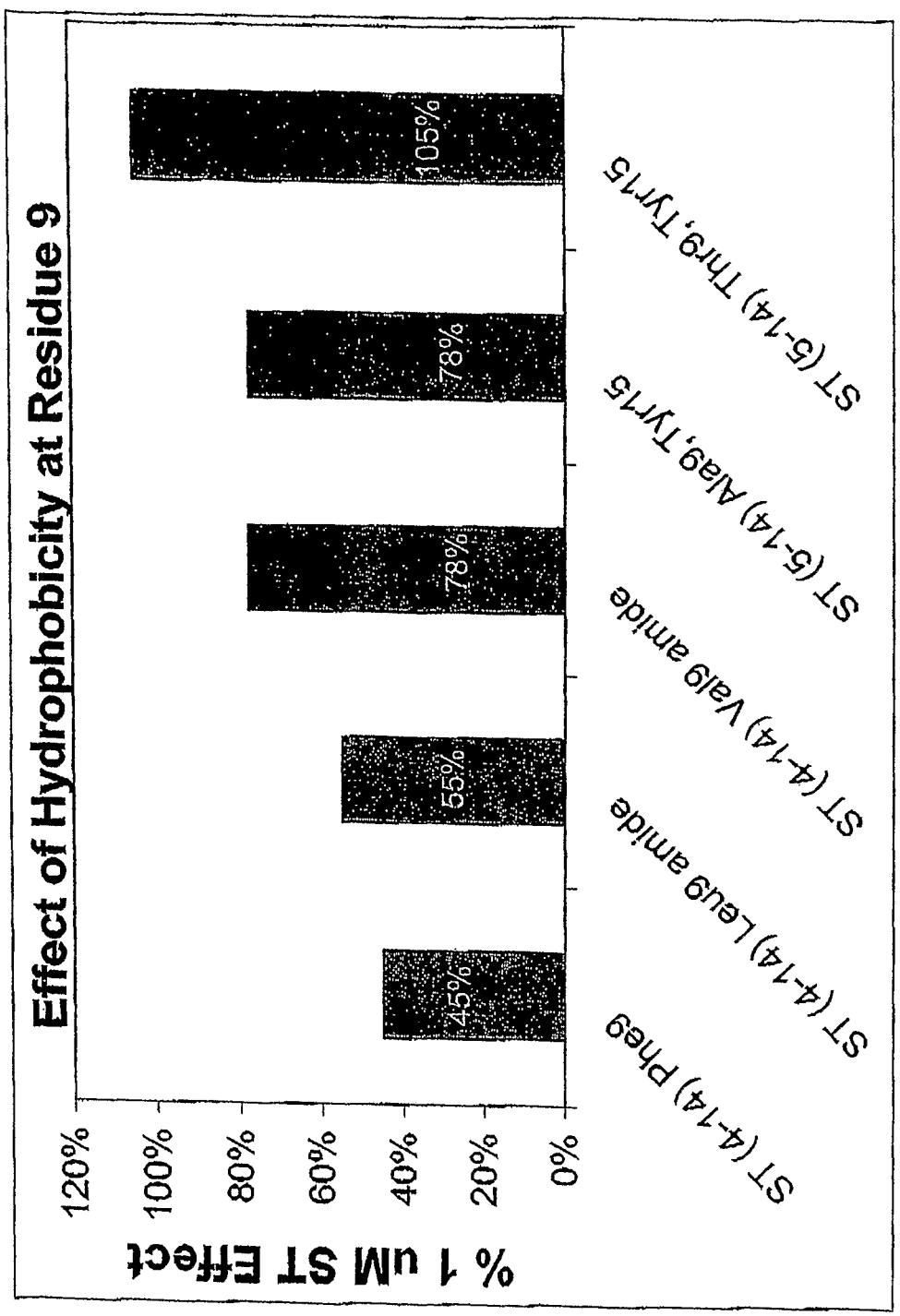
FIG. 1 show data: Effect of Hydrophobicity at Residue 9.
Figure 2:
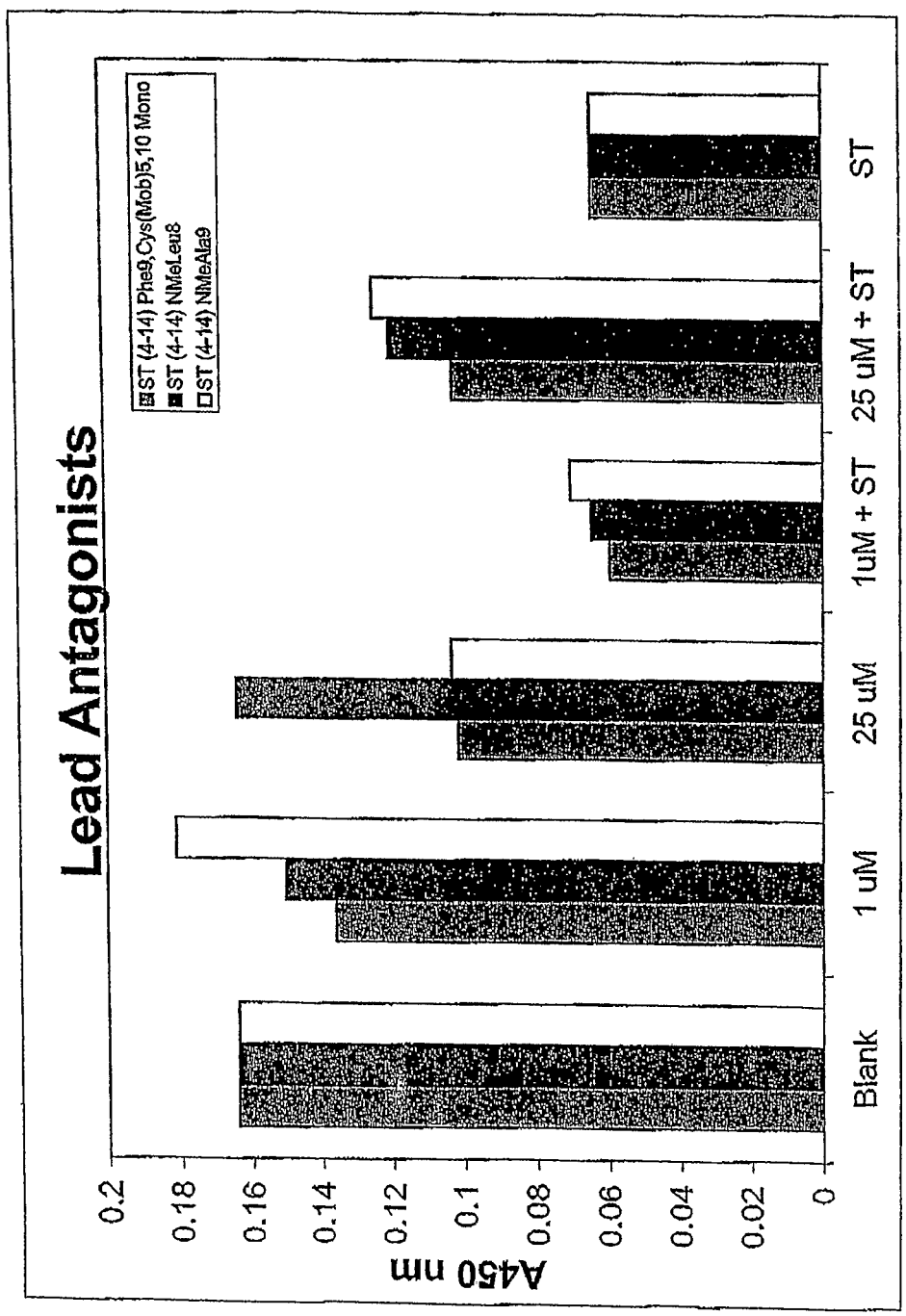
FIG. 2: Lead Compound of the inventions (comparing ST(4-14)Phe9,Cys(Mob)5,10Mono, ST(4-14)NMeLeu8 and ST(4-14)NMeAla9 at 1 and 25 microM with and without ST)
Figure 3:
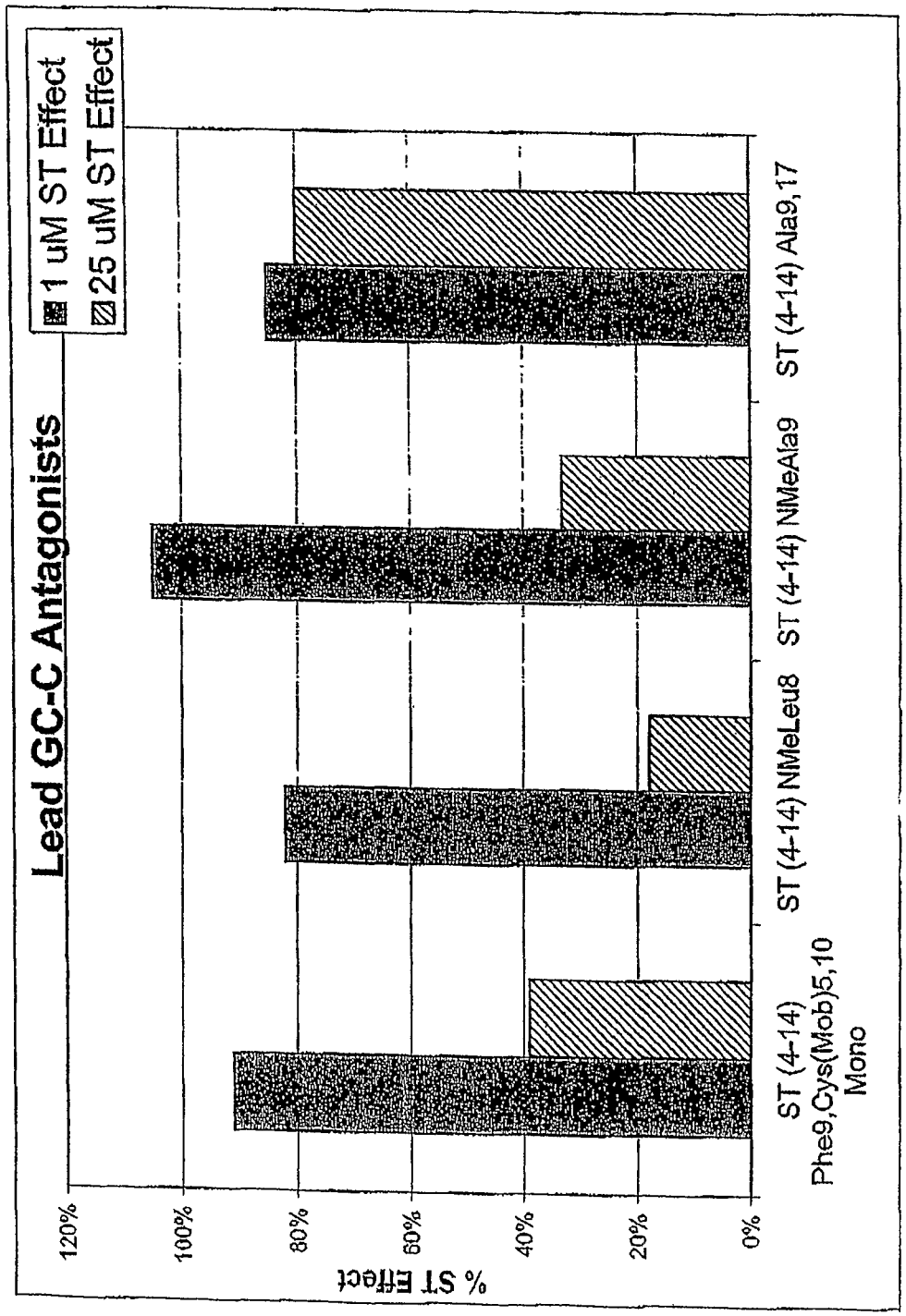
FIG. 3: Lead GC-C Compound of the inventions (comparing ST(4-14)Phe9,Cys(Mob)5,10Mono, ST(4-14) NMeLeu8, ST(4-14)NMeAla9 and ST(4-14) Ala-9,17 at 1 and 25 microM)
Figure 4:
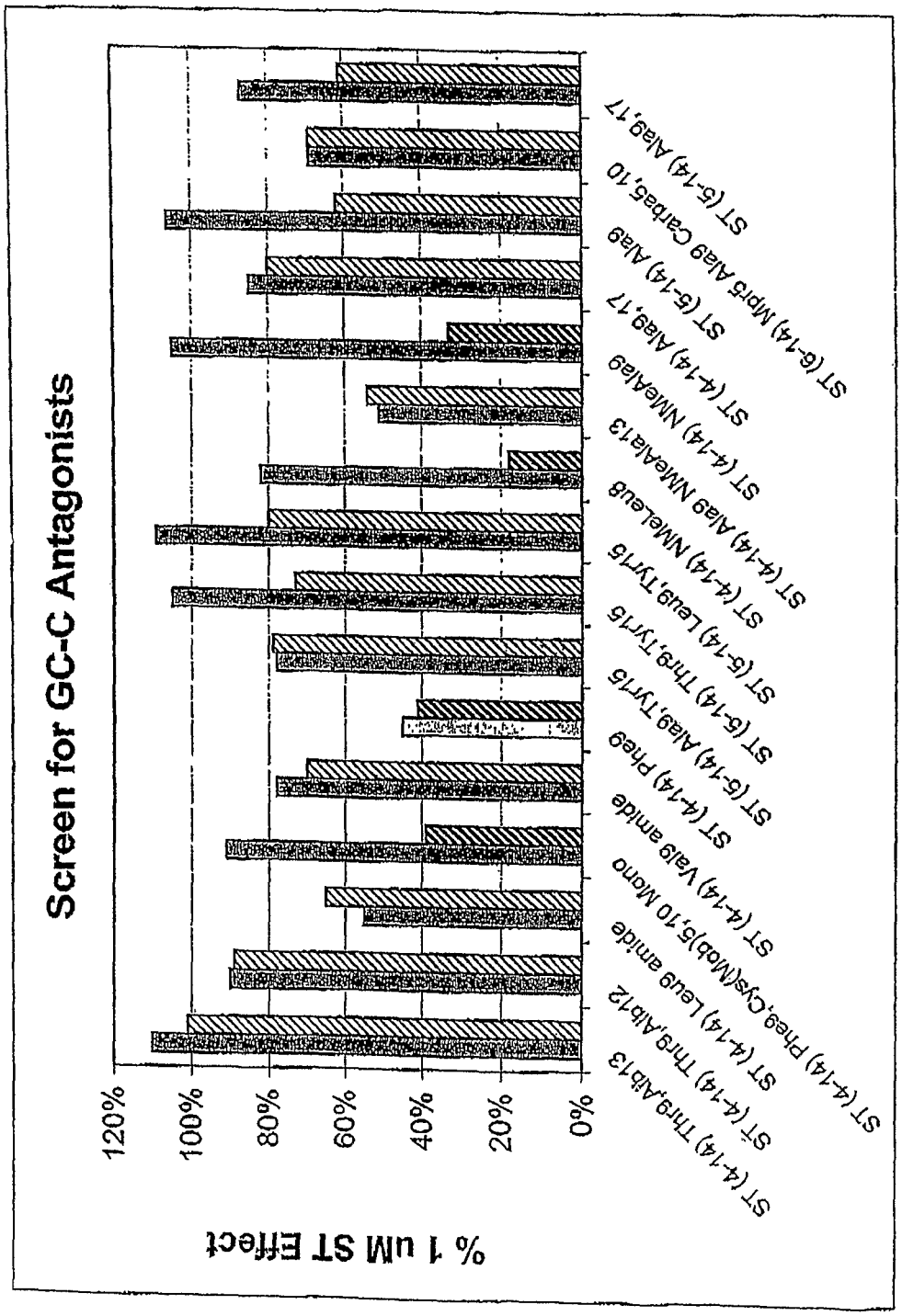
FIG. 4: Screen for GC-C Compound of the inventions (comparing 16 different compound of the inventions at 1 microM)
Figure 6:
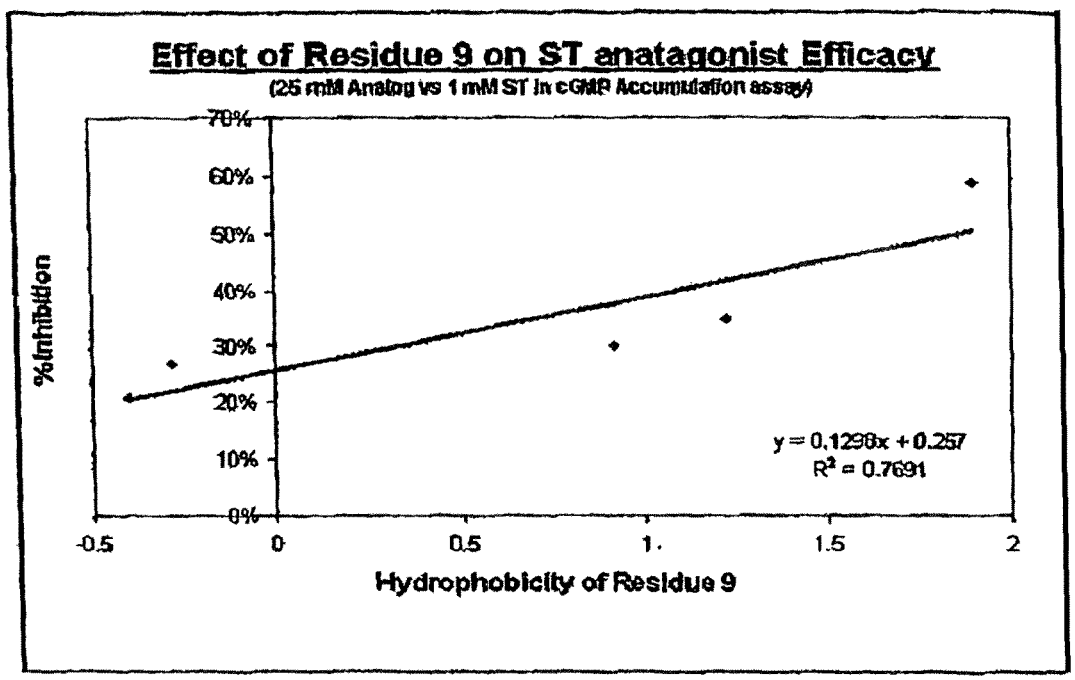
FIG. 6: Effect of residue 9 on ST antagonist efficacy.

As used herein, the following terms shall have the following meanings:

As used herein, the terms "antagonist," "antagonist compounds," "antagonists of the invention" is meant to refer to compounds which bind to GCC and block GCC binding to natural ligands but do not activate the GCC pathway.

As used herein, the terms "agonist," "agonist compounds," "agonists of the invention" is meant to refer to compounds which bind to GCC and block GCC binding to natural ligands and activate the GCC pathway.

As used herein, the term "natural ligands" is meant to refer to heat stabile enterotoxins as well as endogenously produced GCC ligands guanylin and uroguanylin.

As used herein, the term "active agent" is meant to refer to compounds that are therapeutic agents or imaging agents.

As used herein, the term "therapeutic agent" is meant to refer to chemotherapeutics, toxins, radiotherapeutics, targeting agents or radiosensitizing agents.

As used herein, the term "chemotherapeutic" is meant to refer to compounds that, when contacted with and/or incorporated into a cell, produce an effect on the cell including causing the death of the cell, inhibiting cell division or inducing differentiation.

As used herein, the term "toxin" is meant to refer to compounds that, when contacted with and/or incorporated into a cell, produce the death of the cell.

As used herein, the term "radiotherapeutic" is meant to refer to radionuclides which when contacted with and/or incorporated into a cell, produce the death of the cell.

As used herein, the term "targeting agent" is meant to refer compounds which can be bound by and or react with other compounds. Targeting agents may be used to deliver chemotherapeutics, toxins, enzymes, radiotherapeutics, antibodies or imaging agents to cells that have targeting agents associated with them and/or to convert or otherwise transform or enhance co-administered active agents. A targeting agent may include a moiety that constitutes a first agent that is localized to the cell which when contacted with a second agent either is converted to a third agent which has a desired activity or causes the conversion of the second agent into an agent with a desired activity. The result is the localized agent facilitates exposure of an agent with a desired activity to the cancer cell.

As used herein, the term "radiosensitizing agent" is meant to refer to agents which increase the susceptibility of cells to the damaging effects of ionizing radiation. A radiosensitizing agent permits lower doses of radiation to be administered and still provide a therapeutically effective dose.

As used herein, the term "imaging agent" is meant to refer to compounds which can be detected.

As used herein, the term "active moiety" is meant to refer to the portion of a conjugated compound that constitutes an active agent.

As used herein, the terms "conjugated compound" and "conjugated composition" are used interchangeably and meant to refer to a compound which comprises a compound of the invention as a GCC binding moiety and an active moiety. The conjugated compound is which is capable of binding to GCC. Conjugated compounds according to the present invention comprise a portion which constitutes compound of the invention and a portion which constitutes an active agent. Thus, conjugated compounds according to the present invention are capable of specifically binding to GCC and include a portion which is a therapeutic agent or imaging agent. Conjugated compositions may comprise linkers and/or molecules that serve as spacers between the moieties.

As used herein, the terms "linker", "linking agent", "conjugating agent", "coupling agent", "condensation reagent" and "bifunctional linker" are used interchangeably and are meant to refer to molecular groups which are used to attach the compound of the invention and the active agent to thus form the conjugated compound.

As used herein, the term "colorectal cancer" is meant to include the well-accepted medical definition that defines colorectal cancer as a medical condition characterized by cancer of cells of the intestinal tract below the small intestine (i.e. the large intestine (colon), including the cecum, ascending colon, transverse colon, descending colon, and sigmoid colon, and rectum). Additionally, as used herein, the term "colorectal cancer" is meant to further include medical conditions which are characterized by cancer of cells of the duodenum and small intestine (jejunum and ileum). The definition of colorectal cancer used herein is more expansive than the common medical definition but is provided as such since the cells of the duodenum and small intestine also contain GCC.

As used herein, the term "stomach cancer" is meant to include the well-accepted medical definition that defines stomach cancer as a medical condition characterized by cancer of cells of the stomach.

As used herein, the term "esophageal cancer" is meant to include the well-accepted medical definition that defines esophageal cancer as a medical condition characterized by cancer of cells of the esophagus.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body.

As used herein, the term "metastasized colorectal cancer cells" is meant to refer to colorectal cancer cells which have metastasized. Metastasized colorectal cancer cells localized in a part of the body other than the duodenum, small intestine (jejunum and ileum), large intestine (colon), including the cecum, ascending colon, transverse colon, descending colon, and sigmoid colon, and rectum.

As used herein, the term "metastasized stomach cancer cells" is meant to refer to stomach cancer cells which have metastasized. Metastasized stomach cancer cells localized in a part of the body other than the stomach.

As used herein, the term "metastasized esophageal cancer cells" is meant to refer to colorectal cancer cells which have metastasized. Metastasized esophageal cancer cells localized in a part of the body other than the esophagus.

As used herein, the term "non-colorectal sample" and "extra-intestinal sample" are used interchangeably and meant to refer to a sample of tissue or body fluid from a source other than colorectal tissue. In some preferred embodiments, the non-colorectal sample is a sample of tissue such as lymph nodes. In some preferred embodiments, the non-colorectal sample is a sample of extra-intestinal tissue which is an adenocarcinoma of unconfirmed origin. In some preferred embodiments, the non-colorectal sample is a blood sample.

As used herein, "an individual suffering from an adenocarcinoma of unconfirmed origin" is meant to refer to an individual who has a tumor in which the origin has not been definitively identified.

As used herein, "an individual is suspected of being susceptible to colorectal, stomach or esophageal cancer" is meant to refer to an individual who is at a particular risk of developing colorectal, stomach or esophageal cancer. Examples of individuals at a particular risk of developing colorectal, stomach or esophageal cancer are those whose family medical history indicates above average incidence of colorectal, stomach or esophageal cancer among family members and/or those who have already developed colorectal, stomach or esophageal cancer and have been effectively treated who therefore face a risk of relapse and recurrence.

As used herein, the term "cancer characterized by expression of GCC" is meant to refer to a cancer in which the cancer cells express GCC. Colorectal cells normally express GCC and continue to do so after transformation from normal to malignant. Accordingly, GCC is an effective marker for identifying and targeting metastasized colorectal cancer. Likewise, GCC mRNA has been found in proximal tubule cells of the kidney, exocrine duct cells of the pancreas, submandibular glands, cells of the bile duct. suggesting that GCC may be expressed by these cells. Esophageal and stomach cells normally do not express GCC but as they develop into cancer, GCC begins to be expressed. Accordingly, detection of GCC at locations other than locations in which GCC is normally expressed suggests cancer.

As used herein, the term "antisense composition" and "antisense molecules" are used interchangeably and are meant to refer to compounds that regulate transcription or translation by hybridizing to DNA or RNA and inhibiting and/or preventing transcription or translation from taking place. Antisense molecules include nucleic acid molecules and derivatives and analogs thereof. Antisense molecules hybridize to DNA or RNA in the same manner as complementary nucleotide sequences do regardless of whether or not the antisense molecule is a nucleic acid molecule or a derivative or analog. Antisense molecules may inhibit or prevent transcription or translation of genes whose expression is linked to cancer.

Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention may contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

As used herein, the term "naturally occurring amino acids" means the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, carboxyglutamic acid, arginine, ornithine and lysine. Unless specifically indicated, all amino acids referred to in this application are in the L-form.

As used herein, the term "side chain of a naturally occurring amino acid" refers to the substituent on the a-carbon of an a amino acid. The term "polar side chain of a naturally occurring amino acid" refers to the side chain of a positively charged, negatively charged or hydrophilic amino acid. The term "nonpolar side chain of a naturally occurring amino acid" refers to the side chain of a hydrophobic amino acid. Side Chains may be independently selected from, and may independently terminate with reactive groups: H; C1-C10 alkyl; C2-C6 alkenyl; C3-C11 cycloalkyl; C4-C11 cycloalkylalkyl; C6-C10 aryl; C7-C11 arylalkyl; C2-C7 alkylcarbonyl; C6-C10 arylcarbonyl; C2-C10 alkoxycarbonyl; C4-C11 cycloalkoxycarbonyl; C7-C11 bicycloalkoxycarbonyl; C6-C10 aryloxycarbonyl; aryl(C1-C10 alkoxy)carbonyl; C1-C6 alkylcarbonyloxy(C1-C4 alkoxy)carbonyl; C6-C10 arylcarbonyloxy(C1-C4 alkoxy)carbonyl; C4-C11 cycloalkylcarbonyloxy(C1-C4 alkoxy)carbonyl; -(pyridyl)-; -(pyridazinyl)-; -(pipirinyl)-; 1,3-dioxa-cyclopenten-2-one-yl)methyloxy, C10 to C14; (5-aryl-1,3-dioxa-cyclopenten-2-one-yl)methylOxy; (R)(R)N—(C1-C10 alkoxy)-; C3 to C11 cycloalkyl; C4 to C11 cycloalkylmethyl; C1-C6 alkoxy; benzyloxy; C6 to C10 aryl, heteroaryl or heteroarylalkyl; C7 to C11 arylalkyl, adamantylmethyl or C1-C10 alkyl; azabicyclononyl, 1-piperidinyl, 1-morpholinyl or 1-piperazinyl, each being optionally substituted with C1-C6 alkyl, C6-C10 aryl, heteroaryl, C7-C1, arylalkyl, C1-C6 alkylcarbonyl, C3-C7; cycloalkylcarbonyl, C1-C6 alkoxycarbonyl, C7-C11 arylalkoxycarbonyl, C1-C6 alkylsulfonyl or C6-C10 arylsulfonyl;

As used herein a reactive group is an atom(s) which reacts selectively with another atom to form a covalent bond. Non-limiting examples are —(CH2)SH, —(CH2)nBr and —(CH2)C(=O)Cl.

As used herein, the term "positively charged amino acid" or "cationic amino acid" as used herein includes any naturally occurring or unnatural amino acid having a positively charged side chain under normal physiological conditions. Examples of positively charged naturally occurring amino acids are arginine, lysine and histidine.

As used herein, the term "negatively charged amino acid" includes any naturally occurring or unnatural amino acid having a negatively charged side chain under normal physiological conditions. Examples of negatively charged naturally occurring amino acids are aspartic acid and glutamic acid.

As used herein, the term "hydrophilic amino acid" means any amino acid having an uncharged, polar side chain that is relatively soluble in water. Examples of naturally occurring hydrophilic amino acids are serine, threonine, tyrosine, asparagine, glutamine, and cysteine.

As used herein, the term "hydrophobic amino acid" means any amino acid having an uncharged, nonpolar side chain that is relatively insoluble in water. Examples of naturally occurring hydrophobic amino acids are alanine, leucine, isoleucine, valine, proline, phenylalanine, tryptophan and methionine.

As used herein, the a "derivatized amino acid" is a native amino acid which has been chemically modified. Non-limiting examples are hydroxyl-proline, penicillamine, N-methyl-alanine.

As used herein, the amino acid mimetic (isostere) is an organic molecule which approximates the steric and electronic configuration of the amino acid it is intended to replace. Non-limiting examples are,

| Amino Acid | Mimetic |
|---|---|
| Cysteine | 2-carboxy-3-thiopiperidine, penicillamine, homocysteine, 2-carboxy-3-bromo-pyridine, 2-bromo-benzoic acid, 2-bromo-cyclohexanoic acid |
| Proline | Pipecolic acid, Oic, |

As used herein, the term "beta turn" is defined as a 180 degree change in direction of a peptide chain in the span of 4 amino acid residues. The CO of the first residue (i) is hydrogen bonded to the NH of the fourth residue (i+3). In the case of STa, residue "i" is Asparagine 11 and residue i+3 is Cysteine 14 Theory are many types of Beta turns. These turn types can be categorized by the phi and psi angles of the second and third (i+1 and i+2 residues). The criteria for turn type I are as follows:

| Turn Type | (i) residue phi angle | (i + 1) residue psi angle | (i + 2) residue phi angle | (i + 3) residue psi angle |
|---|---|---|---|---|
| I | −60 | −30 | 90 | 0 |
| I' | 60 | 30 | 90 | 0 |
| II | −60 | 120 | 80 | 0 |
| II' | 60 | −120 | −80 | 0 |

Of course, a turn found in an actual protein will not have the exact angles above, but if the angles are in proximity then the turn can be classified accordingly.

STa has a type I beta turn from residues 11 through 14. An example of another type I turn is that which is found in the protein subtilisin. The turn consists of His39-Pro40-Asp41-Leu42. The CO of His39 (n) is hydrogen bonded to the NH of Leu42 (n+3), meeting the definition of a Beta turn. In addition the phi and psi angles for Pro40 (n+1) and Asp41 (n+2) were measured using the Swiss PDB Viewer. These angle measurements confirm that this is a Type I turn. In addition, although difficult to discern from the view shown here, the $O_2$ from the Proline extends to the rear or "down" as is to be expected from a Type I Turn.

| (n + 1)-Pro40 residue phi angle | (n + 1)-Pro40 residue psi angle | (n + 2)-Asp41 residue phi angle | (n + 2)-Asp41 residue psi angle |
|---|---|---|---|
| 64.21 | 17.19 | 99.32 | 12.92 |

In a Type I turn the hydrogen bond between CO of residue i and NH of residue i+3. The backbone dihedral angles of residue are (−60, −30) and (−90, 0) of residues i+1 and i+2, respectively of the type I turn. Proline is often found in position i+1 in type I turns as its phi angle is restricted to −60 and its imide nitrogen does not require a hydrogen bond. Glycine is favored in this position in the type II' as it requires a positive (left-handed) phi value.

For each type there are 4 sections for each residue. Each section represents a position in the turn. Within each section the first number represents the number of examples, the second number is the potential and the 3rd number is the significance as calculated by a d test. Values with mod(d) >=1.97 were taken as significant.

|   | position i | position i + 1 | position i + 2 | position i + 3 |
|---|---|---|---|---|
| I | 21 0.32 −5.73 | 40 0.60 −3.33 | 19 0.29 −5.98 | 50 0.75 −2.07 |
| F | 40 0.81 −1.37 | 21 0.42 −4.13 | 56 1.13 0.95 | 50 1.01 0.08 |
| V | 33 0.39 −5.78 | 61 0.72 −2.61 | 42 0.50 −4.76 | 65 0.77 −2.16 |
| L | 68 0.68 −3.38 | 70 0.70 −3.17 | 52 0.52 −5.05 | 74 0.74 −2.76 |
| W | 10 0.54 −1.98 | 12 0.65 −1.51 | 24 1.30 1.31 | 21 1.14 0.60 |
| M | 16 0.65 −1.75 | 13 0.53 −2.36 | 10 0.41 −2.97 | 15 0.61 −1.95 |
| A | 68 0.63 −3.99 | 115 1.07 0.76 | 86 0.80 −2.17 | 93 0.87 −1.46 |
| G | 109 1.07 0.74 | 41 0.40 −6.29 | 62 0.61 −4.12 | 242 2.38 14.51 |
| C | 36 1.57 2.75 | 20 0.87 −0.62 | 22 0.96 −0.20 | 31 1.35 1.69 |
| Y | 30 0.66 −2.37 | 28 0.61 −2.67 | 41 0.90 −0.71 | 39 0.85 −1.02 |
| P | 76 1.31 2.40 | 203 3.49 19.46 | 12 0.21 −6.20 | 2 0.03 −7.54 |
| T | 81 1.11 0.95 | 69 0.94 −0.49 | 105 1.44 3.85 | 81 1.11 0.95 |
| S | 120 1.52 4.74 | 119 1.50 4.63 | 102 1.29 2.65 | 81 1.02 0.21 |
| H | 45 1.60 3.20 | 15 0.53 −2.52 | 28 0.99 −0.04 | 26 0.92 −0.42 |
| E | 54 0.74 −2.28 | 112 1.54 4.72 | 88 1.21 1.83 | 74 1.02 0.13 |
| N | 125 2.25 9.50 | 38 0.68 −2.43 | 126 2.26 9.63 | 60 1.08 0.59 |
| Q | 31 0.72 −1.91 | 35 0.81 −1.29 | 51 1.18 1.18 | 25 0.58 −2.84 |
| D | 180 2.51 13.15 | 86 1.20 1.72 | 182 2.54 13.40 | 80 1.11 0.99 |
| K | 50 0.70 −2.57 | 85 1.20 1.70 | 72 1.01 0.11 | 78 1.10 0.85 |
| R | 36 0.64 −2.75 | 48 0.86 −1.11 | 49 0.88 −0.97 | 44 0.78 −1.65 |

From this, for STa, the preferred sequences for ST: Asp/Asn11-Pro12-Asp/Asn13-Gly/Cys14 compared to that seen in STa: Asn11-Pro12-Ala13-Cys14

Asp>Asn>His>Cys>Ser>Pro>Thr>Gly

When compared to the ST analog Database, Asp, Asn, Val, His and Tyr analogs at residue 12 are provide potent agonists.

Pro>>Glu>SerAsp>Lys>Ala

When compared to the ST analog Database, Pro, Aib, Val, Ala, Ile and D-Pro analogs at residue 12 all provide potent agonists.

Asp>Asn>Thr>Trp>Ser>Glu>Gln>Lys

When compared to the ST analog Database, only Ala, Gly and Ser analogs at residue 13 provide potent agonists.

Gly>Cys>Trp>Thr>Asp

When compared to the ST analog Database, no native substitutions are possible at residue 12 which provide potent agonists. Moreover, only a thioether crosslink (Hidaka) mutation exhibited any activity. There are numerous non-native amino acids that form beta turns.

According to Sato (Biochem, 33: 8641-8650 (1994)), STa has a $3_{10}$ helix from $Cys^6$ through $Cys^9$, with a characteristic H-bond between the carbonyl oxygen of $Cys^6$ and the amide nitrogen of $Cys^6$. A $3_{10}$-helix has i,i+3 H-bonds w/10 atoms between H-bonds.

As used herein the term "crosslinkers" is meant to refer to the bonds formed between functional groups on the two portions of the molecule linked together by them, i.e the bonds that crosslink two parts of a molecule. The bonds formed by linkers include:

1. Disulfides [—S—S—]; thioethers [—S—]; thiosulfoxides [—S(═O)—]; thiosulfonyl groups [—S(═O)2-];

2. Amides, alkylamides and arylamides [—$NR^{11}$—C(═O)]; thioamides, alkylthioamides and arylthioamides [—$NR^{11}$—C═S)—] wherein $R^{11}$ can be —H, —OH, methylene groups, [—$CR^{12}{}_2$—]; methine groups, [—$CR^{12}$═$CR^{12}$]; poly(methylene) groups, [—$(CR^{12}{}_2)_n$—] wherein n is an integer from 2 to about 16 and can include linear and branched saturated [—$CR^{12}$═$CR^{12}$—] and/or unsaturated [—$CR^{12}{}_2$—$CR^{12}{}_2$—] groups. $R^{12}$ can be any atom, including hydrogen;

3. Oxycarbonyl groups [—O—C(═O)—]; aminocarbonyl groups [—NH—C(═O)—]; carbonyl groups [—(C═O)—]; carbonyloxy groups [—C(═O)—O—]; carbonate groups [—O—C(═O)—O—]; carbonyloxymethyleneoxycarbonylalkylene groups [C(═O)—O—C($R^{20}R^{21}$)—O—C(═O)—(—CH2-)n-] where n' is an integer from 1 to 16 and each $R^{20}$ and $R^{21}$ is independently selected from the group consisting of H and methyl;

4. Urethane groups [—O—C(═O)—NH—]; thiourethane groups [—O—(C═S)—NH—]

5. —$NR^{31}$—$CR^{32}$, $R^{33}$—$CR^{34}R^{35}$— wherein $R^{31}$ can be selected from the group consisting of H, an alkyl group of from 1 to about 16 carbon atoms which may be linear, branched, saturated, unsaturated, or contain a carbocyclic ring of from 3 to about 10 carbon atoms, or a carbonylalkyl group wherein the alkyl group is defined immediately above; $R^{32}$ and $R^{33}$ are independently selected from the group consisting of H, an alkylene group of from 1 to about 16 carbon atoms, which may be linear, branched, saturated or unsaturated, and can contain a carbocyclic ring of from 3 to about 10 carbon atoms $R^{34}$ and $R^{35}$ are independently selected from the group consisting of H, an alkyl group of from 1 to about 16 carbon atoms which may be linear, branched, saturated, unsaturated, or contain a carbocyclic ring of from 3 to about 10 carbon atoms, or a carbonylalkyl group wherein the alkyl group is defined above, or preferably, where both $R^{34}$ and $R^{35}$ are taken together form a carbonyl group; and wherein at least one of $R^{32}R^{33}$ is not H, preferably —$NR^{31}$—$CR^{32}$, $R^{33}$—$CR^{34}R^{35}$— are selected from the group consisting of native and non-native amino acids;

6. Methylene groups, [—$CR^{41}{}_2$—]; methine groups, [—$CR^{41}$═$CR^{41}$]; poly(methylene) groups, [—$(CR^{41}{}_2)$n-] wherein n is an integer from 2 to about 16 and can include linear and branched saturated [—$CR^{41}$═$CR^{41}$—] and/or unsaturated [—$CR^{41}{}_2$—$CR^{41}{}_2$—] groups. $R^{41}$ can be any atom, including hydrogen;

7. Aryl- and alkylenecarbonyl groups [—$(CH_2)_n$—C(═O)—] wherein n is an integer from 1 to about 16;

8. Ethylenesulfonylethylene groups [—$CH_2CH_2$—S(═O)(═O)$_2CH_2CH_2$]

9. Ethylenesulfonylmethyleneoxymethylenesulfonylethylene groups [—$CH_2CH_2$—S(═O)$_2$—$CH_2$—O—$CH_2$—S(═O)$_2$—$CH_2CH_2$—];

10. Ethylenesulfonylmethylenesulfonylethylene groups $CH_2CH_2$—S(═O)2-$CH_2$—S(═O)$_2$—$CH_2CH_2$—];

11. Carbonyloxy groups [—C(═O)—O—];

12. Aryl- and alkylenecarbonyloxymethyleneoxycarbonylalkylene groups [—(—$CH_2$—)$_n$, C(═O)—O—C($R^{51}R^{52}$)—O—C(═O)—(—$CH_2$-)n-] where each n' is independently selected from the group of integers from 1 to 16 and each $R^{51}$ and $R^{52}$ is independently selected from the group consisting of H and methyl;

13. Carbonylalkylenecarbonyl groups [—C(═O)—$(CH_2)_w$—C(═O)—] wherein w is an integer from 1 to about 6, such as succinate and adipate.

As used herein, guanylyl cyclase C-mediated diarrhea or GC-C-mediated diarrhea is meant to refer to diarrhea which is associated with guanylyl cyclase C (GC-C) enzyme activity. An example of GC-C-mediated diarrhea is infectious diarrhea which is brought about by GC-C enzyme activation when the *E. coli* heat stable toxin (ST) binds to receptors on cells within the colon of an individual. Infectious diarrhea is also referred to herein as *E. coli* heat stable toxin induced diarrhea.

As used herein "alkyl" is meant to "Alkyl" groups as well as unsaturated and substituted forms such as "Substituted Alkyl," "Alkenyl," "Substituted Alkenyl," "Alkynyl," "Substituted Alkynyl" and "Alkoxy."

"Alkyl:" refers to a saturated branched, straight chain or cyclic hydrocarbon group. Typical alkyl groups include, but are not limited to, methyl, ethyl, propyl, isopropyl, butyl, isobutyl, t-butyl, pentyl, isopentyl, hexyl, and the like. In preferred embodiments, the alkyl groups are $(C_1-C_6)$ alkyl, with $(C_1-C_3)$ being particularly preferred.

"Substituted Alkyl:" refers to an alkyl group wherein one or more hydrogen atoms are each independently replaced with other substituents.

"Alkenyl:" refers to an unsaturated branched, straight chain or cyclic hydrocarbon group having at least one carbon-carbon double bond. The group may be in either the cis or trans conformation about the double bond(s). Typical alkenyl groups include, but are not limited to, ethenyl, propenyl, isopropenyl, butenyl, isobutenyl, tert-butenyl, pentenyl, hexenyl and the like. In preferred embodiments, the alkenyl group is a $(C_1-C_6)$ alkenyl, with $(C_1-C_3)$ being particularly preferred.

"Substituted Alkenyl:" refers to an alkenyl group wherein one or more hydrogen atoms are each independently replaced with other substituents.

"Alkynyl:" refers to an unsaturated branched, straight chain or cyclic hydrocarbon group having at least one carbon-carbon triple bond. Typical alkynyl groups include, but are not limited to, ethynyl, propynyl, butynyl, isobutynyl, pentynyl, hexynyl and the like. In preferred embodiments, the alkynyl group is $(C_1-C_6)$ alkynyl, with $(C_1-C_3)$ being particularly preferred.

"Substituted Alkynyl:" refers to an alkynyl group wherein one or more hydrogen atoms are each independently replaced with other substituents.

"Alkoxy:" refers to an —OR group, where R is alkyl, alkenyl or alkynyl, as defined above.

As used herein "aryl" is meant to "Aromatic moiety," "Substituted Aromatic Moiety," "Heteroaromatic moiety" and "Substituted Heteroaromatic moiety."

"Aromatic moiety:" refers to a moiety having an unsaturated cyclic hydrocarbon group which has a conjugated (4n+2).pi. electron system. Typical aromatic moieties include, but are not limited to, benzene, naphthalene, anthracene, azulene, indacene, and the like. In preferred embodiments, the aromatic moiety contains 5-20 carbons in the ring system, with 5-10 carbon atoms being particularly preferred.

"Substituted Aromatic Moiety:" refers to an aromatic moiety wherein one or more hydrogen atoms are each independently replaced with other substituents.

"Heteroaromatic moiety:" refers to an aromatic moiety wherein one or more of the ring carbon atoms is replaced with another atom such as N, O or S. Typical heteroaromatic moieties include, but are not limited to, pyran, pyrazole, pyridine, pyrrole, pyrazine, pyridazine, pyrimidine, pyrrolizine, quinazoline, quinoline, quinolizine, quinoxaline, selenophene, thiophere, tellurophene, xanthene and the like.

"Substituted Heteroaromatic moiety:" refers to a heteroaromatic moiety wherein one or more hydrogen atoms are each independently replaced with other substituents.

Overview

The present invention arises from the discovery that identification of structural determinants of GCC ligands necessary for GCC binding and GCC activation. Accordingly, retention of the structural determinants required for GCC binding and GCC activation yields compounds which are GCC agonists, i.e. compounds that bind to GCC and activate it. Compounds of the invention include agonists which induce cyclic GMP accumulation associated with the binding of GCC to natural ligands. On the other hand, retention of the structural determinants required for GCC binding and elimination of structural determinants required for GCC activation yields compounds which are GCC compound of the inventions, i.e. compounds that bind to GCC without activating it. Compounds of the invention include compound of the inventions that bind to GCC but do not induce cyclic GMP accumulation associated with the binding of GCC to natural ligands.

Compounds of the invention that are agonists have several uses including as anticancer compounds. They may be used alone or in combination with other therapeutic compounds. Further, they may be conjugated or unconjugated. The present invention relates to methods of treating individuals who have or are suspected of having cancer by administering compounds of the invention. Such compounds are useful in methods of inhibiting metastasis.

Compounds of the invention that are compound of the inventions have several uses including as anti-diarrhea compounds. They may be used alone or in combination with other therapeutic compounds. Further, the present invention relates to methods of treating individuals who have or are suspected of being at an elevated risk of contracting diarrhea by administering compounds of the invention.

Because compounds of the invention bind to GCC, the peptides and peptide analogues of the invention can be used to prepare imaging agents, therapeutics and diagnostic reagents related to the detection and treatment of cancer characterized by cells expressing GCC. As noted above, agonist peptides and peptide analogues of the invention can be used unconjugated to activate GCC in methods of treating cancer and preventing metastasis. Compound of the invention peptides and peptide analogues of the invention can be used to inhibit GCC activation in methods of treating diseases and disorders in which GCC activation has undesirable clinical effects which can be reduced or inhibited by inhibiting GCC activation.

Natural ligands of GCC include endogenous natural ligands guanylin and uroguanylin and the heat-stable enterotoxins (STs), a family of structurally-related peptides produced by different organisms including, but not limited to, *E. coli, Yersinia, Enterobacter*, and *Vibrio*. Table 1 shows the amino acid sequences of these natural ligands. The numerical positions referred to in the Table are the positions from the widely studied peptide *E. coli*. STa.

TABLE 1

| Position | | 5 | 6 | | | 9 | 10 | | | | 14 | | | 17 | |
|---|---|---|---|---|---|---|---|---|---|---|---|---|---|---|---|
| *E. coli* STa | NTF Y | C | C | E | L | C | C | N | P | A | C | A | G | C | Y |
| *E. coli* STh | SSSN Y | C | C | E | L | C | C | N | P | A | C | T | G | C | Y |
| Yersinia | SSDWD Y | C | C | D | L | C | C | N | P | A | C | A | G | C | Y |
| Vibrio | I D | C | C | E | I | C | C | N | P | A | C | F | G | C | L N |
| Guanylin | P N T | C | E | I | | C | A | Y | A | A | C | T | G | C | |
| Uroguanylin | Q E D | C | E | I | | C | I | N | V | A | C | T | G | C | |

The ST peptides each have six cysteine residues while the endogenous ligands have four each. In the ST peptides, the six cysteines form three di-sulphide bonds: amino acid 5 forms a disulfide bond with amino acid 10 (Loop A); amino acid 6 forms a disulfide bond with amino acid 14 (Loop B); and amino acid 8 forms a disulfide bond with amino acid 17 (Loop C). In the endogenous peptides, the four cysteines form two di-sulphide bonds: amino acid 6 forms a disulfide bond with amino acid 14 (Loop B), and amino acid 8 forms a disulfide bond with amino acid 17 (Loop C). In each peptide a dipeptide occurs between position 6 and 9 which produces a $3_{10}$-helix turn. Each peptide includes a Type II (β) turn between positions 9 and 14.

Some aspects of the present invention provides GCC agonists which retain the $3_{10}$-helix turn between positions 6 and 9 and the β turn between positions 9 and 14 while retaining the crosslinking between position 5 and 10 (Loop A), while eliminating the crosslinking between position 6 and 14 (Loop B) and the crosslinkage between positions 9 and 17 (Loop C). These compounds are referred to as Loop A compound of the inventions. It has been discovered that the retention of the three structural determinants ($3_{10}$-helix turn between 6 and 9, β turn between 9 and 14 and 5-10 cross linkage) and elimination of the two structural determinants (6-14 cross linkage and 9-17 cross linkage) yields compounds which bind to GCC but do not activate the signal cascade associated with GCC binding to natural ligands. In some embodiments, the amino acid at position 5 can be deleted in which case the amino acid at position 6 binds to the amino acid at 10. In some embodiments, the amino acid at position 10 can be deleted in which case the amino acid at position 5 binds to the amino acid at 9. In some embodiments, the amino acid at position 5 and at position 10 can be deleted in which case the amino acid at position 6 binds to the amino acid at 9. In some embodiments, the amino acid at position 5 can be present but does not cross link and the amino acid at position 6 crosslinks to the amino acid position 10. In some embodiments, the amino acids at position 5 and at position 10 can be present but does not cross link and the amino acid at position 6 crosslinks to the amino acid position 9. In some embodiments, the amino acid at position 10 can be present but does not cross link and the amino acid at position 5 crosslinks to the amino acid position 9. Amino acids or other moieties may be linked to amino acid 14. In some embodiments, the position at the C terminus of amino acid 14 is COOH. In some embodiments, the position at the C terminus of amino acid 14 is 1-30 amino acids, such as for example native sequences 15-18 provided the amino acid at position 17 does not cross link.

Some aspects of the present invention provides GCC agonists which retain the $3_{10}$-helix turn between positions 6 and 9 and the β turn between positions 9 and 14 while retaining the crosslinking between position 6 and 14 (Loop B), eliminating the crosslinking between position 9 and 17 (Loop C) and optionally retaining the crosslinkage between positions 5 and 10 (Loop A). If the compound does not have a tail linked to the C terminal of position 14 the compound is a Loop B agonists. In some embodiments, the compound has such a tail but it is degradable by a enzyme or other means present in the individual to whom it is administered. In such cases, the compound is an "in vivo agonist" in that it will act as a compound of the invention in vitro but will be converted to an agonist in vivo. An in vivo agonist can be maintained as a compound of the invention in vivo if the enzyme which degrades its tail is inhibited. For example, an in vivo Loop B agonist with a tail that is removed by elastase, such as AGA, can be maintained as a Loop B compound of the invention in vivo by administering an elastase inhibitor in conjunction with it. In some embodiments, the Loop B compound of the invention serves as a prodrug which is converted to a Loop B agonist in vivo by a means already present in the individual or by the addition of an agent that will convert it. It has been discovered that the retention of the three structural determinants ($3_{10}$-helix turn between 6 and 9, β turn between 9 and 14 and 6-14 cross linkage) and elimination of the structural determinant (9-17 cross linkage) yields compounds which bind to GCC and, provided they have no tail at the C terminus, activate the signal cascade associated with GCC binding to natural ligands. In some embodiments, the amino acid at position 5 can be deleted. In some embodiments, the amino acid at position 10 can be deleted. In some embodiments, the amino acids at positions 5 and 10 can be deleted. In some embodiments, the amino acids at position 5 and 10 are present but do not crosslink. In some embodiments, the amino acids at position 5 and 10 are present and crosslinked to each other. Amino acids or other moieties may be linked to amino acid 14 provided such amino acids or other moieties can be cleaved or otherwise removed form the molecule in vivo if the compound is to be an agonist. In some embodiments, the position at the C terminus of amino acid 14 is COOH. In some embodiments, the position at the C terminus of amino acid 14 is 1-30 amino acids, such as for example native sequences 15-18 provided the amino acid at position 17 does not cross link.

Compounds of the Invention

The compounds of the invention have structures according to (I)

R1-R2-R3-R4-R5-R6-R7 wherein:

R1 is combination of 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof;

R2 is a natural amino acid, blocked amino acid, synthetic amino acid, derivatized amino acid; an amino acid mimetic which optionally crosslinks, as defined herein, with R6;

R3 is a natural amino acid, blocked amino acid, synthetic amino acid, derivatized amino acid; an amino acid mimetic provided it crosslinks, as defined herein, with R8;

R4 is dipeptide comprising one or two natural amino acids, one or two blocked amino acids, one or two synthetic amino acids, one or two derivatized amino acids; one or two amino acid mimetics, or a dipeptide mimetic, wherein said dipeptide or dipeptide mimetic forms a $3_{10}$-helix turn group linking R3 to R5

R5 is a natural amino acid, blocked amino acid, synthetic amino acid, derivatized amino acid; an amino acid mimetic provided it does not crosslink with R9

R6 is a natural amino acid, blocked amino acid, synthetic amino acid, derivatized amino acid; an amino acid mimetic which optionally crosslinks, as defined herein, with R2;

R7 is tripeptide comprising one, two or three natural amino acids, one, two or three blocked amino acids, one, two or three amino acid mimetics, or a tripeptide mimetic, wherein said tripeptide or tripeptide mimetic forms a beta turn group linking R6 to R8

R8 is a natural amino acid, blocked amino acid, synthetic amino acid, derivatized amino acid; an amino acid mimetic provided it crosslinks, as defined herein, with R3;

R9 is a combination of 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof provided that it does not crosslink to R5.

According to aspects of the present invention, compounds of the invention have the structure of formula (I) provided that the compounds is not:

C-hC-E-L-A-C-N-P-A-X; hC
C-E-L-A-X-N-P-A-C;
C-C-E-L-A-C-N-P-A-C;
Y-Ca-C-E-L-F-Ca-N-P-A-C;
Y-C-C-E-L-mA-C-N-P-A-C;
Y-C-C-E-mL-A-C-N-P-A-C;
C-C-E-L-Cm-C-N-P-A-C-A-G-Cm;
C-C-E-L-Ca-C-N-P-A-C-A-G-Ca; and
X-Ca-E-L-A-hC-N-P-A-Ca;
wherein
hC is Homocysteine;
X is Alanine linked to hC via a covalent CH2-S bond between an Ala side chain and an hC side chain;
Cm is Cysteine(S-methoxybenzyl); and
Ca is Cysteine(S-acetamidomethyl).

In some preferred embodiments, R1 is preferably 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof. In some embodiments, R1 is 0-20 amino acids. In some embodiments R1 is smaller than 1000 daltons. In some embodiments, R1 is Y, NTFY, SSSNY, SSDWDY, ID, PN, or QE.

In some preferred embodiments, R2 is a Cysteine side chain analog [—(CR2)n-S, or —(CR2)n-H; where n is C1-C10, R is any atom and H is a reactive group], or aryl, alkyl and arylalkyl groups that may or may not crosslink to Cys10. In some embodiments, R2 is 2-carboxy-3-bromo-pyridine, 2-bromo-benzoic acid, 2-bromo-cyclohexanoic acid. R2 is preferably C cross linked to R6, blocked C such as Cmob, cross linked to R6 by a Carba link, any non-crosslinking aa or mimetic.

In some preferred embodiments, R3 is a Cysteine side chain analog [—(CR2)n-S, or —(CR2)n-H; where n is C1-C10, R is any atom and H is a reactive group], an alpha, beta or gamma amino acid capable of forming a crosslink with Cys14 via a side chain functional group (see side chains, above), an amino acid mimetic, such as 2-carboxy-3-thiopiperidine, which constrain the dihedral angles or the side chain to favorable configurations. R3 is preferably C crosslinked to C at R8 or any other moiety crosslinked to R8.

In some preferred embodiments, R4 is a single amino acid (all types), dipeptide, dipeptide mimetic and chain links, particularly structures with 4-8 atoms bridging the gap between R3 and R5, most preferably structures with 6 atoms bridging the gap between R3 and R5. Preferred amino acids for R4 are sarcosine, ornithine and lysine. Glu7 preferred amino acid replacements are Gln, Gly, Ser, Ala, Pro, Asp, Asn and L-octahydroindole-2-carboxyilic acid, and their N-alkyl, N-hydroxyl, or N-aryl analogs. Leu8 preferred amino acid replacements are Ile, Norleucine, Met, Val, Phe, Trp, Tyr, Gln, Gly, Ala, Pro and L-1,2,3,4-tetrahydroisoquinoline-3-carboxyilic acid, and their N-alkyl, N-hydroxyl, or N-aryl analogs. R4 is preferably a dipeptide such as E-L, or E-NmethylLeu.

In some preferred embodiments, R5 is a single amino acid (all types), preferably hydrophobic or neutral ones, and their N-alkyl, N-hydroxyl, or N-aryl analogs, more preferably Ala, N(Me)-Ala, Thr, Leu, N(Me)-Leu, Phe and blocked Cysteine, Serine and Threonine, an amino acid mimetic, such as L-1,2,3,4-tetrahydroisoquinoline-2-carboxyilic acid, which constrain the dihedral angles or the side chain to favorable configurations. In some preferred embodiments, R5 may be comprised of amino acids or organic molecules with a hydrophobicity of at least −2.0 (Glutamic acid is the lowest native AA with a value of −1.22), and preferably a value greater than zero; and more preferably a value greater than one. Hydrophobicity is determined by the method of Sweet and Eisenberg (Sweet R. M., Eisenberg D., J. Mol. Biol. 171:479-488 (1983) which is incorporated herein by reference). R5 is preferably A L, T, F, V, I, Y, NmethylLeu, NmethylAlam, and NmethylVal.

In some preferred embodiments, R6 is a single amino acid (all types), or an N-alkyl, N-hydroxyl, or N-aryl analog of one, an amino acid mimetic, such as which constrain the dihedral angles or the side chain to favorable configurations. R6 is preferably C cross linked to R2, blocked C such as Cmob, cross linked to R2 by a Carba link any non-crosslinking amino acid or mimetic.

In some preferred embodiments, R7 is a dipeptide mimetic, such as bicycle-L-seryl-proline, Btd, APM, ACTB, or ACDN

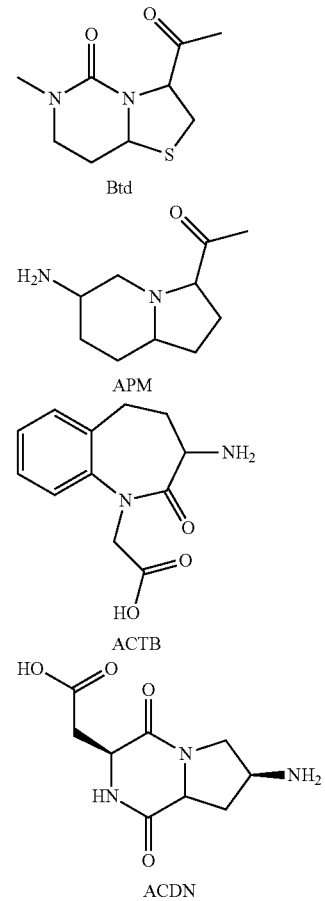

Btd

APM

ACTB

ACDN

In some embodiments, R7 is X-Y-Z wherein
X is a single amino acid (all types), preferably Asn, Asp, Ala, His, GlnGly, beta-Alanine), or a short one (Ala, Ser, Thr, Asp), and their N-alkyl, N-hydroxyl, or N-aryl analogs or a synthetic amino acids, preferably Isoasparagine or beta alanine.

Y is a single amino acids (all types), preferably Pro, Ile, Ala, Val (both D and L) and their N-alkyl, N-hydroxyl, or N-aryl analogs. Synthetic amino acids, such as homoPro, Nipecotic acid, isonipecotic acid, Oic, Tic, Aib, aminobenzoate, carboxypiperidine, azetidine carboxylate and aminocyclopentene carboxylic acid. Amino acid mimetics, such as L-1,2,3,4-tetrahydroisoquinoline-3-carboxylic acid, which constrain the dihedral angles or the side chain to favorable configurations.

Z is a single amino acid (all types), preferably with no sidechain (Gly, beta-Alanine), or a short one (Ala, Ser, Thr, Asp), and their N-alkyl, N-hydroxyl, or N-aryl analogs, more preferably Ala, N(Me)-Ala, and Gly.

R7 is preferably a tripeptide N-P-A.

In some preferred embodiments, R8 is a Cysteine side chain analog [—(CR2)n-S, or —(CR2)n-H; where n is C1-C10, R is any atom and H is a reactive group], an alpha, beta or gamma amino acids capable of forming a crosslink with Cys14 via a side chain functional group (see side chains, above), an amino acid mimetic, such as 2-carboxy-3-thiopiperidine, which constrain the dihedral angles or the side chain to favorable configurations. R8 is preferably C crosslinked to C at R3 or any other moiety crosslinked to R3.

In some preferred embodiments, R9 is preferably smaller than 1000 daltons. R9 is preferably 0-20 amino acids, AGA or Y.

It is preferred that the compound of the invention be as small as possible. Thus it is preferred that the compound of the invention be a non-peptide small molecule or small peptide, preferably less than 25 amino acids, more preferably less than 20 amino acids. In some embodiments, the GCC compound of the invention binding is in the form of a conjugated composition is less than 15 amino acids. The compound of the invention comprising 10, 11, 12, 13, 14, 15, 16, 17, 18, 19 amino acids may be used according to the present invention. It is within the scope of the present invention to include larger molecules which serve as compounds of the invention.

The present invention also relates to compounds that are Loop A compound of the inventions. The present invention relates to compounds having Formula (II):

R201-R202-R203-R204-R205-R206-R207     (II)

wherein:

R201 is absent or 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof;

R202 is absent, or is a natural amino acid, blocked amino acid, synthetic amino acid, derivatized amino acid or an amino acid mimetic which does not crosslink to any other amino acid, or is a natural amino acid, blocked amino acid, synthetic amino acid, derivatized amino acid or amino acid mimetic that crosslinks with R205 or R206, wherein if R202 is absent or a natural amino acid, blocked amino acid, synthetic amino acid, derivatized amino acid or an amino acid mimetic which does not crosslink to any other amino acid then R203 is a natural amino acid, blocked amino acid, synthetic amino acid, derivatized amino acid or amino acid mimetic that crosslinks with R205 or R206;

R203 is absent, or is a natural amino acid, blocked amino acid, synthetic amino acid, derivatized amino acid or an amino acid mimetic which does not crosslink to any other amino acid, or if R202 is absent or is a natural amino acid, blocked amino acid, synthetic amino acid, derivatized amino acid or an amino acid mimetic which does not crosslink to any other amino acid then R203 is a natural amino acid, blocked amino acid, synthetic amino acid, derivatized amino acid or amino acid mimetic that crosslinks with R205 or R206;

R204 is one or two natural amino acids, one or two blocked amino acids, one or two synthetic amino acids, one or two derivatized amino acids, one or two amino acid mimetics, or a dipeptide mimetic or combinations thereof, wherein R204 forms a $3_{10}$-helix turn group linking R203 to R205;

R205 is absent, or is a natural amino acid, blocked amino acid, synthetic amino acid, derivatized amino acid or an amino acid mimetic which does not crosslink to any other amino acid, or if R206 is absent or is a natural amino acid, blocked amino acid, synthetic amino acid, derivatized amino acid or an amino acid mimetic which does not crosslink to any other amino acid then R205 is a natural amino acid, blocked amino acid, synthetic amino acid, derivatized amino acid or amino acid mimetic that crosslinks with R202 or R203;

R206 is absent, or is a natural amino acid, blocked amino acid, synthetic amino acid, derivatized amino acid or an amino acid mimetic which does not crosslink to any other amino acid, or is a natural amino acid, blocked amino acid, synthetic amino acid, derivatized amino acid or amino acid mimetic that crosslinks with R202 or R203, wherein if R206 is absent or a natural amino acid, blocked amino acid, synthetic amino acid, derivatized amino acid or an amino acid mimetic which does not crosslink to any other amino acid then R205 is a natural amino acid, blocked amino acid, synthetic amino acid, derivatized amino acid or amino acid mimetic that crosslinks with R202 or R203; and R207 is absent or 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof.

In some preferred embodiments, R201 is preferably 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof. In some embodiments, R1 is 0-20 amino acids. In some embodiments R201 is smaller than 1000 daltons. In some embodiments, R201 is Y, NTFY, SSSNY, SSDWDY, ID, PN, or QE.

In some preferred embodiments, R202 is a Cysteine. In some preferred embodiments, R202 is a penacillamine. In some preferred embodiments, R202 is a Cysteine side chain analog [—(CR2)n-S, or —(CR2)n-H; where n is C1-C10, R is any atom and H is a reactive group], or aryl, alkyl and arylalkyl groups that may or may not crosslink to Cys10. In some embodiments, R202 is 2-carboxy-3-bromo-pyridine, 2-bromo-benzoic acid, 2-bromo-cyclohexanoic acid. R202 is preferably C cross linked to R206, or R205, or blocked C such as Cmob, cross linked to R206 by a Carba link, any non-crosslinking aa or mimetic.

In some preferred embodiments, R203 is absent or cannot form a crosslink (such as y for example being a blocked Cys, Alanine, Serrine or other alpha amino acid). In embodiments in which R202 does not form a crosslink, R203 forms a crosslink and may be for example Cysteine, penacillamine or another Cysteine side chain analog [—(CR2)n-S, or —(CR2)n-H; where n is C1-C10, R is any atom and H is a reactive group], or aryl, alkyl and arylalkyl groups. In some such embodiments, R203 may be as R202 described above and cross link with R206 or R205.

In some preferred embodiments, R204 is a single amino acid (all types), dipeptide, dipeptide mimetic and chain links, particularly structures with 4-8 atoms bridging the gap between R203 and R205, most preferably structures with 6 atoms bridging the gap between R203 and R205. Preferred amino acids for R204 are sarcosine, ornithine and lysine. Glu7 preferred amino acid replacements are Gln, Gly, Ser, Ala, Pro, Asp, Asn and L-octahydroindole-2-carboxyilic acid, and their N-alkyl, N-hydroxyl, or N-aryl analogs. Leu8 preferred amino acid replacements are Ile, Norleucine, Met, Val, Phe, Trp, Tyr, Gln, Gly, Ala, Pro and L-1,2,3,4-tetrahydroisoquinoline-3-carboxyilic acid, and their N-alkyl, N-hydroxyl, or N-aryl analogs. R204 is preferably a dipeptide such as E-L, or E-NmethylLeu.

In some preferred embodiments, R205 is a single amino acid (all types), preferably hydrophobic or neutral ones, and their N-alkyl, N-hydroxyl, or N-aryl analogs, more preferably Ala, N(Me)-Ala, Thr, Leu, N(Me)-Leu, Phe and blocked Cysteine, Serine and Threonine, an amino acid mimetic, such as L-1,2,3,4-tetrahydroisoquinoline-3-carboxyilic acid, which constrain the dihedral angles or the side chain to favorable configurations. In some preferred embodiments, R205 may be comprised of amino acids or organic molecules with a hydrophobicity of at least −2.0 (Glutamic acid is the lowest native AA with a value of −1.22), and preferably a value greater than zero; and more preferably a value greater than one. Hydrophobicity is determined by the method of Sweet and Eisenberg (Sweet R. M., Eisenberg D., J. Mol. Biol. 171:479-488 (1983) which is incorporated herein by reference). R205 is preferably A L, T, F, V, I, Y, NmethylLeu, NmethylAlam, and NmethylVal. In embodiments, R205 is absent or cannot form a crosslink (such as y for example being a blocked Cys, Alanine, Serrine or other alpha amino acid). In embodiments in which R206 does not form a crosslink, R205 forms a crosslink and may be for example Cysteine, penacillamine or another Cysteine side chain analog [—(CR2)n-S, or —(CR2)n-H; where n is C1-C10, R is any atom and H is a reactive group], or aryl, alkyl and arylalkyl groups. In some such embodiments, R205 may be as R202 described above and cross link with R202 or R203.

In some preferred embodiments, R206 is a Cysteine. In some preferred embodiments, R206 is a penacillamine. In some preferred embodiments, R206 is a Cysteine side chain analog [—(CR2)n-S, or —(CR2)n-H; where n is C1-C10, R is any atom and H is a reactive group], or aryl, alkyl and arylalkyl groups. In some embodiments, R206 is 2-carboxy-3-bromo-pyridine, 2-bromo-benzoic acid, 2-bromo-cyclohexanoic acid. R206 is preferably C cross linked to R202, or R202, or blocked C such as Cmob, cross linked to R202 by a Carba link, any non-crosslinking aa or mimetic.

In some preferred embodiments, R207 is absent, COOH, NPAAAGCacmY, or ST11-18 with a change at 17 to remove crosslinking function.

The present invention also relates to compounds that are Loop B compounds. The present invention relates to compounds having Formula (III):

R301-R302-R303-R304-R305-R306-R307-R308-R309 (III)

wherein:

R301 is combination of 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof;

R302 is a natural amino acid, blocked amino acid, synthetic amino acid, derivatized amino acid, or an amino acid mimetic wherein R302 may crosslink with R306;

R303 is a natural amino acid, blocked amino acid, synthetic amino acid, derivatized amino acid or amino acid mimetic that crosslinks with R308;

R304 is one or two natural amino acids, one or two blocked amino acids, one or two synthetic amino acids, one or two derivatized amino acids, one or two amino acid mimetics, or a dipeptide mimetic or combinations thereof, wherein R304 forms a $3_{10}$-helix turn group linking R303 to R305;

R305 is a natural amino acid, blocked amino acid, synthetic amino acid, derivatized amino acid or amino acid mimetic that does not crosslink with R309

R306 is a natural amino acid, blocked amino acid, synthetic amino acid, derivatized amino acid, or amino acid mimetic wherein R306 may crosslink with R302;

R307 is one, two or three natural amino acids, one, two or three blocked amino acids, one, two or three amino acid mimetics, or a tripeptide mimetic or combinations thereof, wherein R307 forms a beta turn group linking R306 to R308

R308 is a natural amino acid, blocked amino acid, synthetic amino acid, derivatized amino acid or amino acid mimetic that crosslinks with R303;

R309 is absent or 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof that does not crosslink to R305;

wherein the structure of the compounds is not:

SEQ. ID NO. 3: C-hC-E-L-A-C-N-P-A-X; hC;
SEQ. ID NO. 2: C-E-L-A-X-N-P-A-C
SEQ. ID NO. 3: C-C-E-L-A-C-N-P-A-C;
SEQ. ID NO. 4: C-C-E-L-A-C-N-P-A-C-T-G-A;
SEQ. ID NO. 5: Y-Ca-C-E-L-F-Ca-N-P-A-C;
SEQ. ID NO. 6: Y-C-C-E-L-mA-C-N-P-A-C;
SEQ. ID NO. 6: Y-C-C-E-L-mL-C-N-P-A-C;
SEQ. ID NO. 7: C-C-E-L-Cm-C-N-P-A-C-A-G-Cm;
SEQ. ID NO. 7: C-C-E-L-Ca-C-N-P-A-C-A-G-Ca; or
SEQ. ID NO. 8: X-Ca-E-L-A-Hc-N-P-A-Ca;

wherein hC is Homocysteine;

X is Alanine linked to hC via a covalent CH2-S bond between an Ala side chain and an hC side chain;

Cm is Cysteine(S-methoxybenzyl); and

Ca is Cysteine(S-acetamidomethyl).

In some preferred embodiments, R301 is preferably 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof. In some embodiments, R301 is 0-20 amino acids. In some embodiments R301 is smaller than 1000 daltons. In some embodiments, R301 is Y, NTFY, SSSNY, SSDWDY, ID, PN, or QE.

In some preferred embodiments, R302 is a Cysteine side chain analog [—(CR2)n-S, or —(CR2)n-H; where n is C1-C10, R is any atom and H is a reactive group], or aryl, alkyl and arylalkyl groups that may or may not crosslink to Cys10 (R306). In some embodiments, R302 is 2-carboxy- 3-bromo-pyridine, 2-bromo-benzoic acid, 2-bromo-cyclohexanoic acid. R302 is preferably C cross linked to R306, blocked C such as Cmob, cross linked to R306 by a Carba link, any non-crosslinking aa or mimetic.

In some preferred embodiments, R303 is a Cysteine side chain analog [—(CR2)n-S, or —(CR2)n-H; where n is C1-C10, R is any atom and H is a reactive group], an alpha, beta or gamma amino acid capable of forming a crosslink with Cys14 (R308) via a side chain functional group (see side chains, above), an amino acid mimetic, such as 2-carboxy-3-thiopiperidine, which constrain the dihedral angles or the side chain to favorable configurations. R303 is preferably C crosslinked to C at R308 or any other moiety crosslinked to R308.

In some preferred embodiments, R304 is a single amino acid (all types), dipeptide, dipeptide mimetic and chain links, particularly structures with 4-8 atoms bridging the gap between R303 and R305, most preferably structures with 6 atoms bridging the gap between R303 and R305. Preferred amino acids for R304 are sarcosine, ornithine and lysine. Glu7 preferred amino acid replacements are Gln, Gly, Ser, Ala, Pro, Asp, Asn and L-octahydroindole-2-carboxyilic acid, and their N-alkyl, N-hydroxyl, or N-aryl analogs. Leu8 preferred amino acid replacements are Ile, Norleucine, Met, Val, Phe, Trp, Tyr, Gln, Gly, Ala, Pro and L-1,2,3,4-tetrahydroisoquinoline-3-carboxyilic acid, and their N-alkyl, N-hydroxyl, or N-aryl analogs. R304 is preferably a dipeptide such as E-L, or E-NmethylLeu.

In some preferred embodiments, R305 is a single amino acid (all types), preferably hydrophobic or neutral ones, and their N-alkyl, N-hydroxyl, or N-aryl analogs, more preferably Ala, N(Me)-Ala, Thr, Leu, N(Me)-Leu, Phe and blocked Cysteine, Serine and Threonine, an amino acid mimetic, such as L-1,2,3,4-tetrahydroisoquinoline-3-carboxyilic acid, which constrain the dihedral angles or the side chain to favorable configurations. In some preferred embodiments, R305 may be comprised of amino acids or organic molecules with a hydrophobicity of at least −2.0 (Glutamic acid is the lowest native AA with a value of −1.22), and preferably a value greater than zero; and more preferably a value greater than one. Hydrophobicity is determined by the method of Sweet and Eisenberg (Sweet R. M., Eisenberg D., J. Mol. Biol. 171:479-488 (1983) which is incorporated herein by reference). R305 is preferably A L, T, F, V, I, Y, NmethylLeu, NmethylAlam, and NmethylVal.

In some preferred embodiments, R306 is a single amino acid (all types), or an N-alkyl, N-hydroxyl, or N-aryl analog of one, an amino acid mimetic, such as which constrain the dihedral angles or the side chain to favorable configurations. R306 is preferably C cross linked to R302, blocked C such as Cmob, cross linked to R302 by a Carba link any non-crosslinking amino acid or mimetic.

In some preferred embodiments, R307 is a dipeptide mimetic, such as bicycle-L-seryl-proline, Btd, APM, ACTB, or ACDN

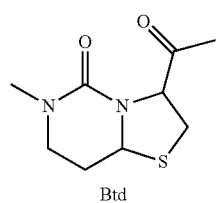

Btd

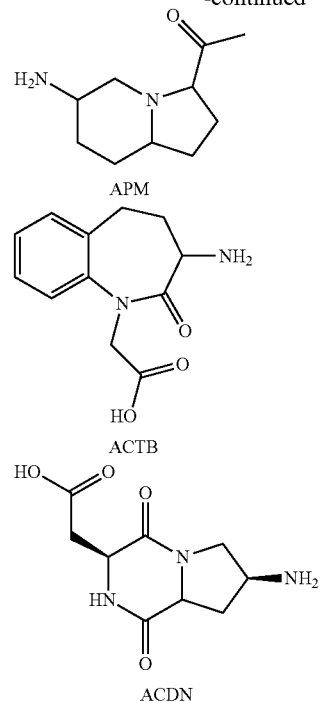

APM

ACTB

ACDN

In some embodiments, R307 is X-Y-Z wherein

X is a single amino acid (all types), preferably Asn, Asp, Ala, His, GlnGly, beta-Alanine), or a short one (Ala, Ser, Thr, Asp), and their N-alkyl, N-hydroxyl, or N-aryl analogs or a synthetic amino acids, preferably Isoasparagine or beta alanine.

Y is a single amino acids (all types), preferably Pro, Ile, Ala, Val (both D and L) and their N-alkyl, N-hydroxyl, or N-aryl analogs. Synthetic amino acids, such as homoPro, Nipecotic acid, isonipecotic acid, Oic, Tic, Aib, aminobenzoate, carboxypiperidine, azetidine carboxylate and aminocyclopentene carboxylic acid. Amino acid mimetics, such as L-1,2,3,4-tetrahydroisoquinoline-3-carboxylic acid, which constrain the dihedral angles or the side chain to favorable configurations.

Z is a single amino acid (all types), preferably with no sidechain (Gly, beta-Alanine), or a short one (Ala, Ser, Thr, Asp), and their N-alkyl, N-hydroxyl, or N-aryl analogs, more preferably Ala, N(Me)-Ala, and Gly.

R307 is preferably a tripeptide N-P-A.

In some preferred embodiments, R308 is a Cysteine side chain analog [—(CR2)n-S, or —(CR2)n-H; where n is C1-C10, R is any atom and H is a reactive group], an alpha, beta or gamma amino acids capable of forming a crosslink with Cys6 (R303) via a side chain functional group (see side chains, above), an amino acid mimetic, such as 2-carboxy-3-thiopiperidine, which constrain the dihedral angles or the side chain to favorable configurations. R308 is preferably C crosslinked to C at R303 or any other moiety crosslinked to R303.

In some preferred embodiments, R309 is preferably smaller than 1000 daltons. R9 is preferably 0-20 amino acids, NPAAAGCacmY, or ST11-18 with a change at 17 to remove crosslinking function, COOH, AGA or Y.

In some embodiments, the Loop B compounds either have no tail at R309 or have one that can be cleaved such that the molecule becomes an agonist. The present invention further relates to Loop B agonist compounds having Formula (IV):

$$R401\text{-}R402\text{-}R403\text{-}R404\text{-}R405\text{-}R406\text{-}R407\text{-}R408\text{-}R409 \quad (IV)$$

wherein

R401 is combination of 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof;

R402 is a natural amino acid, blocked amino acid, synthetic amino acid, derivatized amino acid, or an amino acid mimetic wherein R402 may crosslink with R406;

R403 is a natural amino acid, blocked amino acid, synthetic amino acid, derivatized amino acid or amino acid mimetic that crosslinks with R408;

R404 is one or two natural amino acids, one or two blocked amino acids, one or two synthetic amino acids, one or two derivatized amino acids, one or two amino acid mimetics, or a dipeptide mimetic or combinations thereof, wherein R404 forms a $3_{10}$-helix turn group linking R403 to R405;

R405 is a natural amino acid, blocked amino acid, synthetic amino acid, derivatized amino acid or amino acid mimetic that does not crosslink with R409

R406 is a natural amino acid, blocked amino acid, synthetic amino acid, derivatized amino acid, or amino acid mimetic wherein R406 may crosslink with R402;

R407 is one, two or three natural amino acids, one, two or three blocked amino acids, one, two or three amino acid mimetics, or a tripeptide mimetic or combinations thereof, wherein R407 forms a beta turn group linking R406 to R408

R408 is a natural amino acid, blocked amino acid, synthetic amino acid, derivatized amino acid or amino acid mimetic that crosslinks with R403;

R409 is absent or 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof that does not crosslink to R405.

In some preferred embodiments, R401 is preferably 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof. In some embodiments, R401 is 0-20 amino acids. In some embodiments R401 is smaller than 1000 daltons. In some embodiments, R401 is Y, NTFY, SSSNY, SSDWDY, ID, PN, or QE.

In some preferred embodiments, R402 is a Cysteine side chain analog [—(CR2)n-S, or —(CR2)n-H; where n is C1-C10, R is any atom and H is a reactive group], or aryl, alkyl and arylalkyl groups that may or may not crosslink to Cys10 (R406). In some embodiments, R402 is 2-carboxy-3-bromo-pyridine, 2-bromo-benzoic acid, 2-bromo-cyclohexanoic acid. R402 is preferably C cross linked to R406, blocked C such as Cmob, cross linked to R406 by a Carba link, any non-crosslinking aa or mimetic.

In some preferred embodiments, R403 is a Cysteine side chain analog [—(CR2)n-S, or —(CR2)n-H; where n is C1-C10, R is any atom and H is a reactive group], an alpha, beta or gamma amino acid capable of forming a crosslink with Cys14 (R408) via a side chain functional group (see side chains, above), an amino acid mimetic, such as 2-carboxy-3-thiopiperidine, which constrain the dihedral angles or the side chain to favorable configurations. R403 is preferably C crosslinked to C at R408 or any other moiety crosslinked to R408.

In some preferred embodiments, R404 is a single amino acid (all types), dipeptide, dipeptide mimetic and chain links, particularly structures with 4-8 atoms bridging the gap between R403 and R405, most preferably structures with 6 atoms bridging the gap between R403 and R405. Preferred amino acids for R404 are sarcosine, ornithine and lysine. Glu7 preferred amino acid replacements are Gln, Gly, Ser, Ala, Pro, Asp, Asn and L-octahydroindole-2-carboxyilic acid, and their N-alkyl, N-hydroxyl, or N-aryl analogs. Leu8 preferred amino acid replacements are Ile, Norleucine, Met, Val, Phe, Trp, Tyr, Gln, Gly, Ala, Pro and L-1,2,3,4-tetrahydroisoquinoline-3-carboxyilic acid, and their N-alkyl, N-hydroxyl, or N-aryl analogs. R404 is preferably a dipeptide such as E-L, or E-NmethylLeu.

In some preferred embodiments, R405 is a single amino acid (all types), preferably hydrophobic or neutral ones, and their N-alkyl, N-hydroxyl, or N-aryl analogs, more preferably Ala, N(Me)-Ala, Thr, Leu, N(Me)-Leu, Phe and blocked Cysteine, Serine and Threonine, an amino acid mimetic, such as L-1,2,3,4-tetrahydroisoquinoline-3-carboxyilic acid, which constrain the dihedral angles or the side chain to favorable configurations. In some preferred embodiments, R405 may be comprised of amino acids or organic molecules with a hydrophobicity of at least −2.0 (Glutamic acid is the lowest native AA with a value of −1.22), and preferably a value greater than zero; and more preferably a value greater than one. Hydrophobicity is determined by the method of Sweet and Eisenberg (Sweet R. M., Eisenberg D., J. Mol. Biol. 171:479-488 (1983) which is incorporated herein by reference). R405 is preferably A L, T, F, V, I, Y, NmethylLeu, NmethylAlam, and NmethylVal.

In some preferred embodiments, R406 is a single amino acid (all types), or an N-alkyl, N-hydroxyl, or N-aryl analog of one, an amino acid mimetic, such as which constrain the dihedral angles or the side chain to favorable configurations. R406 is preferably C cross linked to R402, blocked C such as Cmob, cross linked to R402 by a Carba link any non-crosslinking amino acid or mimetic.

In some preferred embodiments, R407 is a dipeptide mimetic, such as bicycle-L-seryl-proline, Btd, APM, ACTB, or ACDN

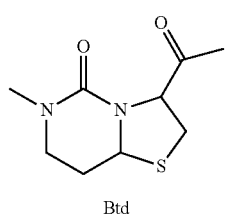

Btd

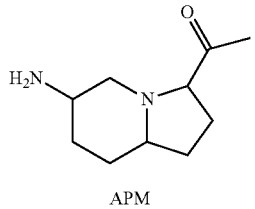

APM

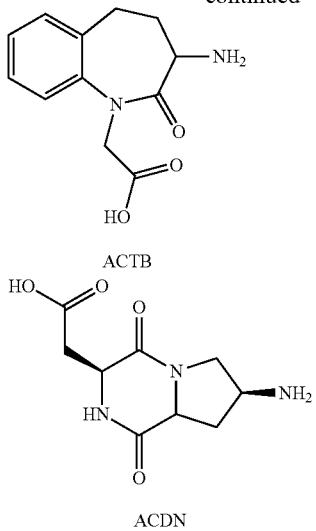

ACTB

ACDN

In some embodiments, R407 is X-Y-Z wherein

X is a single amino acid (all types), preferably Asn, Asp, Ala, His, GlnGly, beta-Alanine), or a short one (Ala, Ser, Thr, Asp), and their N-alkyl, N-hydroxyl, or N-aryl analogs or a synthetic amino acids, preferably Isoasparagine or beta alanine.

Y is a single amino acids (all types), preferably Pro, Ile, Ala, Val (both D and L) and their N-alkyl, N-hydroxyl, or N-aryl analogs. Synthetic amino acids, such as homoPro, Nipecotic acid, isonipecotic acid, Oic, Tic, Aib, aminobenzoate, carboxypiperidine, azetidine carboxylate and aminocyclopentene carboxylic acid. Amino acid mimetics, such as L-1,2,3,4-tetrahydroisoquinoline-3-carboxylic acid, which constrain the dihedral angles or the side chain to favorable configurations.

Z is a single amino acid (all types), preferably with no sidechain (Gly, beta-Alanine), or a short one (Ala, Ser, Thr, Asp), and their N-alkyl, N-hydroxyl, or N-aryl analogs, more preferably Ala, N(Me)-Ala, and Gly.

R407 is preferably a tripeptide N-P-A.

In some preferred embodiments, R408 is a Cysteine side chain analog [—(CR2)n-S, or —(CR2)n-H; where n is C1-C10, R is any atom and H is a reactive group], an alpha, beta or gamma amino acids capable of forming a crosslink with Cys6 (R403) via a side chain functional group (see side chains, above), an amino acid mimetic, such as 2-carboxy-3-thiopiperidine, which constrain the dihedral angles or the side chain to favorable configurations. R408 is preferably C crosslinked to C at R403 or any other moiety crosslinked to R403.

In some preferred embodiments, R409 is preferably COOH. In some embodiments, R9 is preferably 0-20 amino acids, provided that it is cleavable in vivo to be converted to an agonist. Examples of cleavable tails are NPAAAGCacmY, and ST11-18 with a change at 17 to remove crosslinking function.

The present invention also relates to compounds that are Loop B prodrugs, that is Loop B compounds which have tails that render them compound of the inventions which tails are claevable. The present invention relates to compounds having Formula (V):

Formula (V):

R501-R502-R503-R504-R505-R506-R507-R508-R509 (V)

wherein:

R501 is combination of 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof;

R502 is a natural amino acid, blocked amino acid, synthetic amino acid, derivatized amino acid, or an amino acid mimetic wherein R502 may crosslink with R506;

R503 is a natural amino acid, blocked amino acid, synthetic amino acid, derivatized amino acid or amino acid mimetic that crosslinks with R508;

R504 is one or two natural amino acids, one or two blocked amino acids, one or two synthetic amino acids, one or two derivatized amino acids, one or two amino acid mimetics, or a dipeptide mimetic or combinations thereof, wherein R504 forms a $3_{10}$-helix turn group linking R503 to R505;

R505 is a natural amino acid, blocked amino acid, synthetic amino acid, derivatized amino acid or amino acid mimetic that does not crosslink with R509

R506 is a natural amino acid, blocked amino acid, synthetic amino acid, derivatized amino acid, or amino acid mimetic wherein R506 may crosslink with R502;

R507 is one, two or three natural amino acids, one, two or three blocked amino acids, one, two or three amino acid mimetics, or a tripeptide mimetic or combinations thereof, wherein R507 forms a beta turn group linking R506 to R508

R508 is a natural amino acid, blocked amino acid, synthetic amino acid, derivatized amino acid or amino acid mimetic that crosslinks with R503;

R509 is 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof that does not crosslink to R505;

wherein the compound is degradable in vivo and the structure of the compounds is not SEQ. ID NO. 4: C-C-E-L-A-C-N-P-A-C-T-G-A;

In some preferred embodiments, R501 is preferably 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof. In some embodiments, R501 is 0-20 amino acids. In some embodiments R501 is smaller than 1000 daltons. In some embodiments, R501 is Y, NTFY, SSSNY, SSDWDY, ID, PN, or QE.

In some preferred embodiments, R502 is a Cysteine side chain analog [—(CR2)n-S, or —(CR2)n-H; where n is C1-C10, R is any atom and H is a reactive group], or aryl, alkyl and arylalkyl groups that may or may not crosslink to Cys10 (R506). In some embodiments, R502 is 2-carboxy-3-bromo-pyridine, 2-bromo-benzoic acid, 2-bromo-cyclohexanoic acid. R502 is preferably C cross linked to R506, blocked C such as Cmob, cross linked to R506 by a Carba link, any non-crosslinking aa or mimetic.

In some preferred embodiments, R503 is a Cysteine side chain analog [—(CR2)n-S, or —(CR2)n-H; where n is C1-C10, R is any atom and H is a reactive group], an alpha, beta or gamma amino acid capable of forming a crosslink with Cys14 (R508) via a side chain functional group (see side chains, above), an amino acid mimetic, such as 2-carboxy-3-thiopiperidine, which constrain the dihedral angles or the side chain to favorable configurations. R503 is preferably C crosslinked to C at R508 or any other moiety crosslinked to R508.

In some preferred embodiments, R504 is a single amino acid (all types), dipeptide, dipeptide mimetic and chain links, particularly structures with 4-8 atoms bridging the gap between R503 and R505, most preferably structures with 6 atoms bridging the gap between R503 and R505. Preferred amino acids for R504 are sarcosine, ornithine and lysine. Glu7 preferred amino acid replacements are Gln, Gly, Ser, Ala, Pro, Asp, Asn and L-octahydroindole-2-carboxyilic acid, and their N-alkyl, N-hydroxyl, or N-aryl analogs. Leu8 preferred amino acid replacements are Ile, Norleucine, Met, Val, Phe, Trp, Tyr, Gln, Gly, Ala, Pro and L-1,2,3,4-tetrahydroisoquinoline-3-carboxyilic acid, and their N-alkyl, N-hydroxyl, or N-aryl analogs. R504 is preferably a dipeptide such as E-L, or E-NmethylLeu.

In some preferred embodiments, R505 is a single amino acid (all types), preferably hydrophobic or neutral ones, and their N-alkyl, N-hydroxyl, or N-aryl analogs, more preferably Ala, N(Me)-Ala, Thr, Leu, N(Me)-Leu, Phe and blocked Cysteine, Serine and Threonine, an amino acid mimetic, such as L-1,2,3,4-tetrahydroisoquinoline-3-carboxyilic acid, which constrain the dihedral angles or the side chain to favorable configurations. In some preferred embodiments, R505 may be comprised of amino acids or organic molecules with a hydrophobicity of at least −2.0 (Glutamic acid is the lowest native AA with a value of −1.22), and preferably a value greater than zero; and more preferably a value greater than one. Hydrophobicity is determined by the method of Sweet and Eisenberg (Sweet R. M., Eisenberg D., J. Mol. Biol. 171:479-488 (1983) which is incorporated herein by reference). R505 is preferably A L, T, F, V, I, Y, NmethylLeu, NmethylAlam, and NmethylVal.

In some preferred embodiments, R506 is a single amino acid (all types), or an N-alkyl, N-hydroxyl, or N-aryl analog of one, an amino acid mimetic, such as which constrain the dihedral angles or the side chain to favorable configurations. R506 is preferably C cross linked to R502, blocked C such as Cmob, cross linked to R502 by a Carba link any non-crosslinking amino acid or mimetic.

In some preferred embodiments, R507 is a dipeptide mimetic, such as bicycle-L-seryl-proline, Btd, APM, ACTB, or ACDN

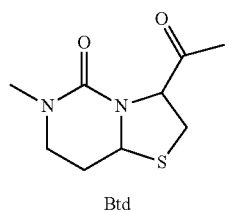

Btd

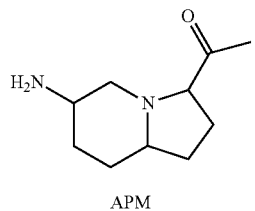

APM

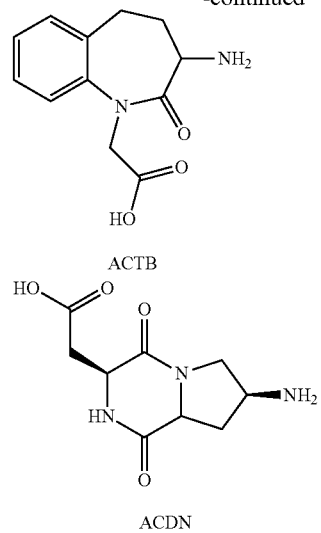

ACTB

ACDN

In some embodiments, R507 is X-Y-Z wherein

X is a single amino acid (all types), preferably Asn, Asp, Ala, His, GlnGly, beta-Alanine), or a short one (Ala, Ser, Thr, Asp), and their N-alkyl, N-hydroxyl, or N-aryl analogs or a synthetic amino acids, preferably Isoasparagine or beta alanine.

Y is a single amino acids (all types), preferably Pro, Ile, Ala, Val (both D and L) and their N-alkyl, N-hydroxyl, or N-aryl analogs. Synthetic amino acids, such as homoPro, Nipecotic acid, isonipecotic acid, Oic, Tic, Aib, aminobenzoate, carboxypiperidine, azetidine carboxylate and aminocyclopentene carboxylic acid. Amino acid mimetics, such as L-1,2,3,4-tetrahydroisoquinoline-3-carboxylic acid, which constrain the dihedral angles or the side chain to favorable configurations.

Z is a single amino acid (all types), preferably with no sidechain (Gly, beta-Alanine), or a short one (Ala, Ser, Thr, Asp), and their N-alkyl, N-hydroxyl, or N-aryl analogs, more preferably Ala, N(Me)-Ala, and Gly.

R507 is preferably a tripeptide N-P-A.

In some preferred embodiments, R508 is a Cysteine side chain analog [—(CR2)n-S, or —(CR2)n-H; where n is C1-C10, R is any atom and H is a reactive group], an alpha, beta or gamma amino acids capable of forming a crosslink with Cys6 (R503) via a side chain functional group (see side chains, above), an amino acid mimetic, such as 2-carboxy-3-thiopiperidine, which constrain the dihedral angles or the side chain to favorable configurations. R508 is preferably C crosslinked to C at R503 or any other moiety crosslinked to R503.

In some preferred embodiments, R509 is preferably cleavable or otherwise degradable in vivo such that it is converted from a compound of the invention to an agonist. Examples of cleavable tails are NPAAAGCacmY, and ST11-18 with a change at 17 to remove crosslinking function.

The present invention also relates to compounds that are Loop B compound of the inventions which are Loop B compounds that have nondegardable tails. The present invention relates to compounds having Formula (VI):

R601-R602-R603-R604-R605-R606-R607-R608-R609      (VI)

wherein

R601 is combination of 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof;

R602 is a natural amino acid, blocked amino acid, synthetic amino acid, derivatized amino acid, or an amino acid mimetic wherein R602 may crosslink with R606;

R603 is a natural amino acid, blocked amino acid, synthetic amino acid, derivatized amino acid or amino acid mimetic that crosslinks with R608;

R604 is one or two natural amino acids, one or two blocked amino acids, one or two synthetic amino acids, one or two derivatized amino acids, one or two amino acid mimetics, or a dipeptide mimetic or combinations thereof, wherein R604 forms a $3_{10}$-helix turn group linking R603 to R605;

R605 is a natural amino acid, blocked amino acid, synthetic amino acid, derivatized amino acid or amino acid mimetic that does not crosslink with R609

R606 is a natural amino acid, blocked amino acid, synthetic amino acid, derivatized amino acid, or an amino acid mimetic wherein R606 may crosslink with R602;

R607 is one, two or three natural amino acids, one, two or three blocked amino acids, one, two or three amino acid mimetics, or a tripeptide mimetic or combinations thereof, wherein R607 forms a beta turn group linking R606 to R608

R608 is a natural amino acid, blocked amino acid, synthetic amino acid, derivatized amino acid or amino acid mimetic that crosslinks with R603;

R609 is 1-50 natural amino acids, 1-50 derivatized amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof that does not crosslink to R605 and is non-degradable in vivo.

In some preferred embodiments, R601 is preferably 1-50 natural amino acids, 1-50 blocked amino acids, 1-50 synthetic amino acids, 1-50 derivatized amino acids; 1-50 amino acid mimetics, a 1-50 alkyls, one or more 1-50 substituted alkyls, one or more 1-50 aryls, one or more 1-50 substituted aryls, one or more 1-50 alkylaryls, one or more 1-50 substituted alkylaryls or combinations thereof. In some embodiments, R601 is 0-20 amino acids. In some embodiments R601 is smaller than 1000 daltons. In some embodiments, R601 is Y, NTFY, SSSNY, SSDWDY, ID, PN, or QE.

In some preferred embodiments, R602 is a Cysteine side chain analog [—(CR2)n-S, or —(CR2)n-H; where n is C1-C10, R is any atom and H is a reactive group], or aryl, alkyl and arylalkyl groups that may or may not crosslink to Cys10 (R606). In some embodiments, R602 is 2-carboxy-3-bromo-pyridine, 2-bromo-benzoic acid, 2-bromo-cyclohexanoic acid. R602 is preferably C cross linked to R606, blocked C such as Cmob, cross linked to R606 by a Carba link, any non-crosslinking aa or mimetic.

In some preferred embodiments, R603 is a Cysteine side chain analog [—(CR2)n-S, or —(CR2)n-H; where n is C1-C10, R is any atom and H is a reactive group], an alpha, beta or gamma amino acid capable of forming a crosslink with Cys14 (R608) via a side chain functional group (see side chains, above), an amino acid mimetic, such as 2-carboxy-3-thiopiperidine, which constrain the dihedral angles or the side chain to favorable configurations. R603 is preferably C crosslinked to C at R608 or any other moiety crosslinked to R608.

In some preferred embodiments, R604 is a single amino acid (all types), dipeptide, dipeptide mimetic and chain links, particularly structures with 4-8 atoms bridging the gap between R603 and R605, most preferably structures with 6 atoms bridging the gap between R603 and R605. Preferred amino acids for R604 are sarcosine, ornithine and lysine. Glu7 preferred amino acid replacements are Gln, Gly, Ser, Ala, Pro, Asp, Asn and L-octahydroindole-2-carboxyilic acid, and their N-alkyl, N-hydroxyl, or N-aryl analogs. Leu8 preferred amino acid replacements are Ile, Norleucine, Met, Val, Phe, Trp, Tyr, Gln, Gly, Ala, Pro and L-1,2,3,4-tetrahydroisoquinoline-3-carboxyilic acid, and their N-alkyl, N-hydroxyl, or N-aryl analogs. R604 is preferably a dipeptide such as E-L, or E-NmethylLeu.

In some preferred embodiments, R605 is a single amino acid (all types), preferably hydrophobic or neutral ones, and their N-alkyl, N-hydroxyl, or N-aryl analogs, more preferably Ala, N(Me)-Ala, Thr, Leu, N(Me)-Leu, Phe and blocked Cysteine, Serine and Threonine, an amino acid mimetic, such as L-1,2,3,4-tetrahydroisoquinoline-3-carboxyilic acid, which constrain the dihedral angles or the side chain to favorable configurations. In some preferred embodiments, R605 may be comprised of amino acids or organic molecules with a hydrophobicity of at least −2.0 (Glutamic acid is the lowest native AA with a value of −1.22), and preferably a value greater than zero; and more preferably a value greater than one. Hydrophobicity is determined by the method of Sweet and Eisenberg (Sweet R. M., Eisenberg D., J. Mol. Biol. 171:479-488 (1983) which is incorporated herein by reference). R605 is preferably A L, T, F, V, I, Y, NmethylLeu, NmethylAlam, and NmethylVal.

In some preferred embodiments, R606 is a single amino acid (all types), or an N-alkyl, N-hydroxyl, or N-aryl analog of one, an amino acid mimetic, such as which constrain the dihedral angles or the side chain to favorable configurations. R606 is preferably C cross linked to R602, blocked C such as Cmob, cross linked to R602 by a Carba link any non-crosslinking amino acid or mimetic.

In some preferred embodiments, R607 is a dipeptide mimetic, such as bicycle-L-seryl-proline, Btd, APM, ACTB, or ACDN

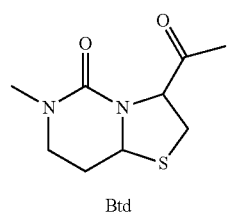

Btd

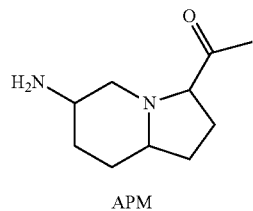

APM

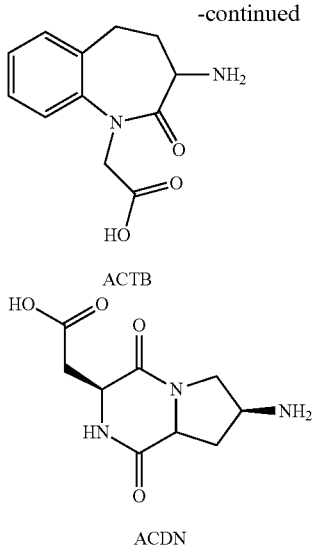

ACTB

ACDN

In some embodiments, R607 is X-Y-Z wherein

X is a single amino acid (all types), preferably Asn, Asp, Ala, His, GlnGly, beta-Alanine), or a short one (Ala, Ser, Thr, Asp), and their N-alkyl, N-hydroxyl, or N-aryl analogs or a synthetic amino acids, preferably Isoasparagine or beta alanine.

Y is a single amino acids (all types), preferably Pro, Ile, Ala, Val (both D and L) and their N-alkyl, N-hydroxyl, or N-aryl analogs. Synthetic amino acids, such as homoPro, Nipecotic acid, isonipecotic acid, Oic, Tic, Aib, aminobenzoate, carboxypiperidine, azetidine carboxylate and aminocyclopentene carboxylic acid. Amino acid mimetics, such as L-1,2,3,4-tetrahydroisoquinoline-3-carboxylic acid, which constrain the dihedral angles or the side chain to favorable configurations.

Z is a single amino acid (all types), preferably with no sidechain (Gly, beta-Alanine), or a short one (Ala, Ser, Thr, Asp), and their N-alkyl, N-hydroxyl, or N-aryl analogs, more preferably Ala, N(Me)-Ala, and Gly.

R607 is preferably a tripeptide N-P-A.

In some preferred embodiments, R608 is a Cysteine side chain analog [—(CR2)n-S, or —(CR2)n-H; where n is C1-C10, R is any atom and H is a reactive group], an alpha, beta or gamma amino acids capable of forming a crosslink with Cys6 (R503) via a side chain functional group (see side chains, above), an amino acid mimetic, such as 2-carboxy-3-thiopiperidine, which constrain the dihedral angles or the side chain to favorable configurations. R608 is preferably C crosslinked to C at R603 or any other moiety crosslinked to R603.

In some preferred embodiments, R609 is non-degradable in vivo such that it is not converted from a compound of the invention to an agonist. Examples of cleavable tails are organics or non-naturally occurring amino-acids.

Compounds may be produced synthetically or recombinantly. Peptides and conjugated compositions or portions thereof which are peptides may be prepared using the solid-phase synthetic technique initially described by Merrifield, in J. Am. Chem. Soc., 15:2149-2154 (1963). Other peptide synthesis techniques may be found, for example, in M. Bodanszky et al., (1976) Peptide Synthesis, John Wiley & Sons, 2d Ed.; Kent and Clark-Lewis in Synthetic Peptides in Biology and Medicine, p. 295-358, eds. Alitalo, K., et al. Science Publishers, (Amsterdam, 1985); as well as other reference works known to those skilled in the art. A summary of peptide synthesis techniques may be found in J. Stuart and J. D. Young, Solid Phase Peptide Synthelia, Pierce Chemical Company, Rockford, Ill. (1984), which is incorporated herein by reference. The synthesis of peptides by solution methods may also be used, as described in The Proteins, Vol. II, 3d Ed., p. 105-237, Neurath, H. et al., Eds., Academic Press, New York, N.Y. (1976). Appropriate protective groups for use in such syntheses will be found in the above texts, as well as in J. F. W. McOmie, Protective Groups in Organic Chemistry, Plenum Press, New York, N.Y. (1973), which is incorporated herein by reference. In general, these synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

According to some embodiments of the invention, compounds of the invention are conjugated to a detectable moiety, making them particular useful as imaging agents or diagnostic test reagents. Detectable moieties include radioactive as well as non-radioactive moieties.

Examples of radioactive include substitution of atoms of the compound with a radioactive isotope of such atoms. Alternatively, the radioactive moiety may be a radionuclide or a radioactive compound which is conjugated to the compound, either directly or through use of a linker. Examples of non-radioactive compounds include a GCC compound of the invention conjugated to a detectable, non-radioactive moiety. In some embodiments the GCC compound of the invention is linked to a linker that forms a bond or complex with a detectable moiety. include a non-radioactive compound which is conjugated to the compound, either directly or through use of a linker.

Examples of moieties which can be conjugated to the compounds of the invention of include a radionuclide, such as for example, $^{125}$I, $^{43}$K, $^{52}$Fe, $^{57}$Co, $^{67}$Cu, $^{67}$Ga, $^{68}$Ga, $^{77}$Br, $^{81}$Rb/$^{81}$MKr, $^{87}$MSr, $^{99}$MTc, $^{111}$In, $^{123}$I, $^{125}$I, $^{127}$Cs, $^{129}$Cs, $^{131}$I, $^{132}$I, $^{197}$Hg, $^{203}$Pb and $^{206}$206Bi, $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb and $^{212}$Bi, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193}$MPt, $^{197}$Hg; beta negative and/or auger emitters; enzymes, such as for example, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase, fluorescent labels, such as for example, fluorescein isothiocyanate, rhodamine, phycoerythrin, phycocyanin, allophycocyanin, o-phthaldehyde and fluorescamine; fluorescence-emitting metals such as $^{152}$Eu, or others of the lanthanide series; metals using such metal chelating groups as diethylenetriaminepentaacetic acid (DTPA) or ethylenediamine-tetraacetic acid (EDTA); chemiluminescent labels such as for example luminol, isoluminol, theromatic acridinium ester, imidazole, acridinium salt and oxalate ester; and bioluminescent labels such as for example luciferin, luciferase and aequorin. Examples also include chemotherapeutics, such as for example, methotrexate (amethopterin), doxorubicin (adrimycin), daunorubicin, cytosinarabinoside, etoposide, 5-4 fluorouracil, melphalan, chlorambucil, and other nitrogen mustards (e.g. cyclophosphamide), cis-platinum, vindesine (and other vinca alkaloids), mitomycin and bleomycin. Other chemotherapeutics include: purothionin (barley flour oligopeptide), macromomycin. 1,4-benzoquinone derivatives and trenimon; toxins such as for examples ricin, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin; inactive prodrug which can be converted by the enzyme into an active drug such as a prodrug, such as for example etoposidephosphate, that can be converted to an active drug by an enzyme such as for example alkaline phosphatase/etoposidephosphate; radiosensitizing agents such as for example nitroimidazoles, metronidazole and misonidazole; radionuclides useful as toxins in radiation therapy such as for example $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb and $^{212}$Bi, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193}$MPt, $^{197}$Hg; and all beta negative and/or auger emitters; heavy metal such as iron chelates, chelates of gadolinium or manganese; positron emitters of oxygen, nitrogen, iron, carbon, or gallium; radionuclides useful in imaging procedures such as for example $^{43}$K, $^{52}$Fe, $^{57}$Co, $^{67}$Cu, $^{67}$Ga, $^{68}$Ga, $^{77}$Br, $^{81}$Rb/$^{81}$MKr, $^{87}$MSr, $^{99}$MTc, $^{111}$In, $^{113}$MIn, $^{123}$I, $^{125}$I, $^{127}$Cs, $^{129}$Cs, $^{131}$I, $^{132}$I, $^{197}$Hg, $^{203}$Pb and $^{206}$206Bi. Additional examples include photodynamic agents such as fluorophore or porphyrins. Porphyrin may include hematoporphyrin derivative (HPD) and porfimer sodium (Photofrin®). A second generation photosensitizers is BPD verteporfin. In some embodiments the fluorophore is tetramethylrotamine.

Compositions of the Invention

According to some embodiments of the invention, compositions are provided which comprise conjugated or non-conjugated compounds as well as kits.

Compositions comprising conjugated compounds useful for in vivo imaging or therapeutics are provided as pharmaceutical compositions. In some embodiments, the compounds are provided as pharmaceuticals adapted for oral administration. In such embodiments, the composition may be in the form of a tablet, capsule or liquid. In some embodiments, the tablet or capsule may be enterically coated or otherwise adapted to pass the stomach intact for delivery to the intestine. In some embodiments, the compositions are sterile, pyrogen free compositions particularly suitable as injectables. Some may be adapted for topical application such as spray on imaging compositions. In some embodiments, the pharmaceutical compositions comprise the compounds of the invention in combination with a liposome comprising a therapeutic compound. In some preferred embodiments, the compound of the invention is provided on the exterior of a liposome that comprises a chemotherapeutic, gene therapeutic, antisense compound, toxin or radioactive substance.

In some embodiments, the compound is provided in a composition adapted for use as an in vitro/ex vivo reagent such as a diagnostic reagent.

The pharmaceutical composition of the present invention may be formulated by one having ordinary skill in the art. Suitable pharmaceutical carriers are described in Remington's Pharmaceutical Sciences, A. Osol, a standard reference text in this field, which is incorporated herein by reference. In carrying out methods of the present invention, unconjugated and conjugated compounds of the present invention can be used alone or in combination with other diagnostic, therapeutic or additional agents. Such additional agents include excipients such as coloring, stabilizing agents, osmotic agents and antibacterial agents.

For parenteral administration, the peptides of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. The compositions are made free of pyrogens by commonly used techniques. For example, a parenteral composition suitable for administration by injection is prepared by dissolving 1.5% by weight of active ingredient in 0.9% sodium chloride solution.

The pharmaceutical compositions of the present invention may be administered by any means that enables the active agent to reach the targeted cells. These methods include, but are not limited to, oral, topical, intradermal, subcutaneous, intravenous, intramuscular and intraparenteral modes of administration. The compounds may be administered singly or in combination with other compounds. The compounds of the invention are preferably administered with a pharmaceutically acceptable carrier selected on the basis of the selected route of administration and standard pharmaceutical practice.

Methods of Diagnosing, Imaging and Treating Cancer

The present invention relates to compounds and methods for in vivo imaging and treatment of tumors originating from the alimentary canal, particularly Barrett's esophagus, primary and metastatic stomach and esophageal tumors and metastatic colorectal tumors.

Carcinomas derived from the colorectal cells, stomach or esophagus express GCC. The expression of GCC by such tumors enables this protein to be a specific biomarker for the presence of cancer cells in extra-intestinal tissues and blood. Indeed, this characteristic permits the detection of GCC using the compounds of the invention in a diagnostic test to diagnose and stage patients with colorectal, stomach or esophageal cancer and follow patients after surgery for evidence of recurrent disease in their blood as well as to detect colorectal, stomach and esophageal cancers. Further, the GCC may be targeted with some embodiments of the invention in order to deliver the active agent, such as a detectable agent or a chemotherapeutic to tumor cells in vivo.

Detection of the expression of GCC employing molecular techniques can be employed to diagnose and stage patients, follow the development of recurrence after surgery and/or remission, and, potentially, screen normal people for the development of colorectal, stomach or esophageal cancer.

In individuals suffering from colorectal cancer, the cancer cells are often derived from cells that produce and display the GCC and these cancer cells continue to produce GCC. It has been observed that GCC is expressed by colorectal cancer cells. Likewise, GCC is expressed by stomach and esophageal cancer cells.

The expression of GCC by colorectal tumor cells provides a detectable target for in vitro screening, monitoring and staging as well as a target for in vivo delivery of conjugated compositions that comprise active agents for the imaging and treatment.

The expression of GCC by stomach and esophageal tumor cells provides a detectable target for in vitro screening, monitoring and staging as well as a target for in vivo delivery of conjugated compositions that comprise active agents for the imaging and treatment.

The expression of GCC by esophageal cells is indicative of Barrett's esophagus. GCC provides a detectable target for in vitro screening, monitoring and staging as well as a target for in vivo delivery of conjugated compositions that comprise active agents for the imaging and treatment.

Preferred Uses

Compounds according to the invention that are GCC compound of the inventions bind to GCC but do not activate the GCC signal pathway. Accordingly, such compounds prevent diarrhea in humans that is induced by ST producing organisms, which is especially relevant in developing countries where such organisms are common. By administering compounds prophylactically on a regular basis, such compounds can be used to prevent diarrhea and the growth retardation that occurs in children in developing countries due to chronic ST-induced diarrhea. The compounds are particularly useful to prevent travelers' diarrhea when taken by individuals who will be exposed to organisms which produce ST such as those traveling to countries where such organisms are endemic. The compounds are useful to prevent scours and other diarrheal diseases in animals.

The compounds are also useful therapeutically. For example, the compounds may be used to treat diarrhea known to be ST induced as well as secretory diarrhea of unknown etiology. Similarly, they may be used to treat irritable bowel syndrome and other forms of diarrhea including, but not limited to, diarrhea associated with inflammatory bowel disease, sprue, etc.

Because compounds of formula bind to GCC, the may be used to detect, image or treat cancer. Compounds may be used in methods for early detection of neoplastic transformation within the upper GI-tract as a ligand to identify GCC expression. Similarly, screening, diagnosis, staging and post-operative surveillance of colorectal tumors may be undertaken using compounds which serve as a ligand to identify GCC expression. The compounds may be used in diagnostic and therapeutic targeting of primary and metastatic esophageal and gastric tumors and metastatic colorectal tumors as a ligand for GCCm and to facilitate intestinal recovery from insult e.g. intestinal adaptation, wherein the epithelium requires regeneration including, but not limited to, ischemic insult, chemical insult, chemotherapy, trauma, and surgery.

Compounds according to the invention that are GCC agonists bind to GCC and activate the GCC signal pathway. Accordingly, such compounds treat Barrett's esophagus as well as primary and metastatic stomach and esophageal cancer as well as metastatic cancer. The compounds are useful therapeutically alone or in combination with other therapeutic agents.

Because compounds of formula bind to GCC, the may be used to detect, image or treat cancer. Compounds may be used in methods for early detection of neoplastic transformation within the upper GI-tract as a ligand to identify GCC expression. Similarly, screening, diagnosis, staging and post-operative surveillance of colorectal tumors may be undertaken using compounds which serve as a ligand to identify GCC expression. The compounds may be used in diagnostic and therapeutic targeting of primary and metastatic esophageal and gastric tumors and metastatic colorectal tumors as a ligand for GCCm and to facilitate intestinal recovery from insult e.g. intestinal adaptation, wherein the epithelium requires regeneration including, but not limited to, ischemic insult, chemical insult, chemotherapy, trauma, and surgery.

In Vitro Diagnostics

According to some embodiments of the invention, compositions, kits and in vitro methods are provided for screening, diagnosing and analyzing patients and patient samples to detect evidence of GCC expression by cells outside of the intestinal tract wherein the expression of GCC may be suggestive of metastasized colorectal cancer or primary or metastatic stomach or esophageal cancer. In patients suspected of having metastasized colorectal cancer or primary or metastatic stomach or esophageal cancer evidence of GCC expression by cells outside of the intestinal tract is indicative of metastasized colorectal cancer or primary or metastatic stomach or esophageal cancer and can be used in the diagnosis, monitoring and staging of such patients. Furthermore, the present invention relates to methods, compositions and kits useful in the in vitro screening, and analysis of patient and patient samples to detect evidence of GCC expression by tumor cells outside of the intestinal tract wherein the presence of cells that express GCC suggests or confirms that a tumor is of colorectal or stomach or esophageal cancer origin. In an additional aspect of the invention, compositions, kits and methods are provided which are useful to visualize metastasized colorectal cancer or primary or metastatic stomach or esophageal cancer cells.

In vitro screening and diagnostic compositions, methods and kits can be used in the monitoring of individuals who are in high risk groups for colorectal, stomach or esophageal cancer such as those who have been diagnosed with localized disease and/or metastasized disease and/or those who are genetically linked to the disease. In vitro screening and diagnostic compositions, methods and kits can be used in the monitoring of individuals who are undergoing and/or have been treated for primary colorectal, stomach or esophageal cancer to determine if the cancer has metastasized. In vitro screening and diagnostic compositions, methods and kits can be used in the monitoring of individuals who are undergoing and/or have been treated for colorectal, stomach or esophageal cancer to determine if the cancer has been eliminated. In vitro screening and diagnostic compositions, methods and kits can be used in the monitoring of individuals who are otherwise susceptible, i.e. individuals who have been identified as genetically predisposed such as by genetic screening and/or family histories. Advancements in the understanding of genetics and developments in technology as well as epidemiology allow for the determination of probability and risk assessment an individual has for developing stomach or esophageal cancer. Using family health histories and/or genetic screening, it is possible to estimate the probability that a particular individual has for developing certain types of cancer including colorectal, stomach or esophageal cancer. Those individuals that have been identified as being predisposed to developing a particular form of cancer can be monitored or screened to detect evidence of colorectal, stomach or esophageal cancer. Upon discovery of such evidence, early treatment can be undertaken to combat the disease. Accordingly, individuals who are at risk for developing colorectal, stomach or esophageal cancer may be identified and samples may be isolated form such individuals. The invention is particularly useful for monitoring individuals who have been identified as having family medical histories which include relatives who have suffered from colorectal, stomach or esophageal cancer. Likewise, the invention is particularly useful to monitor individuals who have been diagnosed as having colorectal, stomach or esophageal cancer and, particularly those who have been treated and had tumors removed and/or are otherwise experiencing remission including those who have been treated for colorectal, stomach or esophageal cancer.

In vitro screening and diagnostic compositions, methods and kits can be used in the analysis of tumors. Expression of GCC is a marker for cell type and suggests the origin of adenocarcinoma of unconfirmed origin may be colorectal, stomach or esophageal tumors. Detection of GCC expression can also be used to assist in an initial diagnosis of colorectal, stomach or esophageal cancer or to confirm such diagnosis. Tumors believed to be colorectal, stomach or esophageal in origin can be confirmed as such using the compositions, methods and kits of the invention.

In vitro screening and diagnostic compositions, kits and methods of the invention can be used to analyze tissue samples from the stomach or esophagus to identify primary stomach or esophageal cancer.

In vitro screening and diagnostic compositions, kits and methods of the invention can be used to analyze tissue samples from the colon to detect the amount of invasion by primary colorectal cancer into the intestinal tissue.

According to the invention, compounds are provided which bind to GCC protein. Normal tissue in the body does not have GCC protein except cells of the intestinal tract. The expression of GCC is a marker for cell type and is useful in the identification of colorectal, stomach or esophageal cancer in extra-intestinal samples.

In some embodiments of the invention, non-colorectal tissue and fluid samples or tumor samples may be screened to identify the presence or absence of GCC protein. The presence of GCC in non-colorectal tissue and fluid samples or on cells from non-colorectal tissue samples suggests possible stomach or esophageal cancer. The presence of GCC in a tumor sample or on tumor cells suggests that the tumor may be colorectal, stomach or esophageal in origin.

Samples may be obtained from resected tissue or biopsy material including needle biopsy. Tissue section preparation for surgical pathology may be frozen and prepared using standard techniques. Binding assays on tissue sections are performed in fixed cells. It is also contemplated that tumor samples in body fluids such as blood, urine, lymph fluid, cerebral spinal fluid, amniotic fluid, vaginal fluid, semen and stool samples may also be screened to determine if such tumors are colorectal, stomach or espophageal in origin.

Non-colorectal tissue samples may be obtained from any tissue except those of the colorectal tract, i.e. the intestinal tract below the small intestine (i.e. the large intestine (colon), including the cecum, ascending colon, transverse colon, descending colon, and sigmoid colon, and rectum) and additionally the duodenum and small intestine (jejunum and ileum). The normal cells of all tissue except those of the colorectal tract do not express GCC. Thus if GCC protein are detected in non-colorectal samples, the possible presence of colorectal, stomach or esophageal cancer cells is suggested. In some preferred embodiments, the tissue samples are lymph nodes.

Tissue samples may be obtained by standard surgical techniques including use of biopsy needles. One skilled in the art would readily appreciate the variety of test samples that may be examined for GCC and recognize methods of obtaining tissue samples.

Examples of body fluid samples include blood, urine, lymph fluid, cerebral spinal fluid, amniotic fluid, vaginal fluid and semen. In some preferred embodiments, blood is used as a sample of body fluid. Cells may be isolated from fluid sample such as centrifugation. One skilled in the art would readily appreciate the variety of test samples that may be examined for GCC. Test samples may be obtained by such methods as withdrawing fluid with a syringe or by a swab. One skilled in the art would readily recognize other methods of obtaining test samples.

In an assay using a blood sample, the blood plasma may be separated from the blood cells. The blood plasma may be screened for GCC including truncated proteins which are released into the blood when one or more GCC are cleaved from or sloughed off from tumor cells. In some embodiments, blood cell fractions are screened for the presence of colorectal, stomach or esophageal tumor cells. In some embodiments, lymphocytes present in the blood cell fraction are screened by lysing the cells and detecting the presence of GCC protein which may be present as a result of the presence of any stomach or esophageal tumor cells that may have been engulfed by the blood cell. In some preferred embodiments.

The present invention provides methods f detecting the presence of detecting presence of GCC in sample using compounds of the invention as a detectable ligand of GCC. The compounds of the invention used in this assay may be used as research reagents as well as diagnostics since considerable laboratory research is conducted in which GCC presence must be detected. The GCC binding assay uses a detectable compounds to bind to any GCC present and thus indicate the presence of the receptor in a sample.

The present invention also relates to methods of identifying individuals suffering from colorectal, stomach or esophageal cancer by detecting presence of GCC in sample of tumor.

The GCC binding assay can be readily performed by those having ordinary skill in the art using readily available starting materials. GCC binding assays may be performed a variety of ways but each essentially identify whether or not GCC protein is present in a sample by determining whether or not a detectable compound binds to a receptor in a sample. Briefly, the assay consists of incubating a sample with a constant concentration of compound of the invention such as $1\times10^{-10}$ M to $5\times10^{-10}$ M of $^{125}$I-labeled compound. As a control, a duplicate preparation of a sample known to contain GCC are incubated with a duplicate concentration of $^{125}$I-labeled compound of the invention. Assays are incubated to equilibrium (for example 2 hours) and the sample is analyzed to determine whether or not $^{125}$I-compound of the invention is bound to material in the sample. The $^{125}$I-compound of the invention/sample is passed through a filter which is capable of allowing .sup. $^{125}$I-compound of the invention to pass through but not capable of allowing GCC to pass through. Thus, if GCC is present in the sample, it will bind the $^{125}$I-compound of the invention which will then be trapped by the filter. Detection of $^{125}$I-compound of the invention in the filter indicates the presence of GCC in the sample. In some preferred embodiments, the filter is Whitman GFB glass filter paper. Controls include using samples which are known to contain GCC, e.g. intestinal membranes from rat intestine, human intestine, T84 cells, isolated GCC protein or cells expressing cloned nucleotide sequence encoding GCC.

The compounds of the invention may be prepared routinely by any of the following known techniques. In addition to being conjugated to $^{125}$I, compounds of the invention may be detectable by binding it to other radionuclides such as: $^{43}$K, $^{52}$Fe, $^{57}$Co, $^{67}$Cu, $^{67}$Ga, $^{68}$Ga, $^{77}$Br, $^{81}$Rb/$^{81}$MKr, $^{87}$MSr, $^{99}$MTc, $^{111}$In, $^{113}$MIn, $^{123}$I, $^{125}$I, $^{127}$Cs, $^{129}$Cs, $^{131}$I, $^{132}$I, $^{197}$Hg, $^{203}$Pb and $^{206}$206Bi, $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb and $^{212}$Bi, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193}$MPt, $^{197}$Hg, as well as all beta negative and/or auger emitters or by binding it to other labels such as fluorescein or enzymes. Each of the labeling means described above for detectably labeling antibodies can be adapted to label compounds of the invention and are considered to be described as such herein.

The compound of the invention may be detectably labeled is by linking it to an enzyme. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. One skilled in the art would readily recognize other enzymes which may also be used. It is also possible to label the compound with a fluorescent compound. When the fluorescent-labeled antibody is exposed to light of the proper wave length, its presence can be detected due to its fluorescence. Among the most commonly used fluorescent labeling compounds are fluorescein isothiocyanate, rhodamine, phycoerythrin, phycocyanin, allophycocyanin, o-phthaldehyde and fluorescamine. One skilled in the art would readily recognize other fluorescent compounds which may also be used. Compounds of the invention can also be detectably labeled using fluorescence-emitting metals such as $^{152}$Eu, or others of the lanthanide series. These metals can be attached to the protein-specific antibody using such metal chelating groups as diethylenetriaminepentaacetic acid (DTPA) or ethylenediamine-tetraacetic acid (EDTA). One skilled in the art would readily recognize other fluorescence-emitting metals as well as other metal chelating groups which may also be used. Compounds of the inventions can also be detectably labeled by coupling to a chemiluminescent compound. The presence of the chemiluminescent-labeled antibody is determined by detecting the presence of luminescence that arises during the course of a chemical reaction. Examples of particularly useful chemoluminescent labeling compounds are luminol, isoluminol, theromatic acridinium ester, imidazole, acridinium salt and oxalate ester. One skilled in the art would readily recognize other chemiluminescent compounds which may also be used. Likewise, a bioluminescent compound may be used to label antibodies. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. One skilled in the art would readily recognize other bioluminescent compounds which may also be used.

Detection of the compound of the invention may be accomplished by a scintillation counter if, for example, the detectable label is a radioactive gamma emitter. Alternatively, detection may be accomplished by a fluorometer if, for example, the label is a fluorescent material. In the case of an enzyme label, the detection can be accomplished by colorometric methods which employ a substrate for the enzyme. Detection may also be accomplished by visual comparison of the extent of enzymatic reaction of a substrate in comparison with similarly prepared standards. One skilled in the art would readily recognize other appropriate methods of detection which may also be used.

Positive and negative controls may be performed in which known amounts of GCC protein and no GCC protein, respectively, are added to assays being performed in parallel with the test assay. One skilled in the art would have the necessary knowledge to perform the appropriate controls. In addition, the kit may comprise instructions for performing the assay. Additionally the kit may optionally comprise depictions or photographs that represent the appearance of positive and negative results.

Anti-compound of the invention antibodies may be generated, detectably labeled in a manner described above for labeling compound of the invention, and used to detect compound of the invention bound to GCC in the sample. Anti-compound of the invention antibodies may also be designed for immuno-PCR, immuno-RNA amplification, magnetic sorting etc.

Kits include containers comprising detectable compound of the inventions together with containers having positive and/or negative controls, i.e. samples which contain GCC and samples which contain no GCC, respectively. The detectable compound of the inventions is preferably labeled. Additional components in some kits include solid support, buffer, and instructions for carrying out the assay. Additionally the kit may optionally comprise depictions or photographs that represent the appearance of positive and negative results.

The GCC binding assay is useful for detecting GCC in homogenized tissue samples and body fluid samples including the plasma portion.

In Vivo Imaging and Therapeutics

According to some embodiments of the invention, compositions and in vivo methods are provided for detecting, imaging, or treating metastatic colorectal cancer and primary and/or metastatic stomach or esophageal tumors in an individual.

When the conjugated compositions of the present invention are administered outside the intestinal tract such as when administered in the circulatory system, they remain segregated from the cells that line the intestinal tract and will bind only to cells outside the intestinal tract which express GCC. The conjugated compositions will not bind to the normal cells but will bind to metastatic colorectal cancer cells and primary and/or metastatic stomach or esophageal cells. Thus, the active moieties of conjugated compositions administered outside the intestinal tract are delivered to cells which express GCC such as metastatic colorectal cancer cells and primary and/or metastatic stomach or esophageal cancer cells.

Therapeutic and diagnostic pharmaceutical compositions useful in the present invention include conjugated compounds that specifically target cells that express GCC. These conjugated compounds include moieties that bind to GCC which do not bind to cells of normal tissue in the body except cells of the intestinal tract since the cells of other tissues do not express GCC.

Unlike normal colorectal cells, cancer cells that express GCC are accessible to substances administered outside the intestinal tract, for example administered in the circulatory system. The only GCC in normal tissue exist in the apical membranes of intestinal mucosa cells and thus effectively isolated from the targeted cancer chemotherapeutics and imaging agents administered outside the intestinal tract by the intestinal mucosa barrier. Thus, metastatic colorectal cancer and primary and/or metastatic stomach or esophageal cancer cells may be targeted by conjugated compounds of the present invention by introducing such compounds outside the intestinal tract such as for example by administering pharmaceutical compositions that comprise conjugated compounds into the circulatory system.

One having ordinary skill in the art can identify individuals suspected of suffering from metastatic colorectal cancer and primary and/or metastatic stomach or esophageal cancer. In those individuals diagnosed with colorectal, stomach or esophageal cancer, it is not unusual and in some cases standard therapy to suspect metastasis and aggressively attempt to eradicate metastasized cells. The present invention provides pharmaceutical compositions and methods for imaging and thereby will more definitively diagnose primary and metastastic disease. Further, the present invention provides pharmaceutical compositions comprising therapeutic agents and methods for specifically targeting and eliminating metastatic colorectal cancer and primary and/or metastatic stomach or esophageal cancer cells. Further, the present invention provides pharmaceutical compositions that comprise therapeutics and methods for specifically eliminating metastatic colorectal cancer and primary and/or metastatic stomach or esophageal cancer cells.

The pharmaceutical compositions which comprise conjugated compositions of the present invention may be used to diagnose or treat individuals suffering from metastatic colorectal cancer and primary and/or metastatic stomach or esophageal tumors.

The present invention relies upon the use of a compounds of the invention in a conjugated composition. The compounds of the invention are essentially a portion of the conjugated composition which acts as a ligand to GCCI and thus specifically binds to it. The conjugated composition also includes an active moiety which is associated with the compounds of the invention; the active moiety being an active agent which is either useful to image, target, neutralize or kill the cell.

According to some aspects of the present invention, compounds comprise the compound of the invention linked to an active moiety that may be a therapeutic agent or an imaging agent. One having ordinary skill in the art can readily recognize the advantages of being able to specifically target cancer cells with a compound of the invention and conjugate such compound of the invention with many different active agents.

Chemotherapeutics useful as active moieties which when conjugated to a compound of the invention are specifically delivered to cells that express GCC such as metastatic colorectal cancer cells, stomach cancer cells or esophageal cancer cells, are typically small chemical entities produced by chemical synthesis. Chemotherapeutics include cytotoxic and cytostatic drugs. Chemotherapeutics may include those which have other effects on cells such as reversal of the transformed state to a differentiated state or those which inhibit cell replication. Examples of chemotherapeutics include common cytotoxic or cytostatic drugs such as for example: methotrexate (amethopterin), doxorubicin (adrimycin), daunorubicin, cytosinarabinoside, etoposide, 5-4 fluorouracil, melphalan, chlorambucil, and other nitrogen mustards (e.g. cyclophosphamide), cis-platinum, vindesine (and other vinca alkaloids), mitomycin and bleomycin. Other chemotherapeutics include: purothionin (barley flour oligopeptide), macromomycin. 1,4-benzoquinone derivatives and trenimon.

Toxins are useful as active moieties. When a toxin is conjugated to a compound of the invention, the conjugated composition is specifically delivered to a cell that expresses GCC such as metastatic colorectal cancer, stomach cancer or esophageal cancer cells by way of the compound of the invention and the toxin moiety kills the cell. Toxins are generally complex toxic products of various organisms including bacteria, plants, etc. Examples of toxins include but are not limited to: ricin, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin. As discussed above, when protein toxins are employed with compound of the invention peptides, conjugated compositions may be produced using recombinant DNA techniques. Briefly, a recombinant DNA molecule can be constructed which encodes both the compound and the toxin on a chimeric gene. When the chimeric gene is expressed, a fusion protein is produced which includes a compound of the invention and an active moiety. Protein toxins are also useful to form conjugated compounds with compound of the invention through non-peptidyl bonds.

In addition, there are other approaches for utilizing active agents for the treatment of cancer. For example, conjugated compositions may be produced which include a compound of the invention and an active moiety which is an active enzyme. The compound of the invention specifically localizes the conjugated composition to the tumor cells. An inactive prodrug which can be converted by the enzyme into an active drug is administered to the patient. The prodrug is only converted to an active drug by the enzyme which is localized to the tumor. An example of an enzyme/prodrug pair includes alkaline phosphatase/etoposidephosphate. In such a case, the alkaline phosphatase is conjugated to a compound of the invention. The conjugated compound is administered and localizes at the cancer cell. Upon contact with etoposidephosphate (the prodrug), the etoposidephosphate is converted to etoposide, a chemotherapeutic drug which is taken up by the cancer cell. Radiosensitizing agents are substances that increase the sensitivity of cells to radiation. Examples of radiosensitizing agents include nitroimidazoles, metronidazole and misonidazole (see: DeVita, V. T. Jr. in Harrison's Principles of Internal Medicine, p. 68, McGraw-Hill Book Co., N.Y. 1983, which is incorporated herein by reference). The conjugated compound that comprises a radiosensitizing agent as the active moiety is administered and localizes at the metastatic colorectal cancer cell and primary and/or metastatic stomach or esophageal cancer cell. Upon exposure of the individual to radiation, the radiosensitizing agent is "excited" and causes the death of the cell.

Radionuclides may be used in pharmaceutical compositions that are useful for radiotherapy or imaging procedures. Examples of radionuclides useful as toxins in radiation therapy include: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb and $^{212}$Bi. Other radionuclides which have been used by those having ordinary skill in the art include: $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193}$MPt, $^{197}$Hg, all beta negative and/or auger emitters. Some preferred radionuclides include: $^{90}$Y, $^{131}$I, $^{211}$At and $^{212}$Pb/$^{212}$Bi.

According to the present invention, the active moieties may be an imaging agent. Imaging agents are useful diagnostic procedures as well as the procedures used to identify the location of cancer cells. Imaging can be performed by many procedures well-known to those having ordinary skill in the art and the appropriate imaging agent useful in such procedures may be conjugated to a compound of the invention by well-known means. Imaging can be performed, for example, by radioscintigraphy, nuclear magnetic resonance imaging (MRI) or computed tomography (CT scan). The most commonly employed radionuclide imaging agents include radioactive iodine and indium. Imaging by CT scan may employ a heavy metal such as iron chelates. MRI scanning may employ chelates of gadolinium or manganese. Additionally, positron emission tomography (PET) may be possible using positron emitters of oxygen, nitrogen, iron, carbon, or gallium. Example of radionuclides useful in imaging procedures include: $^{43}$K, $^{52}$Fe, $^{57}$Co, $^{67}$Cu, $^{67}$Ga, $^{68}$Ga, $^{77}$Br, $^{81}$Rb/$^{81}$MKr, $^{87}$MSr, $^{99}$MTc, $^{111}$In, $^{113}$MIn, $^{123}$I, $^{125}$I, $^{127}$Cs, $^{129}$Cs, $^{131}$I, $^{132}$I, $^{197}$Hg, $^{203}$Pb and $^{206}$206Bi.

It is preferred that the conjugated compositions be non-immunogenic or immunogenic at a very low level. Accordingly, it is preferred that the compound of the invention be a small, poorly immunogenic or non-immunogenic peptide or a non-peptide.

Compounds of the inventions are conjugated to active agents by a variety of well-known techniques readily performed without undue experimentation by those having ordinary skill in the art. The technique used to conjugate the compound of the invention to the active agent is dependent upon the molecular nature of the compound of the invention and the active agent. After the compound of the invention and the active agent are conjugated to form a single molecule, assays may be performed to ensure that the conjugated molecule retains the activities of the moieties. The competitive binding assay described above may be used to confirm that the compound of the invention retains its binding activity as a conjugated compound. Similarly, the activity of the active moiety may be tested using various assays for each respective type of active agent. Radionuclides retain there activity, i.e. their radioactivity, irrespective of conjugation. With respect to active agents which are toxins, drugs and targeting agents, standard assays to demonstrate the activity of unconjugated forms of these compounds may be used to confirm that the activity has been retained.

Conjugation may be accomplished directly between the compound of the invention and the active agent or linking, intermediate molecular groups may be provided between the compound of the invention and the active agent. Linkers are particularly useful to facilitate conjugation by providing attachment sites for each moiety. Linkers may include additional molecular groups which serve as spacers to separate the moieties from each other to prevent either from interfering with the activity of the other.

One having ordinary skill in the art may conjugate a compound of the invention to a chemotherapeutic drug using well-known techniques. For example, Magerstadt, M. Antibody Conjugates and Malignant Disease. (1991) CRC Press, Boca Raton, USA, pp. 110-152) which is incorporated herein by reference, teaches the conjugation of various cytostatic drugs to amino acids of antibodies. Such reactions may be applied to conjugate chemotherapeutic drugs to compound of the inventions with an appropriate linker. Most of the chemotherapeutic agents currently in use in treating cancer possess functional groups that are amenable to chemical linking directly with proteins. For example, free amino groups are available on methotrexate, doxorubicin, daunorubicin, cytosinarabinoside, cis-platin, vindesine, mitomycin and bleomycin while free carboxylic acid groups are available on methotrexate, melphalan, and chlorambucil. These functional groups, that is free amino and carboxylic acids, are targets for a variety of homobifunctional and heterobifunctional chemical linking agents which can link these drugs directly to the single free amino group of an antibody. For example, one procedure for linking compound of the inventions which have a free amino group to active agents which have a free amino group such as methotrexate, doxorubicin, daunorubicin, cytosinarabinoside, cis-platin, vindesine, mitomycin and bleomycin, or alkaline phosphatase, or protein- or peptide-based toxin employs homobifunctional succinimidyl esters, preferably with carbon chain spacers such as disuccinimidyl suberate (Pierce Co, Rockford, Ill.). In the event that a cleavable conjugated compound is required, the same protocol would be employed utilizing 3,3'-dithiobis(sulfosuccinimidylpropionate; Pierce Co.).

In order to conjugate a compound of the invention that is a peptide or protein to a peptide-based active agent such as a toxin, the compound of the invention and the toxin may be produced as a single, fusion protein either by standard peptide synthesis or recombinant DNA technology, both of which can be routinely performed by those having ordinary skill in the art. Alternatively, two peptides, the compound of the invention and the peptide-based toxin may be produced and/or isolated as separate peptides and conjugated using linkers. As with conjugated compositions that contain chemotherapeutic drugs, conjugation of compound of the invention and toxins can exploit the ability to modify the single free amino group of a compound of the invention while preserving the receptor-binding function of this molecule.

One having ordinary skill in the art may conjugate a compound of the invention to a radionuclide using well-known techniques. For example, Magerstadt, M. (1991) Antibody Conjugates And Malignant Disease, CRC Press, Boca Raton, Fla.; and Barchel, S. W. and Rhodes, B. H., (1983) Radioimaging and Radiotherapy, Elsevier, NY N.Y., each of which is incorporated herein by reference, teach the conjugation of various therapeutic and diagnostic radionuclides to amino acids of antibodies.

The present invention provides pharmaceutical compositions that comprise the conjugated compounds of the invention and pharmaceutically acceptable carriers or diluents. The pharmaceutical composition of the present invention may be formulated by one having ordinary skill in the art. Suitable pharmaceutical carriers are described in Remington's Pharmaceutical Sciences, A. Osol, a standard reference text in this field, which is incorporated herein by reference.

In carrying out methods of the present invention, conjugated compounds of the present invention can be used alone or in combination with other diagnostic, therapeutic or additional agents. Such additional agents include excipients such as coloring, stabilizing agents, osmotic agents and antibacterial agents. Pharmaceutical compositions are preferably sterile and pyrogen free.

The conjugated compositions of the invention can be, for example, formulated as a solution, suspension or emulsion in association with a pharmaceutically acceptable parenteral vehicle. Examples of such vehicles are water, saline, Ringer's solution, dextrose solution, and 5% human serum albumin. Liposomes may also be used. The vehicle may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as either a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions of the present invention may be administered by any means that enables the conjugated composition to reach the targeted cells. In some embodiments, routes of administration include those selected from the group consisting of intravenous, intraarterial, intraperitoneal, local administration into the blood supply of the organ in which the tumor resides or directly into the tumor itself. In addition to an intraoperative spray, conjugated compounds may be delivered intrathecally, intraventrically, stereotactically, intrahepatically such as via the portal vein, by inhalation, and intrapleurally. Intravenous administration is the preferred mode of administration. It may be accomplished with the aid of an infusion pump.

The dosage administered varies depending upon factors such as: the nature of the active moiety; the nature of the conjugated composition; pharmacodynamic characteristics; its mode and route of administration; age, health, and weight of the recipient; nature and extent of symptoms; kind of concurrent treatment; and frequency of treatment.

Because conjugated compounds are specifically targeted to cells with one or more GCC molecules, conjugated compounds which comprise chemotherapeutics or toxins are administered in doses less than those which are used when the chemotherapeutics or toxins are administered as unconjugated active agents, preferably in doses that contain up to 100 times less active agent. In some embodiments, conjugated compounds which comprise chemotherapeutics or toxins are administered in doses that contain 10-100 times less active agent as an active moiety than the dosage of chemotherapeutics or toxins administered as unconjugated active agents. To determine the appropriate dose, the amount of compound is preferably measured in moles instead of by weight. In that way, the variable weight of different compounds of the invention does not affect the calculation. Presuming a one to one ratio of compound of the invention to active moiety in conjugated compositions of the invention, less moles of conjugated compounds may be administered as compared to the moles of unconjugated compounds administered, preferably up to 100 times less moles. Typically, chemotherapeutic conjugates are administered intravenously in multiple divided doses.

Up to 20 gm IV/dose of methotrexate is typically administered in an unconjugated form. When methotrexate is administered as the active moiety in a conjugated compound of the invention, there is a 10- to 100-fold dose reduction. Thus, presuming each conjugated compound includes one molecule of methotrexate conjugated to one compound of the invention, of the total amount of conjugated compound administered, up to about 0.2-2.0 g of methotrexate is present and therefore administered. In some embodiments, of the total amount of conjugated compound administered, up to about 200 mg-2 g of methotrexate is present and therefore administered.

To dose conjugated compositions comprising compounds of the invention linked to active moieties that are radioisotopes in pharmaceutical compositions useful as imaging agents, it is presumed that each compound of the invention is linked to one radioactive active moiety. The amount of radioisotope to be administered is dependent upon the radioisotope. Those having ordinary skill in the art can readily formulate the amount of conjugated compound to be administered based upon the specific activity and energy of a given radionuclide used as an active moiety. Typically 0.1-100 millicuries per dose of imaging agent, preferably 1-10 millicuries, most often 2-5 millicuries are administered. Thus, pharmaceutical compositions according to the present invention useful as imaging agents which comprise conjugated compositions comprising a compound of the invention and a radioactive moiety comprise 0.1-100 millicuries, in some embodiments preferably 1-10 millicuries, in some embodiments preferably 2-5 millicuries, in some embodiments more preferably 1-5 millicuries. Examples of dosages include: $^{131}$I—between about 0.1-100 millicuries per dose, in some embodiments preferably 1-10 millicuries, in some embodiments 2-5 millicuries, and in some embodiments about 4 millicuries; $^{111}$In between about 0.1-100 millicuries per dose, in some embodiments preferably 1-10 millicuries, in some embodiments 1-5 millicuries, and in some embodiments about 2 millicuries; $^{99m}$Tc—between about 0.1-100 millicuries per dose, in some embodiments preferably 5-75 millicuries, in some embodiments 10-50 millicuries, and in some embodiments about 27 millicuries. Wessels B. W. and R. D. Rogus (1984) Med. Phys. 11:638 and Kwok, C. S. et al. (1985) Med. Phys. 12:405, both of which are incorporated herein by reference, disclose detailed dose calculations for diagnostic and therapeutic conjugates which may be used in the preparation of pharmaceutical compositions of the present invention which include radioactive conjugated compounds.

One aspect of the present invention relates to a method of treating individuals suspected of suffering from metastatic colorectal cancer and primary and/or metastatic stomach or esophageal cancer. Such individuals may be treated by administering to the individual a pharmaceutical composition that comprises a pharmaceutically acceptable carrier or diluent and a conjugated compound that comprises a compound of the invention and an active moiety wherein the active moiety is a radiostable therapeutic agent. In some embodiments of the present invention, the pharmaceutical composition comprises a pharmaceutically acceptable carrier or diluent and a conjugated compound that comprises a compound of the invention and an active moiety wherein the active moiety is a radiostable therapeutic agent. In some embodiments of the present invention, the pharmaceutical composition comprises a pharmaceutically acceptable carrier or diluent and a conjugated compound that comprises a compound of the invention and an active moiety wherein the active moiety is a radiostable active agent selected from the group consisting of: methotrexate, doxorubicin, daunorubicin, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, *Pseudomonas* exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole. The individual being treated may be diagnosed as having metastasized colorectal, stomach or esophageal cancer or may be diagnosed as having primary colorectal, stomach or esophageal cancer and may undergo the treatment proactively in the event that there is some metastasis as yet undetected. The pharmaceutical composition contains a therapeutically effective amount of the conjugated composition. A therapeutically effective amount is an amount which is effective to cause a cytotoxic or cytostatic effect on cancer cells without causing lethal side effects on the individual.

One aspect of the present invention relates to a method of treating individuals suspected of suffering from metastatic colorectal cancer and primary and/or metastatic stomach or esophageal cancer. Such individuals may be treated by administering to the individual a pharmaceutical composition that comprises a pharmaceutically acceptable carrier or diluent and a conjugated compound that comprises a compound of the invention and an active moiety wherein the active moiety is a radioactive. In some embodiments of the present invention, the pharmaceutical composition comprises a pharmaceutically acceptable carrier or diluent and a conjugated compound that comprises a compound of the invention and an active moiety wherein the active moiety is a radioactive and the compound of the invention is an antibody. In some embodiments of the present invention, the pharmaceutical composition comprises a pharmaceutically acceptable carrier or diluent and a conjugated compound that comprises a compound of the invention and an active moiety wherein the active moiety is a radioactive agent selected from the group consisting of: $^{47}$Sc, $^{67}$Cu, $^{90}$Y, $^{105}$Pd, $^{123}$I, $^{125}$I, $^{131}$I, $^{186}$Re, $^{188}$Re, $^{199}$Au, $^{211}$At, $^{212}$Pb and $^{212}$Bi, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193}$MPt, $^{197}$Hg, and all beta negative and/or auger emitters. Some preferred radionuclides include: $^{90}$Y, $^{131}$I, $^{211}$At and $^{212}$Pb/$^{212}$Bi. all beta negative and/or auger emitters. The individual being treated may be diagnosed as having metastasized cancer or may be diagnosed as having localized cancer and may undergo the treatment proactively in the event that there is some metastasis as yet undetected. The pharmaceutical composition contains a therapeutically effective amount of the conjugated composition. A therapeutically effective amount is an amount which is effective to cause a cytotoxic or cytostatic effect on metastatic colorectal cancer and primary and/or metastatic stomach or esophageal cancer cells without causing lethal side effects on the individual. The composition may be injected intratumorally into primary tumors.

One aspect of the present invention relates to a method of detecting metastatic colorectal cancer and primary and/or metastatic stomach or esophageal cancer cells in an individual suspected of suffering from primary or metastatic colorectal, stomach or esophageal cancer by radioimaging. Individuals may be suspected of having primary stomach or esophageal tumors which diagnosis can be confirmed by administering to the individual, an imaging agent which binds to GCC. Tumors can be imaged by detecting localization at the stomach or esophagus. Individuals may be diagnosed as suffering from metastasized colorectal, stomach or esophageal cancer and the metastasized colorectal, stomach or esophageal cancer cells may be detected by administering to the individual, preferably by intravenous administration, a pharmaceutical composition that comprises a pharmaceutically acceptable carrier or diluent and a conjugated compound that comprises a compound of the invention and an active moiety wherein the active moiety is a radioactive and detecting the presence of a localized accumulation or aggregation of radioactivity, indicating the presence of cells with GCC. In some embodiments of the present invention, the pharmaceutical composition comprises a pharmaceutically acceptable carrier or diluent and a conjugated compound that comprises a compound of the invention and an active moiety wherein the active moiety is a radioactive. In some embodiments of the present invention, the pharmaceutical composition comprises a pharmaceutically acceptable carrier or diluent and a conjugated compound that comprises a compound of the invention and an active moiety wherein the active moiety is a radioactive agent selected from the group consisting of: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{77}$Br, $^{81}$Rb/$^{81}$MKr, $^{87}$MSr, $^{99}$MTc, $^{111}$In, $^{113}$MIn, $^{123}$I, $^{125}$I, $^{127}$Cs, $^{129}$Cs, $^{131}$I, $^{132}$I, $^{197}$Hg, $^{203}$Pb and $^{206}$206Bi. The individual being treated may be diagnosed as having metastasizing colorectal, stomach or esophageal cancer or may be diagnosed as having localized colorectal, stomach or esophageal cancer and may undergo the treatment proactively in the event that there is some metastasis as yet undetected. The pharmaceutical composition contains a diagnostically effective amount of the conjugated composition. A diagnostically effective amount is an amount which can be detected at a site in the body where cells with GCC are located without causing lethal side effects on the individual.

Photodynamic Imaging and Therapy

According to some embodiments of the invention, compounds of the invention are conjugates to photoactivated imaging agents or therapeutics. Maier A. et al. Lasers in Surgery and Medicine 26:461-466 (2000) which is incorporated herein by reference disclose an example of photodynamic therapy. QLT, Inc (Vancouver, BC) commercially distribute photosensitive active agents which can be linked to a compound of the invention. Such conjugated compounds can be used in photodynamic therapeutic and imaging protocols to activate the GCC-bound conjugated agents which are thus targeted to tumor cells. In some embodiments, the conjugated compounds are applied as an intraoperative spray which is subsequently exposed to light to activate compounds bound to cells that express GCC.

In some embodiments, the photodynamic agent is fluorophore or porphyrins. Examples of porphyrin include: hematoporphyrin derivative (HPD) and porfimer sodium (Photofrin®). A second generation photosensitizers is BPD verteporfin. In some embodiments the fluorophore is tetramethylrotamine. Lasers are generally the primary light source used to activate porphyrins. Light Emitting Diodes (LEDs) and florescent light sources may also be used in some applications.

In addition to an intraoperative spray, conjugated compounds may be delivered intrathecally, intraventrically, stereotactically, intrahepatically such as via the portal vein, by inhalation, and intrapleurally.

Drug Delivery Targeted to Colorectal, Stomach or Esophageal Cancer Cells Generally Another aspect of the invention relates to unconjugated and conjugated compositions which comprise a compound of the invention used to deliver therapeutic agents to cells that comprise a GCC such as metastatic colorectal cancer and primary and/or metastatic stomach or esophageal cancer cells. In some embodiments, the agent is a drug or toxin such as: methotrexate, doxorubicin, daunorubicin, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, *Pseudomonas* exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole. Genetic material is delivered to cancer cells to produce an antigen that can be targeted by the immune system or to produce a protein which kills the cell or inhibits its proliferation. In some embodiments, a compound of the invention is used to deliver nucleic acids that encode nucleic acid molecules which replace defective endogenous genes or which encode therapeutic proteins. In some embodiments, the compositions are used in gene therapy protocols to deliver to individuals, genetic material needed and/or desired to make up for a genetic deficiency.

In some embodiments, the compound of the invention is combined with or incorporated into a delivery vehicle thereby converting the delivery vehicle into a specifically targeted delivery vehicle. For example, a compound of the invention may be integrated into the outer portion of a viral particle making such a virus a GCC-bearing cell specific virus. Similarly, the coat protein of a virus may be engineered such that it is produced as a fusion protein which includes an active compound of the invention peptide that is exposed or otherwise accessible on the outside of the viral particle making such a virus a GCC-bearing cell-specific virus. In some embodiments, a compound of the invention may be integrated or otherwise incorporated into the liposomes wherein the compound of the invention is exposed or otherwise accessible on the outside of the liposome making such liposomes specifically targeted to GCC-bearing cells.

The active agent in the conjugated or unconjugated compositions according to this aspect of the invention is a drug, toxin or nucleic acid molecule. The nucleic acid may be RNA or preferably DNA. In some embodiments, the nucleic acid molecule is an antisense molecule or encodes an antisense sequence whose presence in the cell inhibits production of an undesirable protein. In some embodiments, the nucleic acid molecule encodes a ribozyme whose presence in the cell inhibits production of an undesirable protein. In some embodiments, the nucleic acid molecule encodes a protein or peptide that is desirably produced in the cell. In some embodiments, the nucleic acid molecule encodes a functional copy of a gene that is defective in the targeted cell. The nucleic acid molecule is preferably operably linked to regulatory elements needed to express the coding sequence in the cell.

Liposomes are small vesicles composed of lipids. Genetic constructs which encode proteins that are desired to be expressed in GCC-bearing cells are introduced into the center of these vesicles. The outer shell of these vesicles comprise a compound of the invention. Liposomes Volumes 1, 2 and 3 CRC Press Inc. Boca Raton Fla., which is incorporated herein by reference, disclose preparation of liposome-encapsulated active agents which include antibodies in the outer shell. In the present invention, a compound of the invention is associated with the in the outer shell. Unconjugated compositions which comprise a compound of the invention in the matrix of a liposome with an active agent inside.

In one embodiment, the delivery of normal copies of the p53 tumor suppressor gene to the cancer cells is accomplished using a compound of the invention to target the gene therapeutic. Mutations of the p53 tumor suppressor gene appears to play a prominent role in the development of many cancers. One approach to combating this disease is the delivery of normal copies of this gene to the cancer cells expressing mutant forms of this gene. Genetic constructs that comprise normal p53 tumor suppressor genes are incorporated into liposomes that comprise a compound of the invention. The composition is delivered to the tumor. Compound of the inventions specifically target and direct the liposomes containing the normal gene to correct the lesion created by mutation of p53 suppressor gene. Preparation of genetic constructs is with the skill of those having ordinary skill in the art. The present invention allows such construct to be specifically targeted by using the compound of the inventions of the present invention. The compositions of the invention include a compound of the invention associated with a delivery vehicle and a gene construct which comprises a coding sequence for a protein whose production is desired in the cells of the intestinal tract linked to necessary regulatory sequences for expression in the cells. For uptake by cells of the intestinal tract, the compositions are administered orally or by enema whereby they enter the intestinal tract and contact cells which comprise GCC. The delivery vehicles associate with the GCC by virtue of the compound of the invention and the vehicle is internalized into the cell or the active agent/genetic construct is otherwise taken up by the cell. Once internalized, the construct can provide a therapeutic effect on the individual.

Antisense

The present invention provides compositions, kits and methods which are useful to prevent and treat colorectal, stomach or esophageal cancer cells by providing the means to specifically deliver antisense compounds to colorectal, stomach or esophageal cancer cells and thereby stop expression of genes in such cells in which undesirable gene expression is taking place without negatively effecting cells in which no such expression occurs.

The conjugated compositions of the present invention are useful for targeting cells that express GCC including colorectal, stomach or esophageal cancer cells. The conjugated compositions will not bind to non-colorectal derived cells. Non-colorectal cells, lacking GCC, do not take up the conjugated compositions. Normal colorectal cells do have GCC and will take up the compositions. The present invention provides compositions and methods of delivering antisense compositions to normal and cancerous colorectal cells and stomach or esophageal cancer cells.

The present invention provides a cell specific approach in which only normal and cancerous colorectal cells and primary and/or metastatic stomach or esophageal cancer cells are exposed to the active portion of the compound and only those cells are effected by the conjugated compound. The compound of the invention binds to normal and cancerous colorectal cells and primary and/or metastatic stomach or esophageal cancer cells. Upon binding to these cells, the conjugated compound is internalized and the delivery of the conjugated compound including the antisense portion of the molecule is effected. The presence of the conjugated compound in normal colorectal cells has no effect on such cells because the cancer-associated gene for which the antisense molecule that makes up the active moiety of the conjugated compound is complementary is not being expressed. However, in colorectal cancer cells, the cancer gene for which the antisense molecule that makes up the active moiety of the conjugated compound is complementary is being expressed. The presence of the conjugated compound in colorectal cancer cells serves to inhibit or prevent transcription or translation of the cancer gene and thereby reduce or eliminate the transformed phenotype.

The invention can be used to combat primary and/or metastasized colorectal, stomach or esophageal cancer as well as to prevent the emergence of the transformed phenotype in normal colon cells. Thus the invention can be used therapeutically as well as prophylactically.

One having ordinary skill in the art can readily identify individuals suspected of suffering from stomach or esophageal cancer. In those individuals diagnosed with stomach or esophageal cancer, it is standard therapy to suspect metastasis and aggressively attempt to eradicate metastasized cells. The present invention provides pharmaceutical compositions and methods for specifically targeting and eliminating metastasized colorectal cancer cells and primary and/or metastatic stomach or esophageal cancer cells. Further, the present invention provides pharmaceutical compositions that comprise therapeutics and methods for specifically eliminating metastasized colorectal cancer cells and primary and/or metastatic stomach or esophageal cancer cells.

The present invention relies upon the use of a compound of the invention in a conjugated composition. The compound of the invention is essentially a portion of the conjugated composition which acts as a ligand to GCC and thus specifically binds to these receptors. The conjugated composition also includes an active moiety which is associated with the compound of the invention; the active moiety being an antisense composition useful to inhibit or prevent transcription or translation of expression of genes whose expression is associated with cancer.

According to the present invention, the active moiety is an antisense composition. In particular, the antisense molecule that makes up the active moiety of a conjugated compound hybridizes to DNA or RNA in a colorectal, stomach or esophageal cancer cell and inhibits and/or prevents transcription or translation of the DNA or RNA from taking place. The antisense compositions may be a nucleic acid molecule, a derivative or an analogs thereof. The chemical nature of the antisense composition may be that of a nucleic acid molecule or a modified nucleic acid molecule or a non-nucleic acid molecule which possess functional groups that mimic a DNA or RNA molecule that is complementary to the DNA or RNA molecule whose expression is to be inhibited or otherwise prevented. Antisense compositions inhibit or prevent transcription or translation of genes whose expression is linked to colorectal, stomach or esophageal cancer, i.e. cancer associated genes.

Point mutations insertions, and deletions in K-ras and H-ras have been identified in many tumors. Complex characteristics of the alterations of oncogenes HER-2/ERBB-2, HER-1/ERBB-1, HRAS-1, C-MYC and anti-oncogenes p53, RB1.

Chemical carcinogenesis in a rat model demonstrated point mutations in fos, an oncogene which mediates transcriptional regulation and proliferation. See: Alexander, R J, et al. Oncogene alterations in rat colon tumors induced by N-methyl-N-nitrosourea. American Journal of the Medical Sciences. 303(1):16-24, 1992, January which is hereby incorporated herein by reference including all references cited therein which are also hereby incorporated herein by reference.

Chemical carcinogenesis in a rat model demonstrated point mutations in the oncogene abl. See: Alexander, R J, et al. Oncogene alterations in rat colon tumors induced by N-methyl-N-nitrosourea. American Journal of the Medical Sciences. 303(1):16-24, 1992, January.

MYC is an oncogene that plays a role in regulating transcription and proliferation. A 15-base antisense oligonucleotide to myc complementary to the translation initiation region of exon II was incubated with colorectal cancer cells. This antisense molecule inhibited proliferation of colorectal cancer cells in a dos-dependent fashion. Interestingly, the uptake of this oligonucleotide was low (0.7%). Also, transfer of a normal chromosome 5 to colorectal cancer cells resulted in the regulation of myc expression and loss of proliferation. These data suggest that a tumor suppressor gene important in the regulation of myc is contained on this chromosome.

A novel protein tyrosine phosphatase, G1, has been identified. Examination of the mRNA encoding this protein in colorectal tumor cells revealed that it undergoes point mutations and deletions in these cells and may play a role in proliferation characteristic of these cells. Takekawa, M. et al. Chromosomal localization of the protein tyrosine phosphatase G1 gene and characterization of the aberrant transcripts in human colon cancer cells. FEBS Letters. 339(3): 222-8, 1994 Feb. 21, which is hereby incorporated herein by reference including all references cited therein which are also hereby incorporated herein by reference.

Gastrin regulates colon cancer cell growth through a cyclic AMP-dependent mechanism mediated by PKA. Antisense oligodeoxynucleotides to the regulatory subunit of a specific class of PKA inhibited the growth-promoting effects of cyclic AMP in colon carcinoma cells. See: Bold, R J, et al. Experimental gene therapy of human colon cancer. Surgery. 116(2):189-95; discussion 195-6, 1994 August and Yokozaki, H., et al. An antisense oligodeoxynucleotide that depletes RI alpha subunit of cyclic AMP-dependent protein kinase induces growth inhibition in human cancer cells. Cancer Research. 53(4):868-72, 1993 Feb. 15, which are both hereby incorporated herein by reference including all references cited therein which are also hereby incorporated herein by reference.

CRIPTO is an epidermal growth factor-related gene expressed in a majority of colorectal cancer tumors. Antisense phosphorothioate oligodeoxynucleotides to the 5'-end of CRIPTO mRNA significantly reduced CRIPTO expression and inhibited colorectal tumor cell growth in vitro and in vivo. Ciardiello, F. et al. Inhibition of CRIPTO expression and tumorigenicity in human colon cancer cells by antisense RNA and oligodeoxynucleotides. Oncogene. 9(1):291-8, 1994 January which are both hereby incorporated herein by reference including all references cited therein which are also hereby incorporated herein by reference.

Many carcinoma cells secrete transforming growth factor alpha. A 23 nucleotide antisense oligonucleotide to TGF alpha mRNA inhibited both DNA synthesis and proliferation of colorectal cancer cells. Sizeland, A M, Burgess, A W. Antisense transforming growth factor alpha oligonucleotides inhibit autocrine stimulated proliferation of a colon carcinoma cell line. Molecular Biology of the Cell. 3(11): 1235-43, 1992 November which is hereby incorporated herein by reference including all references cited therein which are also hereby incorporated herein by reference.

Antisense compositions including oligonucleotides, derivatives and analogs thereof, conjugation protocols, and antisense strategies for inhibition of transcription and translation are generally described in: Antisense Research and Applications, Crooke, S, and B. Lebleu, eds. CRC Press, Inc. Boca Raton Fla. 1993, Nucleic Acids in Chemistry and Biology Blackburn, G. and M. J. Gait, eds. IRL Press at Oxford University Press, Inc. New York 1990; and Oligonucleotides and Analoguesn: A Practical Approach Eckstein, F. ed., IRL Press at Oxford University Press, Inc. New York 1991; which are each hereby incorporated herein by reference including all references cited therein which are hereby incorporated herein by reference.

The antisense molecules of the present invention comprise a sequence complementary to a fragment of a colorectal cancer gene. See Ullrich et al., EMBO J., 1986, 5:2503, which is hereby incorporated herein by reference.

Antisense compositions which can make up an active moiety in conjugated compounds of the invention include oligonucleotides formed of homopyrimidines can recognize local stretches of homopurines in the DNA double helix and bind to them in the major groove to form a triple helix. See: Helen, C and Toulme, J J. Specific regulation of gene expression by antisense, sense, and antigene nucleic acids. Biochem. Biophys Acta, 1049:99-125, 1990 which is hereby incorporated herein by reference including all references cited therein which are hereby incorporated herein by reference. Formation of the triple helix would interrupt the ability of the specific gene to undergo transcription by RNA polymerase. Triple helix formation using myc-specific oligonucleotides has been observed. See: Cooney, M, et al. Science 241:456-459 which is hereby incorporated herein by reference including all references cited therein which are hereby incorporated herein by reference.

Antisense oligonucleotides of DNA or RNA complementary to sequences at the boundary between introns and exons can be employed to prevent the maturation of newly-generated nuclear RNA transcripts of specific genes into mRNA for transcription. Antisense RNA complementary to specific genes can hybridize with the mRNA for tat gene and prevent its translation. Antisense RNA can be provided to the cell as "ready-to-use" RNA synthesized in vitro or as an antisense gene stably transfected into cells which will yield antisense RNA upon transcription. Hybridization with mRNA results in degradation of the hybridized molecule by RNAse H and/or inhibition of the formation of translation complexes. Both result in a failure to produce the product of the original gene.

Antisense sequences of DNA or RNA can be delivered to cells. Several chemical modifications have been developed to prolong the stability and improve the function of these molecules without interfering in their ability to recognize specific sequences. These include increasing their resistance to degradation by DNases, including phosphotriesters, methylphosphonates, phosphorothioates, alpha-anomers, increasing their affinity for their target by covalent linkage to various intercalating agents such as psoralens, and increasing uptake by cells by conjugation to various groups including polylysine. These molecules recognize specific sequences encoded in mRNA and their hybridization prevents translation of and increases the degradation of these messages.

Conjugated compositions of the invention provide a specific and effective means for terminating the expression of genes which cause neoplastic transformation. GCC undergo ligand-induced endocytosis and can deliver conjugated compounds to the cytoplasm of cells.

Compound of the inventions are conjugated directly to antisense compositions such as nucleic acids which are active in inducing a response. For example, antisense oligonucleotides to MYC are conjugated directly to a compound of the invention. This has been performed employing peptides that bind to the CD4 receptor. See: Cohen, J S, ed. Oligodeoxynucleotides: Antisense Inhibitors of Gene Expression. Topics in Molecular and Structural Biology. CRC Press, Inc., Boca Raton, 1989. which is hereby incorporated herein by reference including all references cited therein which are hereby incorporated herein by reference. The precise backbone and its synthesis is not specified and can be selected from well-established techniques. Synthesis would involve either chemical conjugation or direct synthesis of the chimeric molecule by solid phase synthesis employing FMOC chemistry. See: Haralambidis, J, et aL (1987) Tetrahedron Lett. 28:5199-5202, which is hereby incorporated herein by reference including all references cited therein which are hereby incorporated herein by reference. Alternatively, the peptide-nucleic acid conjugate may be synthesized directly by solid phase synthesis as a peptide-peptide nucleic acid chimera by solid phase synthesis. Nielsen, P E, et al. (1994) Sequence-specific transcription arrest by peptide nucleic acid bound to the DNA template strand. Gene 149:139-145, which is hereby incorporated herein by reference including all references cited therein which are hereby incorporated herein by reference.

In some embodiments, polylysine can be complexed to conjugated compositions of the invention in a non-covalent fashion to nucleic acids and used to enhance delivery of these molecules to the cytoplasm of cells. In addition, peptides and proteins can be conjugated to polylysine in a covalent fashion and this conjugate complexed with nucleic acids in a non-covalent fashion to further enhance the specificity and efficiency of uptake of the nucleic acids into cells. Thus, the compound of the invention is conjugated chemically to polylysine by established techniques. The polylysine-compound of the invention conjugate may be complexed with nucleic acids of choice. Thus, polylysine-orosomucoid conjugates were employed to specifically plasmids containing genes to be expressed to hepatoma cells expressing the orosomucoid receptor. This approach can be used to delivery whole genes, or oligonucleotides. Thus, it has the potential to terminate the expression of an undesired gene (eg. MYC, ras) or replace the function of a lost or deleted gene (eg. hMSH2, hMLH 1, hPMS1, and hPMS2).

According to a preferred embodiment, Myc serves as a gene whose expression is inhibited by an antisense molecule within a conjugated composition. Compound of the inventions are used to deliver a 15-based antisense oligonucleotide to myc complementary to the translation initiation region of exon II. The 15-base antisense oligonucleotide to MYC is synthesized as reported in Collins, J F, Herman, P, Schuch, C, Bagby G C, Jr. Journal of Clinical Investigation. 89(5):1523-7, 1992 May. In some embodiments, the conjugated composition is conjugated to polylysine as reported previously. Wu, G Y, and Wu, C H. (1988) Evidence for ed gene delivery to Hep G2 hepatoma cells in vitro. Biochem. 27:887-892 which is incorporated herein by reference.

Conjugated compositions may be synthesized as a chimeric molecule directly by solid phase synthesis. pmolar to nanomolar concentrations for this conjugate suppress MYC synthesis in colorectal cancer cells in vitro.

Antisense molecules are preferably hybridize to, i.e. are complementary to, a nucleotide sequence that is 5-50 nucleotides in length, more preferably 5-25 nucleotides and in some embodiments 10-15 nucleotides.

In addition, mismatches within the sequences identified above, which achieve the methods of the invention, such that the mismatched sequences are substantially complementary to the cancer gene sequences are also considered within the scope of the disclosure. Mismatches which permit substantial complementarity to the cancer gene sequences will be known to those of skill in the art once armed with the present disclosure. The oligos may also be unmodified or modified.

Therapeutic compositions and methods may be used to combat colorectal, stomach or esophageal cancer in cases where the cancer is localized and/or metastasized. Individuals are administered a therapeutically effective amount of conjugated compound. A therapeutically effective amount is an amount which is effective to cause a cytotoxic or cytostatic effect on cancer cells without causing lethal side effects on the individual. An individual who has been administered a therapeutically effective amount of a conjugated composition has a increased chance of eliminating colorectal, stomach or esophageal cancer as compared to the risk had the individual not received the therapeutically effective amount.

To treat localized colorectal, stomach or esophageal cancer, a therapeutically effective amount of a conjugated compound is administered such that it will come into contact with the localized tumor. Thus, the conjugated compound may be administered orally or intratumorally. Oral and rectal formulation are taught in Remington's Pharmaceutical Sciences, 18th Edition, 1990, Mack Publishing Co., Easton Pa. which is incorporated herein by reference.

The pharmaceutical compositions according to the present invention may be administered as either a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The present invention is directed to a method of delivering antisense compounds to normal and cancerous colorectal cells and to stomach or esophageal cancer cells and inhibiting expression of cancer genes in mammals. The methods comprise administering to a mammal an effective amount of a conjugated composition which comprises a compound of the invention conjugated to an antisense oligonucleotide having a sequence which is complementary to a region of DNA or mRNA of a cancer gene.

The conjugated compounds may be administering to mammals in a mixture with a pharmaceutically-acceptable carrier, selected with regard to the intended route of administration and the standard pharmaceutical practice. Dosages will be set with regard to weight, and clinical condition of the patient. The conjugated compositions of the present invention will be administered for a time sufficient for the mammals to be free of undifferentiated cells and/or cells having an abnormal phenotype. In therapeutic methods treatment extends for a time sufficient to inhibit transformed cells from proliferating and conjugated compositions may be administered in conjunction with other chemotherapeutic agents to manage and combat the patient's cancer.

The conjugated compounds of the invention may be employed in the method of the invention singly or in combination with other compounds. The amount to be administered will also depend on such factors as the age, weight, and clinical condition of the patient. See Gennaro, Alfonso, ed., Remington's Pharmaceutical Sciences, 18th Edition, 1990, Mack Publishing Co., Easton, Pa.

Methods and Compositions for Making and Using Targeted Gene Therapy, Antisense and Drug Compositions.

Liposomes may be prepared by well known means wherein Compound of the inventions may be exposed on the outside of the liposomes. Such liposomes may contain any of the active agents descried herein in other sections of this specification. Alternatively, genetic constructs may be provided within the liposomes to deliver gene therapeutics to non-malignant and malignant intestinal cells or extraintestinal cells such as stomach or espophageal cancer cells, which express GCC. Delivery to non-malignant intestinal cells may be useful to provide such cells with functional genes to express proteins for which the individual is lacking an functional gene, to supplement the individuals gene or to provide a therapeutic protein. For example, in patients suffering cystic fibrosis, the incorporation of a DNase gene in the intestinal cells may provide therapeutic benefit to the individual. Similarly, in patients with intestinal disorders such as inflammatory bowel disease or Crohn's disease, genes which can down regulate immune response or protect cells against the self-directed immune response may be useful.

Methods of Preventing and Treating Diarrhea

Accordingly, the present invention relates to a method of negatively regulating guanylyl cyclase C (GC-C) enzyme activity by activating an inhibitory pathway. According to the present invention, GC-C enzyme activity is inhibited by contacting cells that have active GC-C enzyme with an effective amount of a compound of the invention or a pharmaceutically acceptable salt thereof. GC-C compound of the inventions are useful to prevent or treat GC-C-mediated diarrhea. The present invention relates to a method of preventing an individual from suffering from GC-C-mediated diarrhea, such as infectious diarrhea, comprising the step of administering to such an individual, an amount of a compound of the invention, or a pharmaceutically acceptable salt thereof to inhibit GC-C activity. The present invention relates to a method of treating an individual suffering from GC-C-mediated diarrhea, such as infectious diarrhea, comprising the step of administering to such an individual, an amount of a compound of the invention, or a pharmaceutically acceptable salt thereof to inhibit GC-C activity.

According to some aspects of the invention, methods are provided to prevent diarrhea in humans induced by ST producing organisms in developing countries; to prevent growth retardation in children in developing countries in which ST-producing organisms are endemic; to prevent travelers' diarrhea; and to prevent scours and other diarrheal diseases in animals; as well as to treat secretory diarrhea of unknown etiology; and to treat irritable bowel syndrome and other forms of diarrhea including, but not limited to, diarrhea associated with inflammatory bowel disease, sprue, etc.

The method of the present invention comprises inhibiting GC-C activity by contacting cells that have active GC-C with an effective amount of a compound of the invention, or a pharmaceutically acceptable salt thereof. Antagonist compounds according to the invention have been discovered to negatively regulate the activity of GC-C. Exposure of cells in vitro a compound of the invention has resulted in the inhibition of GC-C activity. Inhibition of GC-C activity in cells impedes the pathway associated with GC-C-mediated diarrhea.

The method that is the present invention is useful in the prevention and treatment of conditions associated with active GC-C; specifically GC-C-mediated diarrhea such as infectious diarrhea. Accordingly, the present invention relates to a method of preventing GC-C-mediated diarrhea in or treating a individual suffering from GC-C-mediated diarrhea. The present invention relates to a method of preventing infectious in an a individual susceptible to infectious diarrhea. The present invention relates to a method of treating an individual suffering from infectious diarrhea. The individual is preferably a mammal, more preferably a human. In some embodiments, the individual may be a canine, feline, bovine, ovine or equine species.

The identification of an individual suspected of suffering from GC-C-mediated diarrhea such as infectious diarrhea is routine and can be performed by those having ordinary skill in the art. Infectious diarrhea, also referred to as travelers diarrhea, can be identified routinely. In addition to being useful to treating individuals suspected of suffering from GC-C-mediated diarrhea, the present invention is useful prophylactically to prevent the incidence of GC-C-mediated diarrhea in individuals at risk of contracting the condition. For example, travelers and those living in situations for which they are unaccustomed may be at risk. Those having ordinary skill in the art can readily identify conditions which place an individual at risk of contracting GC-C-mediated infectious diarrhea.

In some preferred embodiments, the method that is the invention is a method of treating an individual suspected of suffering from GC-C mediated diarrhea comprising the step of administering to said individual, an effective amount of a compound of the invention compound. In addition, pharmaceutically acceptable salts of these compounds may be used in the method that is the present invention.

Pharmaceutically acceptable salts of these compounds may be used in practicing the method that is the present invention. Pharmaceutical compositions containing the compounds or salts may also be used in practicing the method that is the present invention. Pharmaceutically acceptable salts useful in the method of that is the invention include sodium, potassium, calcium, zinc, lithium, magnesium, aluminum, diethanolamine, tromethamine, ethylenediamine, meglumine, hydrochloric, hydrobromic or acetic acid.

The present invention relates to a method of using antagonist compounds of the invention to inhibit the activity of GC-C in cells. The range of amounts of compound of the invention that a cell can be exposed to that is effective for inhibiting GC-C activity can be determined by one having ordinary skill in the art.

By inhibiting GC-C activity, the method that is the present invention is useful in the treatment of GC-C-mediated diarrhea. Effective amounts of compound of the inventions used in the method that is the present invention can be formulated as pharmaceutical preparations and administered to individuals who are suspected of suffering from or being susceptible to GC-C mediated diarrhea, in order to counter the biochemical pathway which leads to the condition at the cellular level.

Treatment of GC-C-mediated diarrhea can be performed by administration of effective amounts of a pharmaceutical preparation of compound of the invention to inhibit GC-C. Compounds can be formulated for human and animal prophylactic and therapeutic applications by those having ordinary skill in the art. The dosage range of a compound to be administered to mammals, particularly humans, to be effective in the treatment or prevention of GC-C mediated diarrhea can be determined by those having ordinary skill in the art.

Pharmaceutical preparations incorporating compounds used in the method that is the invention can be used to block GC-C activity related to the biochemical pathway which results in diarrhea by administration of effective amounts of pharmaceutical preparation that comprise compounds disclosed herein. The compounds used in the method that is the invention can be formulated for human and animal prophylactic and therapeutic applications by those having ordinary skill in the art. The range of amounts of a compound to be administered to mammals, particularly humans, to be effective in treating or preventing GC-C-mediated diarrhea can be determined by those having ordinary skill in the art.

The mode of administration of compounds and pharmaceutical compositions according to the method that is the invention includes any means that produces contact of the active ingredient with the agent's site of action in the body of a mammal, that is in the cells of the colon. These modes of administration include but not limited to oral, topical, hypodermal, intravenous, intraanally, intramuscular and intraparenteral methods of administration. The preferred route of administration is orally.

In practicing the method that is the invention, the compounds may be administered singly or in combination with other compounds useful for treating or preventing diarrhea. In the method that is the invention, the compounds are preferably administered with a pharmaceutically acceptable carrier selected on the basis of the selected route of administration and standard pharmaceutical practice.

The method may include administration of compounds to mammals, preferably humans, in therapeutically effective amounts which are effective to inhibit GC-C. The dosage administered in any particular instance will depend upon factors such as the pharmacodynamic characteristics of the compound of the invention, its mode and route of administration; age, health, and weight of the recipient; nature and extent of symptoms; kind of concurrent treatment, frequency of treatment, and the effect desired.

It is contemplated that the daily dosage of a compound used in the method that is the invention will be in the range of from about 1 micrograms to about 10 grams per day. In some preferred embodiments, the daily dosage compound will be in the range of from about 10 mg to about 1 gram per day. In some preferred embodiments, the daily dosage compound will be in the range of from about 100 mg to about 500 mg per day. It is contemplated that the daily dosage of a compound used in the method that is the invention will be in the range of from about 1 µg to about 100 mg per kg of body weight, in some embodiments, from about 1 µg to about 40 mg per kg body weight; in some embodiments from about 10 µg to about 20 mg per kg per day, and in some embodiments 10 µg to about 1 mg per kg per day.

Pharmaceutical compositions may be administered in a single dosage, divided dosages or in sustained release. In some preferred embodiments, the compound will be administered in multiple doses per day. In some preferred embodiments, the compound will be administered in 3-4 doses per day.

The method of administering compounds include administration as a pharmaceutical composition orally in solid dosage forms, such as capsules, tablets, and powders, or in liquid dosage forms, such as elixirs, syrups, and suspensions. The compounds may also be administered parenterally in sterile liquid dosage forms or topically in a carrier. The compounds may be formulated into dosage forms according to standard practices in the field of pharmaceutical preparations. See Remington's Pharmaceutical Sciences, A. Osol, Mack Publishing Company, Easton, Pa.

Compounds may be mixed with powdered carriers, such as lactose, sucrose, mannitol, starch, cellulose derivatives, magnesium stearate, and stearic acid for insertion into gelatin capsules, or for forming into tablets. Both tablets and capsules may be manufactured as sustained release products for continuous release of medication over a period of hours. Compressed tablets can be sugar or film coated to mask any unpleasant taste and protect the tablet from the atmosphere or enteric coated for selective disintegration in the gastrointestinal tract. In some preferred embodiments, compounds are delivered orally and are coated with an enteric coating which makes the compounds available upon passing through the stomach and entering the intestinal tract, preferably upon entering the large intestine. U.S. Pat. No. 4,079,125, which is incorporated herein by reference, teaches enteric coating which may be used to prepare enteric coated compound of the inventions useful in the methods of the invention.

Liquid dosage forms for oral administration may contain coloring and flavoring to increase patient acceptance, in addition to a pharmaceutically acceptable diluent such as water, buffer or saline solution.

For parenteral administration, a compound may be mixed with a suitable carrier or diluent such as water, a oil, saline solution, aqueous dextrose (glucose), and related sugar solutions, and glycols such as propylene glycol or polyethylene glycols. Solutions for parenteral administration contain preferably a water soluble salt of the compound. Stabilizing agents, antioxidizing agents and preservatives may also be added. Suitable antioxidizing agents include sodium bisulfite, sodium sulfite, and ascorbic acid, citric acid and its salts, and sodium EDTA. Suitable preservatives include benzalkonium chloride, methyl- or propyl-paraben, and chlorbutanol.

According to some aspects of the invention, the prevention of diarrhea and the dehydration that accompanies it in children prevents growth retardation, a significant problem among in children in developing countries in which ST-producing organisms are endemic. Travelers can prevent travelers' diarrhea be prophylactical administration of compound of the inventions prior to and during travel to locations where ST-producing organisms are endemic. The administration of compound of the inventions can be used to prevent scours and other diarrheal diseases in animals identified as being susceptible to the same. Individuals suffering from secretory diarrhea of unknown etiology may be treated by administration of compound of the inventions. Aspects of the present invention include treatment of individuals identified as having irritable bowel syndrome or other forms of diarrhea be administering to them therapeutic amounts of compound of the invention.

Aspects of the present invention include methods of imaging proximal renal tubules and treating renal diseases and disorders involving the same such as some renal cancer, methods of imaging exocrine duct cells of the pancreas and treating pancreatic diseases and disorders involving the same such as some pancreatic cancer, methods of imaging submandibular glands and treating diseases and disorders involving the same, and the methods of imaging bile duct and treating diseases and disorders involving the same such as some gall bladder cancers. In each case, the teachings above may be generally applied and adapted from the those discussed above.

EXAMPLES

Example 1

Compound of the inventions of GCC that binds to the receptor with high affinity but does not induce the production of cyclic GMP has been designed. The peptides block the ability of ST, the most potent agonist of GCC known, to bind to GCC and induce accumulation of cyclic GMP. Thus, the peptides fulfill the criteria for a compound of the invention of GCC. The structure of these compound of the inventions identify a core peptide mediating binding to GCC and the agonist switch which induces the production of cyclic GMP.

The molecules were derived from ST. Comparison of the structure of the compound of the invention with the known agonists reveal the core determinants required for receptor occupancy and agonist activation. All known biologically-active GCC agonists possess intrachain disulfides between cysteines at positions 6 and 14 and positions 9 and 17. In addition, some agonists, such as the STs, have an intrachain disulfide between cysteines at position 5 and 10. The compound of the invention, which binds to GCC but does not activate cyclic GMP production, retains the intrachain disulfides at positions 5 and 10 and positions 6 and 14, but not the disulfide at positions 9 and 17. These data demonstrate that the core structure consisting of residues 5-17 and possessing disulfides at positions 5 and 10 and positions 6 and 14 encompasses the determinants to bind to GCC, but that the structure formed by and encompassing the positions 9 and 17 intrachain disulfide contains the agonist switch that activates GCC to produce cyclic GMP.

The identification of this structure provides a platform for developing agonists and compound of the inventions for GCC which exhibit greater potency, efficacy and specificity than existing ligands. In addition, this structure provides a platform for developing non-peptide agonists and compound of the inventions, conferring greater stability to facilitate oral, intravenous, subcutaneous or other delivery in the absence of degradation by proteases.

The structures of the compound of the inventions are set forth in Table 2 together with the structure for the *E. coli* heat stable entertoxin STa. The numerical positions refer to those of the Sta toxin.

| Position | | 5 | 6 | | | 9 | 10 | | | 14 | | | 17 |
|---|---|---|---|---|---|---|---|---|---|---|---|---|---|
| *E. coli* STa ST(4-14) | NT F Y | C | C | E | L | C | C | N | P | A | C | A G | C Y |
| Ala9,17 ST(4-14) | | C | C | E | L | A | C | N | P | A | C | A G | A |
| NMeLeu9 ST(4-14) | Y | C | C | E | L | L*  | C | N | P | A | C | | |
| NMeAla9 ST(4-14) Phe9 Cys(Mob)5,10 | Y | C | C | E | L | A* | C | N | P | A | C | A G | A |
| Mono ST(4-14) Phe9 | Y | C†C | | E | L | F | C†N | P | A | C | A G | A |
| ST(4-14) | Y | C | C | E | L | F | C | N | P | A | C | | |
| NMeVal9 ST(5-14) | Y | C | C | E | L | V* | C | N | P | A | C | | |
| Ala9Tyr15 ST(4-14) | | C | C | E | L | A | C | N | P | A | C | | Y |
| Thr9Tyr15 ST(4-14) | | C | C | E | L | T | C | N | P | A | C | | Y |

-continued

| Position | 5 | 6 | | 9 | 10 | | | 14 | | | 17 |
|---|---|---|---|---|---|---|---|---|---|---|---|
| Thr9 Aib13e ST(4-14) | Y | C | C | E | L | T | C | N | P | α | C |
| Thr9Aib12 ST(4-14) | Y | C | C | E | L | T | C | N | α | A | C |
| Leu9Tyr15 ST(4-14) | Y | C | C | E | L | L | C | N | P | A | C Y |
| Ala9 NMeAla13 ST(5-14) Ala9 | Y | C | C | E | L | A | C | N | P | A* | C |
| ST(6-14) Mpr5 | | C | C | E | L | A | C | N | P | A | C |
| Ala9 Carba5,10 | | γδC | | E | L | A | δ | N | P | A | C |

\* indicates amino acid is N methylated
† indicates amino acid is blocked with Mob
α indicates Aib
γ indicates Mpr
δ indicates Carba linkage Example 2

T84 human colorectal adenocarcinoma cells were grown to confluence in culture and harvested using a trypsin/EDTA solution. These cells were diluted 10-fold (v/v) with Dulbecco's minimal essential medium/F12, plus 10% fetal bovine serum (DMEM/F12/FBS) and plated at a density of 20,000 cells/well into a Falcon 96-well plate. The cells in this 96-well plate were grown to near confluence in the DMEM/F12/FBS, then washed once sequentially with 200 microliters each of Dulbecco's phosphate buffered saline (No Ca or Mg) and Opti-mem serum-free media. The Opti-mem media was removed and replaced with 90 microliters of Opti-mem media containing 1.1 mM IBMX (iso). This solution was incubated with the cells for 15 minutes at 37 degrees C. and then 10 microliters of an ST analog (10× desired final concentration) was added. This solution was mixed and incubated at 37 degrees Celsius for 15 minutes before the media was aspirated off and replaced with 200 microliters of lysis reagent 1 (0.5% dodecyltrimethylammonium bromide, aqueous) from the Amersham Biosciences cGMP Enzyme Immunoassay Biotrak System and incubated at 37 degrees Celsius for 15 minutes. cGMP levels were quantified against a cGMP standard curve using the Amersham Biosciences cGMP competitive Enzyme Immunoassay Biotrak System. This System detects cGMP in the following manner: a Donkey anti-rabbit IgG is adhered to the immunoassay plate and incubated with Rabbit anti-cGMP antibody. The wells are then co-incubated with cell culture lysate and a standard amount of cGMP-horseradish peroxidase conjugate for two hours at 4 degrees Celsius and washed prior to addition of the substrate 3,3',5,5'-tetramethylbenzidine/hydrogen peroxide which generates a blue color. The addition of 100 microliters of 1 M sulfuric acid (aq) stabilizes the color and it is then read at 450 nm. The data is shown in FIG. 5.

SEQUENCE LISTING

The Specification includes recitation of the Sequence Listing found in ASCII text file name 100051-11701seqlisting, created and submitted to the United States Patent and Trademark Office on Oct. 18, 2013 (8.5 kilobytes), which is incorporated by reference in its entirety.

The invention claimed is:

1. A pharmaceutical composition comprising:
   a) compound having the formula of Formula (II):

R201-R202-R203-R204-R205-R206-R207    (II)

wherein:
   i) R201 is 0-20 amino acids;
   R202 is cysteine or penicillamine;
   R203 is alanine or serine;
   R204 is E-L;
   R205 is alanine, serine or blocked cysteine that cannot cross-link with another amino acid;
   R206 is cysteine or penicillamine; and,
   R207 is absent or 1-30 amino acids;
   wherein R202 is cross-linked to R206 by a di-sulphide bond and the compound is a GCC antagonist, or ii) R201 is 0-20 amino acids;
   R202 is cysteine or penicillamine;
   R203 is alanine, or serine or blocked cysteine that cannot cross-link with another amino acid;
   R204 is E-L;
   R205 is alanine;
   R206 is cysteine or penicillamine; and,
   R207 is absent or 1-30 amino acids;
   wherein R202 is cross-linked to R206 by a di-sulphide bond and the compound is a GCC antagonist; and
   b) a suitable pharmaceutical carrier.

2. The pharmaceutical composition of claim 1 wherein R201 is absent or tyrosine.

3. The pharmaceutical composition of claim 1 wherein R202 is cysteine.

4. The pharmaceutical composition of claim 1 wherein R203 is serine or alanine.

5. The pharmaceutical composition of claim 1 wherein R205 is alanine.

6. The pharmaceutical composition of claim 1 wherein R206 is cysteine.

7. A conjugated compound that comprises a moiety of Formula (II) that is conjugated to an active moiety which is selected from the group consisting of a radionuclide, an enzyme, a fluorescent label, a metal chelating group, a chemiluminescent label, a bioluminescent label, a chemotherapeutic, a toxin, an inactive prodrug, a radiosensitizing agent, a photodynamic agent, a nucleic acid molecule and combinations thereof; wherein Formula (II) is

R201-R202-R203-R204-R205-R206-R207 (II)

wherein:
R201 is absent or tyrosine;
R202 is cysteine or penicillamine;
R203 is alanine, serine or blocked cysteine that cannot cross-link with another amino acid;
R204 is E-L;
R205 is alanine, serine or blocked cysteine that cannot cross-link with another amino acid;
R206 is cysteine or penicillamine;
R207 is absent;
R202 is cross-linked to R206 by a di-sulphide bond; and
the compound is a GCC antagonist.

8. A pharmaceutical composition comprising liposomes that comprise
a) a compound having the formula of Formula (II):

R201-R202-R203-R204-R205-R206-R207 (II)

wherein:
R201 is 0-20 amino acids;
R202 is cysteine or penicillamine;
R203 is alanine, serine or blocked cysteine that cannot cross-link with another amino acid;
R204 is E-L;
R205 is alanine, serine or blocked cysteine that cannot cross-link with another amino acid;
R206 is cysteine or penicillamine; and,
R207 is absent or 1-30 amino acids;
wherein R202 is cross-linked to R206 by a di-sulphide bond and the compound is a GCC antagonist;
b) a suitable pharmaceutical carrier; and
c) an active agent selected from the group consisting of: a radionuclide, an enzyme, a fluorescent label, a metal chelating group, a chemiluminescent label, a bioluminescent label, a chemotherapeutic, a toxin, an inactive prodrug, a radiosensitizing agent, a photodynamic agent, a nucleic acid molecule or combinations thereof.

9. A pharmaceutical composition comprising:
a) compound having the formula of Formula (II):

R201-R202-R203-R204-R205-R206-R207 (II)

wherein:
R201 is absent or tyrosine;
R202 is cysteine or penicillamine;
R203 is serine, alanine or blocked cysteine;
R204 is E-L;
R205 is alanine or blocked cysteine;
R206 is cysteine or penicillamine; and
R207 is absent;
wherein R202 is cross-linked to R206 by a di-sulphide bond and the compound is a GCC antagonist; and
b) a suitable pharmaceutical carrier.

10. The pharmaceutical composition of claim 1 wherein:
R201 is tyrosine;
R202 is cysteine;
R203 is serine;
R204 is E-L;
R205 is alanine;
R206 is cysteine; and
R207 is absent.

11. The pharmaceutical composition of claim 1 wherein:
R201 is absent, Y, NTFY—SEQ ID NO 12, SSSNY—SEQ ID NO 9, SSDWDY—SEQ ID NO 10, ID, PN, or QE.

12. The pharmaceutical composition of claim 1 wherein:
R207 is absent.

13. A sterile, pyrogen free injectable pharmaceutical composition comprising a conjugated compound of claim 7.

14. The pharmaceutical composition of claim 1 formulated for oral delivery to a mammal.

15. A pharmaceutical composition comprising:
a) compound having the formula of Formula (II):

R201-R202-R203-R204-R205-R206-R207 (II)

wherein:
R201 is 0-20 amino acids;
R202 is cysteine or penicillamine;
R203 is alanine, serine or blocked cysteine that cannot cross-link with another amino acid;
R204 is E-L;
R205 is alanine, serine or blocked cysteine that cannot cross-link with another amino acid;
R206 is cysteine or penicillamine; and,
R207 is absent or 1-30 amino acids;
wherein R202 is cross-linked to R206 by a di-sulphide bond and the compound is a GCC antagonist; and
b) a suitable pharmaceutical carrier;
wherein the pharmaceutical composition is formulated for oral delivery to a mammal and in the form of a tablet or capsule.

16. A method of treating cancer characterized by expression of GCC in an individual comprising the step of administering to the individual a conjugated compound of claim 7 in which the active moiety kills or inhibits replication of cells to which the conjugated compound binds.

* * * * *